(12) United States Patent
Crew et al.

(10) Patent No.: US 7,648,987 B2
(45) Date of Patent: Jan. 19, 2010

(54) BICYCLIC PROTEIN KINASE INHIBITORS

(75) Inventors: Andrew Philip Crew, Farmingdale, NY (US); Han-Qing Dong, Farmingdale, NY (US); Mark Joseph Mulvihill, Farmingdale, NY (US); Douglas S. Werner, Farmingdale, NY (US); Mridula Kadalbajoo, Farmingdale, NY (US); Radoslaw Laufer, Farmingdale, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 11/633,301

(22) Filed: Dec. 4, 2006

(65) Prior Publication Data

US 2007/0149521 A1 Jun. 28, 2007

Related U.S. Application Data

(60) Provisional application No. 60/741,588, filed on Dec. 2, 2005.

(51) Int. Cl.
*C07D 471/06* (2006.01)
*A61K 31/4985* (2006.01)

(52) U.S. Cl. .................................... 514/249; 544/350

(58) Field of Classification Search ................ 514/300, 514/249; 544/350
See application file for complete search history.

(56) References Cited

U.S. PATENT DOCUMENTS

| | | | |
|---|---|---|---|
| 5,217,999 A | 6/1993 | Levitzki |
| 5,302,606 A | 4/1994 | Spada |
| 5,326,905 A | 7/1994 | Dow |
| 5,397,787 A | 3/1995 | Buzzetti |
| 5,556,874 A | 9/1996 | Dobrusin |
| 6,194,439 B1 | 2/2001 | Dow |
| 6,265,411 B1 | 7/2001 | Thomas |
| 6,337,338 B1 | 1/2002 | Kozlowski |
| 6,362,336 B1 | 3/2002 | Lohmann |
| 6,486,179 B2 | 11/2002 | Jirousek |
| 6,713,474 B2 | 3/2004 | Hirst |
| 6,939,874 B2 | 9/2005 | Harmange |
| 7,087,602 B2 | 8/2006 | Thomas |
| 7,115,617 B2 | 10/2006 | Buchanan |
| 7,244,733 B2 | 7/2007 | Hunt |
| 7,326,699 B2 | 2/2008 | Capraro |
| 7,348,358 B2 | 3/2008 | Larsson |
| 2004/0014774 A1 | 1/2004 | Myers |
| 2005/0009832 A1 | 1/2005 | Li |
| 2005/0054638 A1 | 3/2005 | Barlaam |
| 2005/0215564 A1 | 9/2005 | Stiles |
| 2006/0235031 A1 | 10/2006 | Arnold |
| 2007/0238734 A1 | 10/2007 | Nemecek |

FOREIGN PATENT DOCUMENTS

| | | | |
|---|---|---|---|
| JP | 07/133280 | | 5/1995 |
| JP | 2005089352 A | * | 4/2005 |
| WO | WO 97/28161 | | 8/1997 |
| WO | WO 01/72751 | | 10/2001 |
| WO | WO 2005/097800 | * | 10/2005 |

OTHER PUBLICATIONS

Dorwald F. A. Side Reactions in Organic Synthesis, 2005, Wiley: VCH, Weinheim p. IX of Preface p. 1-15, 41, 279-308.*
Michelotti et. al. "Two classes of p38a MAP kinase inhibitors having a common diphenylether core but exhibiting divergent binding modes" Bioorganic & Medicinal Chemistry Letters 2005, 15, 5274-5279.*
Jiang et. al. "3,5-Disubstituted quinolines as novel c-Jun N-terminal kinase inhibitors." Bioorganic & Medicinal Chemistry Letters 2007, 17, 6378-6382.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*
Snow et. al. "Hit-to-lead studies on benzimidazole inhibitors of ITK: Discovery of a novel class of kinase inhibitors" Bioorganic & Medicinal Chemistry Letters 2007 17 3660-3665.*
Miyazaki et. al. "Design and effective synthesis of novel templates, 3,7-diphenyl-4- amino-thieno and furo-[3,2-c]pyridines as protein kinase inhibitors and in vitro evaluation targeting angiogenetic kinases" Bioorganic & Medicinal Chemistry Letters 2007, 17, 250-254.*
Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*
Mulvihill et. al. "1,3-Disubstituted-imidazo[1,5-a]pyrazines as insulin-like growth-factor-I receptor (IGF-IR) inhibitors" Bioorganic & Medicinal Chemistry Letters 2007, 17, 1091-1097.*

(Continued)

*Primary Examiner*—Rita J Desai
*Assistant Examiner*—David K O'Dell

(57) ABSTRACT

Compounds of the Formula

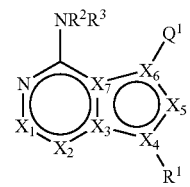

and pharmaceutically acceptable salts thereof, wherein $X_1$, $X_2$, $X_3$, $X_4$, $X_5$, $X_6$, $X_7$, $R^1$, and $Q^1$ are defined herein, inhibit protein kinase enzymes and are useful for the treatment and/or prevention of hyperproliferative diseases such as cancer, inflammation, psoriasis, allergy/asthma, disease and conditions of the immune system, disease and conditions of the central nervous system.

8 Claims, No Drawings

OTHER PUBLICATIONS

Dineen et. al. "Efficient Transamidation of Primary Carboxamides by in Situ Activation with N,N-Dialkylformamide Dimethyl Acetals" Journal of the American Chemical Society, 2006, 128, 16406-16409.*

Knochel et. al. "Mild Synthesis of Polyfunctional Benzimidazoles and Indoles by the Reduction of Functionalized Nitroarenes with Phenylmagnesium Chloride" Chemistry a European Journal 2003, 9, 5323-5331.*

Albert, A. et al. (1969) Chem. Biol.Pterdines.Proc.Int.Symp., $4^{th}$, 4:1-5.

Albert, A. et al. (1970) Journal of the Chemical Society, vol. 11, pp. 1540-1547.

Database WPI Week 200529, Derwent Publications Ltd., London, GB.

Expert Opinion Ther. Pat., (1998) vol. 8, pp. 475-478.

Hartz R A et al (2002) Bioorganic & Medicinal Chemistry Letters, vol. 12,pp. 291-294.

Parrizas et al (1997) Endocrinology, vol. 138, pp. 1427-1433.

Abstract of JP 07/133280.

Machine English Translation of JP 07/133280.

International Search Report in PCT/US2006/046226.

Written Opinion of the International Search Authority in PCT/US2006/046226.

* cited by examiner

BICYCLIC PROTEIN KINASE INHIBITORS

This application claims the benefit of U.S. Provisional Application No. 60/741,588 filed on Dec. 2, 2005, which is herein incorporated by reference in its entirety.

BACKGROUND OF THE INVENTION

The present invention is directed to novel heterobicyclic compounds, their salts, and compositions comprising them. In particular, the present invention is directed to novel heterobicyclic compounds that inhibit the activity of kinase enzymes in animals, including humans, for the treatment and/or prevention of various diseases and conditions such as cancer. The compounds of the present invention are inhibitors of at least one of, but not limited to, the following: IGF-1R, mTOR, Aurora A, Blk, CHK1, c-RAF, Flt3, Fyn, Lck, MAPK2, ROCK-II, Tie-2, KDR, or Fak.

Protein tyrosine kinases (PTKs) are enzymes that catalyse the phosphorylation of specific tyrosine residues in various cellular proteins involved in regulation of cell proliferation, activation, or differentiation (Schlessinger and Ullrich, 1992, *Neuron* 9:383-391). Aberrant, excessive, or uncontrolled PTK activity has been shown to result in uncontrolled cell growth and has been observed in diseases such as benign and malignant proliferative disorders, as well as having been observed in diseases resulting from an inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular). The Receptor Tyrosine Kinases (RTKs) comprise a large family of transmembrane receptors with at least nineteen distinct RTK subfamilies having diverse biological activities. The RTK family includes receptors that are crucial for the growth and differentiation of a variety of cell types (Yarden and Ullrich, *Ann. Rev. Biochem.* 57:433-478, 1988; Ullrich and Schlessinger, *Cell* 61:243-254, 1990). The intrinsic function of RTKs is activated upon ligand binding, which results in phosphorylation of the receptor and multiple cellular substrates, and subsequently results in a variety of cellular responses (Ullrich & Schlessinger, 1990, *Cell* 61:203-212). Thus, RTK mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate a corresponding cellular response such as cell division, differentiation, metabolic effects, and changes in the extracellular microenvironment (Schlessinger and Ullrich, 1992, *Neuron* 9:1-20).

Malignant cells are associated with the loss of control over one or more cell cycle elements. These elements range from cell surface receptors to the regulators of transcription and translation, including the insulin-like growth factors, insulin growth factor-I (IGF-1) and insulin growth factor-2 (IGF-2) (M. J. Ellis, "The Insulin-Like Growth Factor Network and Breast Cancer", Breast Cancer, Molecular Genetics, Pathogenesis and Therapeutics, Humana Press 1999). The insulin growth factor system consists of families of ligands, insulin growth factor binding proteins, and receptors.

A major physiological role of the IGF-1 system is the promotion of normal growth and regeneration. Overexpressed IGF-1R (type 1 insulin-like growth factor receptor) can initiate mitogenesis and promote ligand-dependent neoplastic transformation. Furthermore, IGF-1R plays an important role in the establishment and maintenance of the malignant phenotype.

IGF-1R exists as a heterodimer, with several disulfide bridges. The tyrosine kinase catalytic site and the ATP binding site are located on the cytoplasmic portion of the beta subunit. Unlike the epidermal growth factor (EGF) receptor, no mutant oncogenic forms of the IGF-1R have been identified. However, several oncogenes have been demonstrated to affect IGF-1 and IGF-1R expression. The correlation between a reduction of IGF-1R expression and resistance to transformation has been seen. Exposure of cells to the mRNA antisense to IGF-1R RNA prevents soft agar growth of several human tumor cell lines.

Apoptosis is a ubiquitous physiological process used to eliminate damaged or unwanted cells in multicellular organisms. Misregulation of apoptosis is believed to be involved in the pathogenesis of many human diseases. The failure of apoptotic cell death has been implicated in various cancers, as well as autoimmune disorders. Conversely, increased apoptosis is associated with a variety of diseases involving cell loss such as neurodegenerative disorders and AIDS. As such, regulators of apoptosis have become an important therapeutic target. It is now established that a major mode of tumor survival is escape from apoptosis. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

Inappropriately high protein kinase activity has been implicated in many diseases resulting from abnormal cellular function. This might arise either directly or indirectly by a failure of the proper control mechanisms for the kinase, related to mutation, over-expression or inappropriate activation of the enzyme; or by an over- or underproduction of cytokines or growth factors participating in the transduction of signals upstream or downstream of the kinase. In all of these instances, selective inhibition of the action of the kinase might be expected to have a beneficial effect.

IGF-1R is a transmembrane RTK that binds primarily to IGF-1 but also to IGF-II and insulin with lower affinity. Binding of IGF-1 to its receptor results in receptor oligomerization, activation of tyrosine kinase, intermolecular receptor autophosphorylation and phosphorylation of cellular substrates (major substrates are IRS1 and Shc). The ligand-activated IGF-1R induces mitogenic activity in normal cells and plays an important role in abnormal growth.

The IGF-1 pathway in human tumor development has an important role: 1) IGF-1R overexpression is frequently found in various tumors (breast, colon, lung, sarcoma) and is often associated with an aggressive phenotype. 2) High circulating IGF1 concentrations are strongly correlated with prostate, lung and breast cancer risk. Furthermore, IGF-1R is required for establishment and maintenance of the transformed phenotype in vitro and in vivo (Baserga R. *Exp. Cell. Res.*, 1999, 253, 1-6). The kinase activity of IGF-1R is essential for the transforming activity of several oncogenes: EGFR, PDGFR, SV40 T antigen, activated Ras, Raf, and v-Src. The expression of IGF-1R in normal fibroblasts induces neoplastic phenotypes, which can then form tumors in vivo. IGF-1R expression plays an important role in anchorage-independent growth. IGF-1R has also been shown to protect cells from chemotherapy-, radiation-, and cytokine-induced apoptosis. Conversely, inhibition of endogenous IGF-1R by dominant negative IGF-1R, triple helix formation or antisense expression vector has been shown to repress transforming activity in vitro and tumor growth in animal models.

Many of the tyrosine kinases, whether an RTK or non-receptor tyrosine kinase, have been found to be involved in cellular signaling pathways involved in numerous disorders, including cancer, psoriasis, fibrosis, atherosclerosis, restenosis, auto-immune disease, allergy, asthma, transplantation rejection, inflammation, thrombosis, nervous system diseases, and other hyperproliferative disorders or hyper-immune responses. It is desirable to provide novel inhibitors of kinases involved in mediating or maintaining disease states to treat such diseases.

The identification of effective small compounds that specifically inhibit signal transduction and cellular proliferation, by modulating the activity of receptor and non-receptor tyrosine and serine/threonine kinases, to regulate and modulate abnormal or inappropriate cell proliferation, differentiation, or metabolism is therefore desirable. In particular, the identification of methods and compounds that specifically inhibit the function of a tyrosine kinase essential for angiogenic processes or for the formation of vascular hyperpermeability leading to edema, ascites, effusions, exudates, macromolecular extravasation, matrix deposition, and their associated disorders would be beneficial.

It has been recognized that inhibitors of protein-tyrosine kinases are useful as selective inhibitors of the growth of mammalian cancer cells. For example, Gleevec™ (also known as imatinib mesylate, or ST1571), a 2-phenylpyrimidine tyrosine kinase inhibitor that inhibits the kinase activity of the BCR-ABL fusion gene product, was recently approved by the U.S. Food and Drug Administration for the treatment of CML. This compound, in addition to inhibiting BCR-ABL kinase, also inhibits KIT kinase and PDGF receptor kinase, although it is not effective against all mutant isoforms of KIT kinase. In recent clinical studies on the use of Gleevec™ to treat patients with GIST, a disease in which KIT kinase is involved in transformation of the cells, many of the patients showed marked clinical improvement. Other kinase inhibitors show even greater selectively. For example, the 4-anilinoquinazoline compound Tarceva™ inhibits only EGF receptor kinase with high potency, although it can inhibit the signal transduction of other receptor kinases, probably because such receptors heterodimerize with the EGF receptor.

In view of the importance of PTKs to the control, regulation, and modulation of cell proliferation and the diseases and disorders associated with abnormal cell proliferation, many attempts have been made to identify small molecule tyrosine kinase inhibitors. Bis-, mono-cyclic, bicyclic or heterocyclic aryl compounds (International Patent Publication No. WO 92/20642) and vinylene-azaindole derivatives (International Patent Publication No. WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0566266 A1; Expert Opin. Ther. Pat. (1998), 8(4): 475-478), selenoindoles and selenides (International Patent Publication No. WO 94/03427), tricyclic polyhydroxylic compounds (International Patent Publication No. WO 92/21660) and benzylphosphonic acid compounds (International Patent Publication No. WO 91/15495) have been described as compounds for use as tyrosine kinase inhibitors for use in the treatment of cancer. Anilinocinnolines (PCT WO97/34876) and quinazoline derivative compounds (International Patent Publication No. WO 97/22596; International Patent Publication No. WO97/42187) have been described as inhibitors of angiogenesis and vascular permeability. Bis(indolylmaleimide) compounds have been described as inhibiting particular PKC serine/threonine kinase isoforms whose signal transducing function is associated with altered vascular permeability in VEGF-related diseases (International Patent Publication Nos. WO 97/40830 and WO 97/40831).

International Patent Publication Nos. WO 03/018021 and WO 03/018022 describe pyrimidines for treating IGF-1R related disorders, International Patent Publication Nos. WO 02/102804 and WO 02/102805 describe cyclolignans and cyclolignans as IGF-1R inhibitors, International Patent Publication No. WO 02/092599 describes pyrrolopyrimidines for the treatment of a disease which responds to an inhibition of the IGF-1R tyrosine kinase, International Patent Publication No. WO 01/72751 describes pyrrolopyrimidines as tyrosine kinase inhibitors. International Patent Publication No. WO 00/71129 describes pyrrolotriazine inhibitors of kinases. International Patent Publication No. WO 97/28161 describes pyrrolo[2,3-d]pyrimidines and their use as tyrosine kinase inhibitors.

Parrizas, et al. describes tyrphostins with in vitro and in vivo IGF-1R inhibitory activity (Endocrinology, 138:1427-1433 (1997)), and International Patent Publication No. WO 00/35455 describes heteroaryl-aryl ureas as IGF-1R inhibitors. International Patent Publication No. WO 03/048133 describes pyrimidine derivatives as modulators of IGF-1R. International Patent Publication No. WO 03/024967 describes chemical compounds with inhibitory effects towards kinase proteins. International Patent Publication No. WO 03/068265 describes methods and compositions for treating hyperproliferative conditions. International Patent Publication No. WO 00/17203 describes pyrrolopyrimidines as protein kinase inhibitors. Japanese Patent Publication No. JP 07/133,280 describes a cephem compound, its production and antimicrobial composition. A. Albert et al., Journal of the Chemical Society, 11: 1540-1547 (1970) describes pteridine studies and pteridines unsubstituted in the 4-position, a synthesis from pyrazines via 3,4-dhydropteridines. A. Albert et al., Chem. Biol. Pteridines Proc. Int. Symp., 4th, 4: 1-5 (1969) describes a synthesis of pteridines (unsubstituted in the 4-position) from pyrazines, via 3-4-dihydropteridines.

IGF-1R performs important roles in cell division, development, and metabolism, and in its activated state, plays a role in oncogenesis and suppression of apoptosis. IGF-1R is known to be overexpressed in a number of cancer cell lines (IGF-1R overexpression is linked to acromegaly and to cancer of the prostate). By contrast, down-regulation of IGF-1R expression has been shown to result in the inhibition of tumorigenesis and an increased apoptosis of tumor cells.

It has been shown that high levels of dysregulated mTOR activity are associated with variety of human cancers and several hamartoma syndromes, including tuberous sclerosis complex, the PTEN-related hamartoma syndromes and Peutz-Jeghers syndrome. Although rapamycin analogues are in clinical development for cancer as mTOR kinase inhibitor, the clinical out come with CC1-779 is just modest in breast and renal cancer patients. This is probably because rapamycin partially inhibits mTOR function through raptor-mTOR complex (mTORC1). It has been also found that $\frac{2}{3}$ of the breast cancer and $\frac{1}{2}$ of renal cancer patients are resistant to rapamycin therapy. With a recent discovery of rictor-mTOR complex (mTORC2) which is involved in phosphorylation of AKT (S473) that is important in regulation of cell survival and modulation of PKCα that plays a major role in regulation of actin cytoskeletal organization in a rapamycin-independent manner, and inhibition of these activities of mTOR is probably important for broader antitumor activity and better efficacy. Therefore, it is desirable to develop novel compounds that are direct inhibitors of mTOR kinase, which would inhibit mTORC1 and mTORC2.

Rapamycin, a macrolide antibiotic has been shown to specifically inhibit mTOR kinase activity in vitro and in vivo in several studies. Although precise mechanism by which rapamycin inhibits mTOR function is not well understood, it is known that rapamycin first binds to FKBP12 (FK506 binding protein) and then binds to FRB domain of mTOR and thus inhibit mTOR activity by inducing conformational changes, which inhibits substrate binding. Rapamycin has been widely used as a specific mTOR inhibitor in preclinical studies to demonstrate role of mTOR in signal transduction and cancer. But rapamycin was not developed as a cancer therapy because of stability and solubility problems even though significant antitumor activity was observed in the NCI screening programme. However, synthesis of rapamycin analogues with superior solubility and stability properties has led to run the clinical trails with CC1-779, RAD00 and AP23573. The most advanced rapamycin analogue, CC1-779 has shown modest anti-tumor activity in Phase II breast, renal carcinoma and mantle cell lymphoma clinical trials.

The Tor genes were originally identified in yeast as the targets of the drug rapamycin. The structurally and functionally conserved mammalian counter part of yeast TOR, mTOR was later discovered. mTOR is a member of the phosphoinositide kinase-related kinase (PIKK) family, but rather than phosphorylating phosphoinositides, phosphorylates proteins on serine or threonine residues. Genetic studies have shown that mTOR is essential for cell growth and development in fruit flies, nematodes and mammals, and the disruption of the genes encoding mTOR results in lethality in all species. Several studies have demonstrated that mTOR has a central role in controlling cell growth, proliferation and metabolism. mTOR regulates a wide range of cellular functions, including translation, transcription, mRNA turnover, protein stability, actin cytoskeletal organization and autophagy. There are two mTOR complexes in mammalian cells. mTOR complex I (mTORC1) is a raptor-mTOR complex, which mainly regulates cell growth in a rapamycin-sensitive manner whereas mTOR complex II (mTORC2) is a rictor-mTOR complex, which regulates cytoskeletal organization in a rapamycin-insensitive manner.

The best-characterized function of mTOR in mammalian cells is regulation of translation. Ribosomal S6 kinase (S6K) and eukaryotic initiation factor 4E binding protein 1 (4E-BP1), the most extensively studied substrates of mTOR, are key regulators of protein translation. S6K is the major ribosomal protein kinase in mammalian cells. Phosphorylation of S6 protein by S6K selectively increases the translation of mRNAs containing a tract of pyrimidines motif; these mRNAs often encode ribosomal proteins and other translational regulators. Thus, S6K enhances overall translation capacity of cells. 4E-BP1, another well-characterized mTOR target, acts as a translational repressor by binding and inhibiting the eukaryotic translation initiation factor 4E (eIF4E), which recognizes the 5' end cap of eukaryotic mRNAs. Phosphorylation of 4E-BP1 by mTOR results in a dissociation of 4E-BP1 from eIF4E, thereby relieving the inhibition of 4E-BP1 on eIF4E-dependent translation initiation. eIF4E overexpression enhances cell growth and transforms cells by increasing the translation of a subset of key growth-promoting proteins, including cyclin D1, c-Myc and VEGF. Therefore, mTOR-dependent regulation of both 4E-BP1 and S6K might be one mechanism by which mTOR positively regulates cell growth. mTOR integrates two of the most important extracellular and intracellular signals involved in the regulation of cell growth: growth factors and nutrients. Growth factor, such as insulin or IGF1 and nutrients, such as amino acids or glucose, enhance mTOR function, as evidenced by an increased phosphorylation of S6K and 4E-BP1. Rapamycin or dominant negative mTOR inhibits these effects, indicating that mTOR integrates the regulation of signals from growth factors and nutrients.

Signalling pathways that are upstream and downstream of mTOR are often deregulated in variety of cancers, including breast, lung, kidney, prostate, blood, liver, ovarian, thyroid, GI tract and lymphoma. Oncogenes including overexpressed receptor tyrosine kinases and constitutively activated mutant receptors activate PI3K-mediated signaling pathways. Additional alterations of the PI3K-mTOR pathway in human cancers include amplification of the p110 catalytic subunit of PI3K, loss of PTEN phosphatase function, amplification of AKT2, mutations in TSC1 or TSC2, and overexpression or amplification of eIF4E or S6K1. Mutation or loss of heterozygosity in TSC1 and TSc2 most often give rise to Tuberous Sclerosis (TSC) syndrome. TSC is rarely associated with malignant tumors, although patients with TSC are at risk for malignant renal cancer of clear-cell histology. Although inactivation of TSC might not lead to malignancy per se, deregulation of this pathway seems crucial for angiogenesis in developing malignancies. TSC2 regulates VEGF production through mTOR-dependent and -independent manner.

With the recent discovery of rapamycin independent function of mTOR (by mTOR2) in phosphorylation AKT (at S473) that is important in regulation of cell survival and modulation of PKCα, which plays a major role in regulation of actin cytoskeletal organization, it is believed that inhibition of mTOR function by rapamycin is partial. Therefore, discovery of a direct mTOR kinase inhibitor, which would completely inhibit the function of both mTORC1 and mTORC2, is required for broader anti-tumor activity and better efficacy. Here we describe the discovery of direct mTOR kinase inhibitors, which can be used in the treatment of variety of cancers—including breast, lung, kidney, prostate, blood, liver, ovarian, thyroid, GI tract and lymphoma—and other indications such as rheumatoid arthritis, hamartoma syndromes, transplant rejection, IBD, multiple sclerosis and immunosuppression.

Recent success of Tarceva™, an EGFR kinase inhibitor for the treatment of NSCLC and prior success with Gleevec™ for the treatment of CML indicate that it is possible to develop selective kinase inhibitors for the effective treatment of cancers. Although there are several anti-cancer agents including kinase inhibitors, there is still continuing need for improved anti-cancer drugs, and it would be desirable to develop new compounds with better selectivity, potency or with reduced toxicity or side effects.

Thus, it is desirable to develop compounds that exhibit mTOR inhibition in order to treat cancer patients. Further, such compounds may be active in other kinases such as, for example, PI3K, Src, KDR, to add efficacy in breast, non-small cell lung cancer (NSCLC), renal cell carcinoma, mantle cell lymphoma, endometrial cancers, or other hamartoma syndromes.

Although the anticancer compounds described above have made a significant contribution to the art, there is a continuing need in this field of art to improve anticancer pharmaceuticals with better selectivity or potency, reduced toxicity, or fewer side effects.

SUMMARY OF THE INVENTION

The present invention relates to compounds of Formula I:

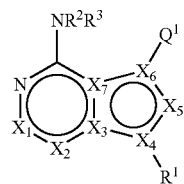

I or a pharmaceutically acceptable salt thereof. The compounds of Formula I inhibit kinase enzymes and are useful for the treatment and/or prevention of hyperproliferative diseases such as cancer, inflammation, psoriasis, allergy/asthma, disease and conditions of the immune system, disease and conditions of the central nervous system.

DETAILED DESCRIPTION OF THE INVENTION

The present invention relates to a compound of Formula I:

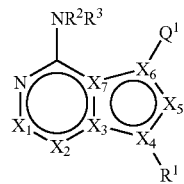

I or a pharmaceutically acceptable salt thereof, wherein:

$R^1$ is —$OR^4$, —$NR^4R^5$, —$C(=O)R^4$, —$CO_2R^4$, —$CONR^4R^5$, —$NO_2$, —$CN$, —$S(O)_{j1}R^4$, —$SO_2NR^4R^5$, —$NR^4C(=O)R^5$, —$NR^4C(=O)OR^5$, —$NR^4C(=O)NR^5R^{5a}$, —$NR^4S(O)_{j1}R^5$, —$C(=S)OR^4$, —$C(=O)SR^4$, —$NR^4C(=NR^5)NR^{4a}R^{5a}$, —$NR^4C(=NR^5)OR^{4a}$, —$NR^4C(=NR^5)SR^4$, —$OC(=O)OR^5$, —$OC(=O)NR^4R^5$, —$OC(=O)SR^4$, —$SC(=O)OR^4$, or —$SC(=O)NR^4R^5$;

$R^2$ and $R^3$ are each independently $C_{0-10}$alkyl, cyclo$C_{3-10}$alkyl, bicyclo$C_{5-10}$alkyl, aryl, heteroaryl, aralkyl, heteroaralkyl, heterocyclyl, heterobicyclo$C_{5-10}$alkyl, spiroalkyl, or heterospiroalkyl, any of which is optionally substituted by one or more independent $G^1$ substituents;

$X_1$, and $X_2$ are each independently N or —$C$-$E^1$;

$X_5$ is N, —$C$-$E^1$, or —$N$-$(E^1)_{aa}$;

$X_3$, $X_4$, $X_6$, and $X_7$ are each independently —$N$-$(E^1)_{aa}$ or C;

wherein at least one of $X_3$, $X_4$, $X_5$, $X_6$, and $X_7$ is —$N$-$(E^1)_{aa}$;

$Q^1$ is halo, —$CF_3$, —$OCF_3$, —$OR^{66}$, —$NR^{66}R^{77}(R^{66a})_{j11}$, —$C(=O)R^{66}$, —$CO_2R^{66}$, —$CONR^{66}R^{77}$, —$NO_2$, —$CN$, —$S(O)_{j11}R^{66}$, —$SO_2NR^{66}R^{77}$, —$NR^{66}C(=O)R^{77}$, —$NR^{66}C(=O)OR^{77}$, —$NR^{66}C(=O)NR^{77}R^{66a}$, —$NR^{66}S(O)_{j11}R^{77}$, —$C(=S)OR^{66}$, —$C(=O)SR^{66}$, —$NR^{66}C(=NR^{77})NR^{66a}R^{77a}$, —$NR^{66}C(=NR^{77})OR^{66a}$, —$NR^{66}C(=NR^{77})SR^{66a}$, —$OC(=O)OR^{66}$, —$OC(=O)NR^{66}R^{77}$, —$OC(=O)SR^{66}$, —$SC(=O)OR^{66}$, —$SC(=O)NR^{66}R^{77}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted with one or more independent $G^{11}$ substituents;

or $Q^1$ is any one of the following

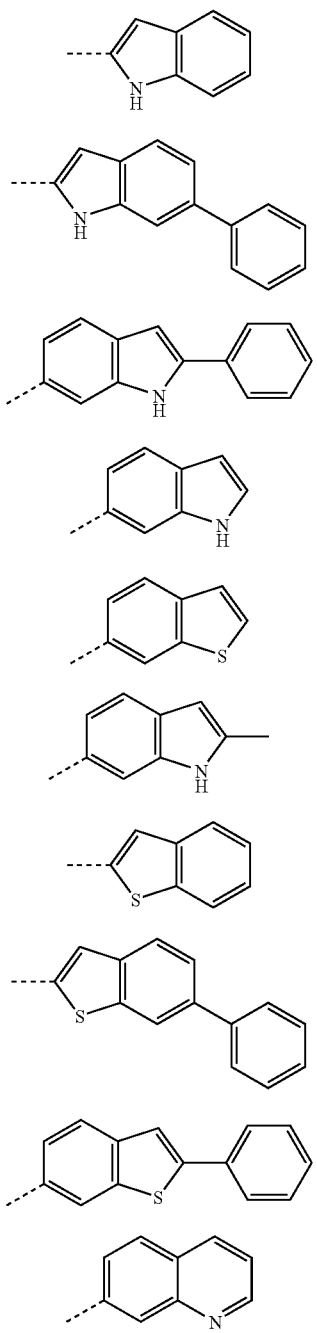

-continued
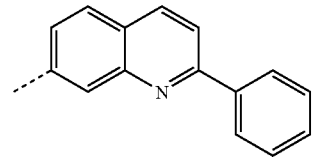
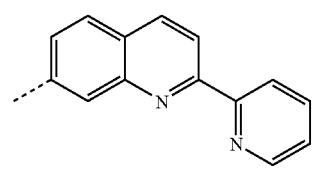
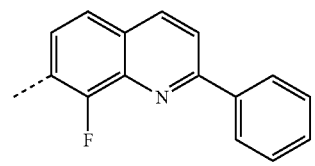
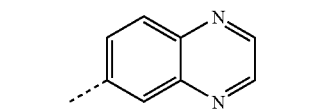
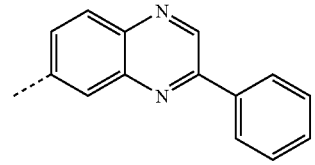
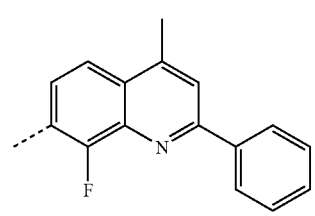
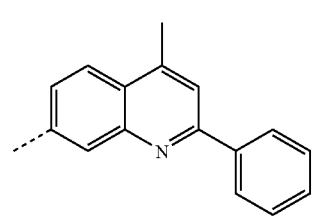
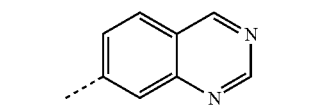
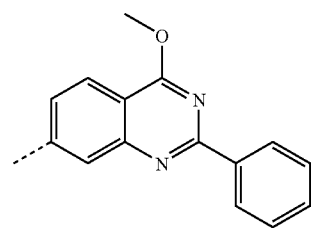
-continued
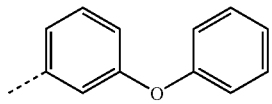
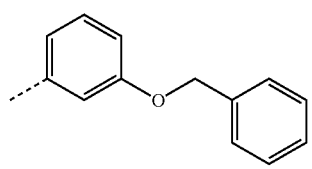
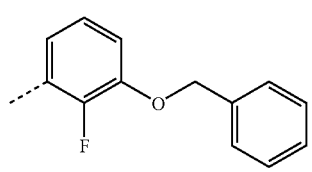
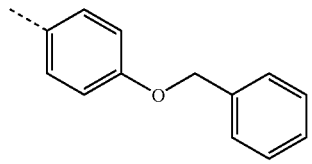
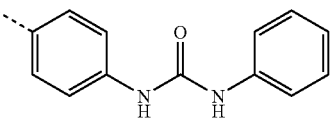
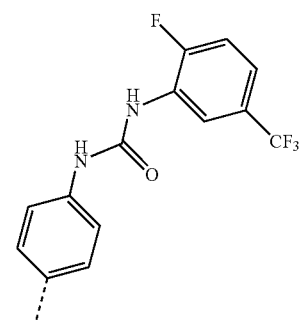
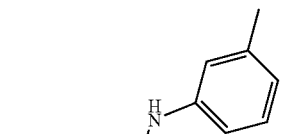
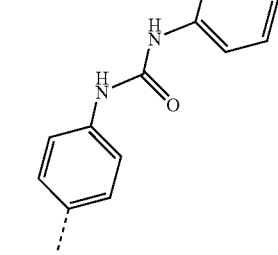

-continued

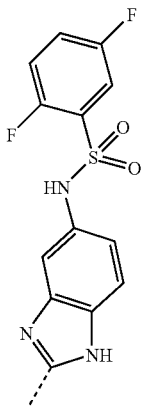
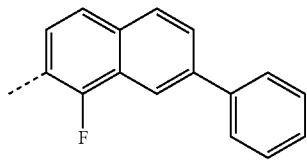
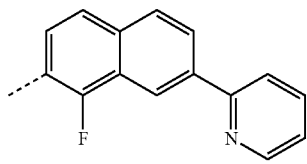
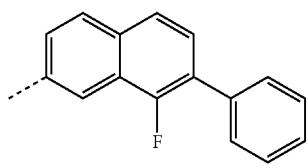
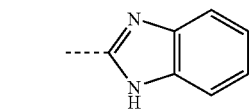
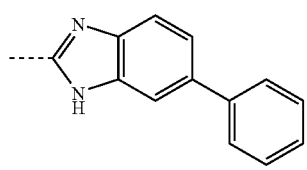
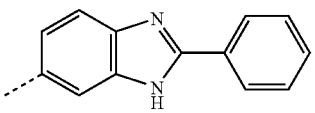
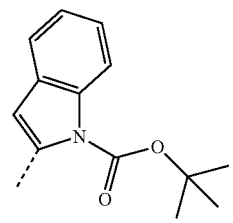

any of which is optionally substituted with one or more independent $G^{11}$ substituents;

$E^1$, $G^1$, and $G^{11}$ are each independently halo, $-CF_3$, $-OCF_3$, $-OR^6$, $-NR^6R^7(R^{6a})_{j1}$, $-C(=O)R^6$, $-CO_2R^6$, $-CONR^6R^7$, $-NO_2$, $-CN$, $-S(O)_{j1}R^6$, $-SO_2NR^6R^7$, $-NR^6C(=O)R^7$, $-NR^6C(=O)OR^7$, $-NR^6C(=O)NR^7R^{6a}$, $-NR^6S(O)_{j1}R^7$, $-C(=S)OR^6$, $-C(=O)SR^6$, $-NR^6C(=NR^7)NR^{6a}R^{7a}$, $-NR^6C(=NR^7)OR^{6a}$, $-NR^6C(=NR^7)SR^{6a}$, $-OC(=O)OR^6$, $-OC(=O)NR^6R^7$, $-OC(=O)SR^6$, $-SC(=O)OR^6$, $-SC(=O)NR^6R^7$, $C_{0-10}$alkyl, $C_{2-10}$alkenyl, $C_{2-10}$alkynyl, $C_{1-10}$alkoxyC$_{1-10}$alkyl, $C_{1-10}$alkoxyC$_{2-10}$alkenyl, $C_{1-10}$alkoxyC$_{2-10}$alkynyl, $C_{1-10}$alkylthioC$_{1-10}$alkyl, $C_{1-10}$alkylthioC$_{2-10}$alkenyl, $C_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, heterocyclyl-C$_{2-10}$alkynyl, aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, oxo, $-CF_3$, $-OCF_3$, $-OR^{222}$, $-NR^{222}R^{333}(R^{222a})_{j1a}$, $-C(=O)R^{222}$, $-CO_2R^{222}$, $-C(=O)NR^{222}R^{333}$, $-NO_2$, $-CN$, $S(=O)_{j1a}R^{222}$, $-SO_2NR^{222}R^{333}$, $NR^{222}C(=O)R^{33}$, $-NR^{222}C(=O)OR^{333}$, $-NR^{222}C(=O)NR^{333}R^{222a}$, $-NR^{222}S(O)_j R^{333}$, $-C(=S)OR^{222}$, $-C(=O)SR^{222}$, $-NR^{222}C(=NR^{333})NR^{222a}R^{333a}$, $-NR^{222}C(=NR^{333})OR^{222}$, $-NR^{222}C(=NR^{333})SR^{222a}$, $-OC(=O)OR^{222}$, $-OC(=O)NR^{222}R^{333}$, $-OC(=O)SR^{222}$, $-SC(=O)OR^{222}$, or $-SC(=O)NR^{222}R^{333}$ substituents;

$R^4$, $R^{4a}$, $R^5$, $R^{5a}$, $R^6$, $R^{6a}$, $R^7$, $R^{7a}$, $R^{66}$, $R^{66a}$, $R^{77}$, $R^{77a}$, $R^{222}$, $R^{222a}$, $R^{333}$, and $R^{333a}$ are each independently $C_{0-10}$alkyl, $C_{2-10}$alkenyl, $C_{2-10}$alkynyl, $C_{1-10}$alkoxyC$_{1-10}$alkyl, $C_{1-10}$alkoxyC$_{2-10}$alkenyl, $C_{1-10}$alkoxyC$_{2-10}$alkynyl, $C_{1-10}$alkylthioC$_{1-10}$alkyl, $C_{1-10}$alkylthioC$_{2-10}$alkenyl, $C_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, heterocyclyl-C$_{2-10}$alkynyl, aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted by one or more independent $G^{111}$ substituents;

or in the case of $-NR^4R^5$, $-NR^5R^{5a}$, $-NR^{4a}R^{5a}$, $-NR^6R^7(R^{6a})_{j1}$, $-NR^{6a}R^{7a}$, $-NR^7R^{6a}$, $-NR^{66}R^{77}(R^{66a})_{j1}$, $-NR^{77}R^{66a}$, $-NR^{66a}R^{77a}$, $-NR^{222}R^{333}(R^{222a})_{j1a}$, $-NR^{333}R^{222a}$, $-NR^{222a}R^{333a}$, $NR^{77b}R^{87}$, $-NR^{78}R^{87}$, or $-NR^{78}R^{88}$, then $R^4$ and $R^5$, or $R^5$ and $R^{5a}$, or $R^{4a}$ and $R^{5a}$, or $R^6$ and $R^7$, or $R^{6a}$ and $R^{7a}$, or $R^7$ and $R^{6a}$, or $R^{66}$ and $R^{77}$, or $R^{77}$ and $R^{66a}$, or $R^{66a}$ and $R^{77a}$, or $R^{222}$ and $R^{333}$, or $R^{333}$ and $R^{222a}$, or $R^{222a}$ and $R^{333a}$, or $R^{77b}$ and $R^{87}$, or $R^{78}$ and $R^{87}$, or $R^{78}$ and $R^{88}$, respectfully, are optionally taken together with the nitrogen atom to which they are attached to form a 3-10 membered saturated or unsaturated ring, wherein said ring is optionally substituted by one or more independent $G^{1111}$ substituents and wherein said ring optionally includes one or more heteroatoms other than the nitrogen to which $R^4$ and $R^5$, or $R^5$ and $R^{5a}$, or $R^{4a}$ and $R^{5a}$, or $R^6$ and $R^7$, or $R^{6a}$ and $R^{7a}$, or $R^7$ and $R^{6a}$, or $R^{66}$ and $R^{77}$, or $R^{77}$ and $R^{66a}$, or $R^{66a}$ and $R^{77a}$, or $R^{222}$ and $R^{333}$, or $R^{333}$ and $R^{222a}$, or $R^{222a}$ and $R^{333a}$, or $R^{77b}$ and $R^{87}$, or $R^{78}$ and $R^{87}$, or $R^{78}$ and $R^{88}$ are attached;

$G^{111}$ and $G^{1111}$ are each independently $C_{0-10}$alkyl, $C_{2-10}$alkenyl, $C_{2-10}$alkynyl, $C_{1-10}$alkoxyC$_{1-10}$alkyl, $C_{1-10}$alkoxyC$_{2-10}$alkenyl, $C_{1-10}$alkoxyC$_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted with one or more independent halo, —$CF_3$, —$OCF_3$, —$OR^{77b}$, —$NR^{77b}R^{87}$, —$C(O)R^{77b}$, —$CO_2R^{77b}$, —$CONR^{77b}R^{87}$, —$NO_2$, —$CN$, —$S(O)_{j5a}R^{77b}$, —$SO_2NR^{77b}R^{87}$, —$NR^{77b}C(=O)R^{87}$, —$NR^{77b}C(=O)OR^{87}$, —$NR^{77b}C(=O)NR^{78}R^{87}$, —$NR^{77b}S(O)_{j5a}R^{87}$, —$C(=S)OR^{77b}$, —$C(=O)SR^{77b}$, —$NR^{77b}C(=NR^{87})NR^{78}R^{88}$, —$NR^{77b}C(=NR^{87})OR^{78}$, —$NR^{77b}C(=NR^{87})SR^{78}$, —$OC(=O)OR^{77b}$, —$OC(=O)NR^{77b}R^{87}$, —$OC(=O)SR^{77b}$, —$SC(=O)OR^{77b}$, —$P(O)OR^{77b}OR^{87}$, or —$SC(=O)NR^{77b}R^{87}$ substituents;

$R^{77b}$, $R^{87}$, and $R^{88}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2N(C_{0-4}$alkyl$)(C_{0-4}$alkyl$)$, or —$N(C_{0-4}$alkyl$)(C_{0-4}$alkyl$)$ substituents;

or $R^{77b}$, $R^{87}$, and $R^{88}$ are each independently aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, hetaryl-$C_{2-10}$alkynyl, mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —$N(C_{1-6}$alkyl)-$C_{1-6}$alkyl-aryl, any of which is optionally substituted with one or more independent halo, cyano, nitro, —$O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CON(C_{0-4}$alkyl$)(C_{0-10}$alkyl), —$SO_2N(C_{0-4}$alkyl$)(C_{0-4}$alkyl$)$, or —$N(C_{0-4}$alkyl$)(C_{0-4}$alkyl$)$ substituents;

$j_1$, $j_{1a}$, $j_{11}$, and $j_{5a}$ are each independently 0, 1, or 2; and aa is 0, or 1.

In an aspect of the present invention, a compound is represented by Formula I, or a pharmaceutically acceptable salt thereof, wherein $X_3$ is N; $X_1$, $X_2$, and $X_5$ are C-$E^1$; $X_4$, $X_6$, and $X_7$ are C; and the other variables are described as above for Formula I.

In a second aspect of the present invention, a compound is represented by Formula I, or a pharmaceutically acceptable salt thereof, wherein $X_4$ is N; $X_1$, $X_2$, and $X_5$ are C-$E^1$; and $X_3$, $X_6$, and $X_7$ are C; and the other variables are described as above for Formula I.

In a third aspect of the present invention, a compound is represented by Formula I, or a salt thereof, wherein $X_5$ is N-$(E^1)_{aa}$; $X_1$ and $X_2$ are C-$E^1$; $X_3$, $X_4$, $X_6$, and $X_7$ are C; and the other variables are described as above for Formula I.

In a fourth aspect of the present invention, a compound is represented by Formula I, or a salt thereof, wherein $X_6$ is N; $X_1$, $X_2$, and $X_5$ are C-$E^1$; $X_3$, $X_4$, and $X_7$ are C; and the other variables are described as above for Formula I.

In a fifth aspect of the present invention, a compound is represented by Formula I, or a salt thereof, wherein $X_7$ is N; $X_1$, $X_2$, and $X_5$ are C-$E^1$; $X_3$, $X_4$, and $X_6$ are C; and the other variables are described as above for Formula I.

In a sixth aspect of the present invention, a compound is represented by Formula I, or a salt thereof, wherein $X_1$ and $X_3$ are N; $X_2$ and $X_5$ are C-$E^1$; $X_4$, $X_6$, and $X_7$ are C; and the other variables are described as above for Formula I.

In a seventh aspect of the present invention, a compound is represented by Formula I, or a salt thereof, wherein $X_1$ and $X_4$ are N; $X_2$ and $X_5$ are C-$E^1$; $X_3$, $X_6$, and $X_7$ are C; and the other variables are described as above for Formula I.

In an eighth aspect of the present invention, a compound is represented by Formula I, or a salt thereof, wherein $X_1$ is N; $X_5$ is N-$(E^1)_{aa}$; $X_2$ is C-$E^1$; $X_3$, $X_4$, $X_6$, and $X_7$ are C; and the other variables are described as above for Formula I.

In a ninth aspect of the present invention, a compound is represented by Formula I, or a salt thereof, wherein $X_1$ and $X_6$ are N; $X_2$ and $X_5$ are C-$E^1$; $X_3$, $X_4$, and $X_7$ are C; and the other variables are described as above for Formula I.

In a tenth aspect of the present invention, a compound is represented by Formula I, or a salt thereof, wherein $X_1$ and $X_7$ are N; $X_2$ and $X_5$ are C-$E^1$; $X_3$, $X_4$, and $X_6$ are C; and the other variables are described as above for Formula I.

In a eleventh aspect of the present invention, a compound is represented by Formula I, or a salt thereof, wherein $X_2$ and $X_3$ are N; $X_1$ and $X_5$ are C-$E^1$; $X_4$, $X_6$, and $X_7$ are C; and the other variables are described as above for Formula I.

In a twelfth aspect of the present invention, a compound is represented by Formula I, or a salt thereof, wherein $X_2$ and $X_4$ are N; $X_1$ and $X_5$ are C-$E^1$; $X_3$, $X_6$, and $X_7$ are C; and the other variables are described as above for Formula I.

In a thirteenth aspect of the present invention, a compound is represented by Formula I, or a salt thereof, wherein $X_2$ is N; $X_5$ is N-$(E^1)_{aa}$, $X_1$ is C-$E^1$; $X_3$, $X_4$, $X_6$, and $X_7$ are C; and the other variables are described as above for Formula I.

In a fourteenth aspect of the present invention, a compound is represented by Formula I, or a salt thereof, wherein $X_2$ and $X_6$ are N; $X_1$ and $X_5$ are C-$E^1$; $X_3$, $X_4$, and $X_7$ are C; and the other variables are described as above for Formula I.

In a fifteenth aspect of the present invention, a compound is represented by Formula I, or a salt thereof, wherein $X_2$ and $X_7$ are N; $X_1$ and $X_5$ are C-$E^1$; $X_3$, $X_4$, and $X_6$ are C; and the other variables are described as above for Formula I.

In a sixteenth aspect of the present invention, a compound is represented by Formula I, or a salt thereof, wherein $X_3$ and $X_4$ are N; $X_1$, $X_2$, and $X_5$ are C-$E^1$; $X_6$ and $X_7$ are C; $R^1$ is absent; and the other variables are described as above for Formula I.

In a seventeenth aspect of the present invention, a compound is represented by Formula I, or a salt thereof, wherein $X_3$ and $X_5$ are N; $X_1$ and $X_2$ are C-$E^1$; $X_4$, $X_6$, and $X_7$ are C; and the other variables are described as above for Formula I.

In an eighteenth aspect of the present invention, a compound is represented by Formula I, or a salt thereof, wherein $X_4$ and $X_5$ are N; $X_1$ and $X_2$ are C-$E^1$; $X_3$, $X_6$, and $X_7$ are C; and the other variables are described as above for Formula I.

In a nineteenth aspect of the present invention, a compound is represented by Formula I, or a salt thereof, wherein $X_4$ and $X_6$ are N; $X_1$, $X_2$, and $X_5$ are C-$E^1$; $X_3$ and $X_7$ are C; $R^1$ is absent; and the other variables are described as above for Formula I.

In a twentieth aspect of the present invention, a compound is represented by Formula I, or a salt thereof, wherein $X_4$ and $X_7$ are N; $X_1$, $X_2$, and $X_5$ are C-$E^1$; $X_3$ and $X_6$ are C; $R^1$ is absent; and the other variables are described as above for Formula I.

In a twenty-first aspect of the present invention, a compound is represented by Formula I, or a salt thereof, wherein $X_5$ and $X_6$ are N; $X_1$ and $X_2$ are C-$E^1$; $X_3$, $X_4$, and $X_7$ are C; and the other variables are described as above for Formula I.

In a twenty-second aspect of the present invention, a compound is represented by Formula I, or a salt thereof, wherein $X_5$ and $X_7$ are N; $X_1$ and $X_2$ are C-$E^1$; $X_3$, $X_4$, and $X_6$ are C; and the other variables are described as above for Formula I.

In a twenty-third aspect of the present invention, a compound is represented by Formula I, or a salt thereof, wherein $X_2$, $X_3$, and $X_4$ are N; $X_1$ and $X_5$ are C-$E^1$; $X_6$ and $X_7$ are C; $R^1$ is absent; and the other variables are described as above for Formula I.

In a twenty-fourth aspect of the present invention, a compound is represented by Formula I, or a salt thereof, wherein $X_2$, $X_3$, and $X_5$ are N; $X_1$ is C-$E^1$; $X_4$, $X_6$ and $X_7$ are C; and the other variables are described as above for Formula I.

In a twenty-fifth aspect of the present invention, a compound is represented by Formula I, or a salt thereof, wherein $X_3$, $X_4$, and $X_5$ are N; $X_1$ and $X_2$ are C-$E^1$; $X_6$ and $X_7$ are C; $R^1$ is absent; and the other variables are described as above for Formula I.

In a twenty-sixth aspect of the present invention, a compound is represented by Formula I, or a salt thereof, wherein $X_1$, $X_3$, and $X_4$ are N; $X_2$ and $X_5$ are C-$E^1$; $X_6$ and $X_7$ are C; $R^1$ is absent; and the other variables are described as above for Formula I.

In a twenty-seventh aspect of the present invention, a compound is represented by Formula I, or a salt thereof, wherein $X_1$, $X_4$, and $X_5$ are N; $X_2$ is C-$E^1$; $X_3$, $X_6$ and $X_7$ are C; and the other variables are described as above for Formula I.

In a twenty-eighth aspect of the present invention, a compound is represented by Formula I, or a salt thereof, wherein $X_2$, $X_4$, and $X_5$ are N; $X_1$ is C-$E^1$; $X_3$, $X_6$ and $X_7$ are C; and the other variables are described as above for Formula I.

In a twenty-ninth aspect of the present invention, a compound is represented by Formula I, or a salt thereof, wherein $X_1$, $X_5$, and $X_6$ are N; $X_2$ is C-$E^1$; $X_3$, $X_4$, and $X_7$ are C; and the other variables are described as above for Formula I.

In a thirtieth aspect of the present invention, a compound is represented by Formula I, or a salt thereof, wherein $X_2$, $X_5$, and $X_6$ are N; $X_1$ is C-$E^1$; $X_3$, $X_4$, and $X_7$ are C; and the other variables are described as above for Formula I.

In a thirty-first aspect of the present invention, a compound is represented by Formula I, or a salt thereof, wherein $X_4$, $X_5$, and $X_6$ are N; $X_1$ and $X_2$ are C-$E^1$; $X_3$ and $X_7$ are C; $R^1$ is absent; and the other variables are described as above for Formula I.

In a thirty-second aspect of the present invention, a compound is represented by Formula I, or a salt thereof, wherein $X_1$, $X_3$, and $X_5$ are N; $X_2$ is C-$E^1$; $X_4$, $X_6$ and $X_7$ are C; and the other variables are described as above for Formula I.

In a thirty-third aspect of the present invention, a compound is represented by Formula I, or a salt thereof, wherein $X_1$, $X_4$, and $X_6$ are N; $X_2$ and $X_5$ are C-$E^1$; $X_3$ and $X_7$ are C; $R^1$ is absent; and the other variables are described as above for Formula I.

In a thirty-fourth aspect of the present invention, a compound is represented by Formula I, or a salt thereof, wherein $X_1$, $X_5$, and $X_7$ are N; $X_2$ is C-$E^1$; $X_3$, $X_4$, and $X_6$ are C; and the other variables are described as above for Formula I.

In a thirty-fifth aspect of the present invention, a compound is represented by Formula I, or a salt thereof, wherein $X_1$, $X_4$, and $X_7$ are N; $X_2$ and $X_5$ are C-$E^1$; $X_3$ and $X_6$ are C; $R^1$ is absent; and the other variables are described as above for Formula I.

In a thirty-sixth aspect of the present invention, a compound is represented by Formula I, or a salt thereof, wherein $X_2$, $X_4$, and $X_6$ are N; $X_1$ and $X_5$ are C-$E^1$; $X_3$ and $X_7$ are C; $R^1$ is absent; and the other variables are described as above for Formula I.

In a thirty-seventh aspect of the present invention, a compound is represented by Formula I, or a salt thereof, wherein $X_2$, $X_4$, and $X_7$ are N; $X_1$ and $X_5$ are C-$E^1$; $X_3$ and $X_6$ are C; $R^1$ is absent; and the other variables are described as above for Formula I.

In a thirty-eighth aspect of the present invention, a compound is represented by Formula I, or a salt thereof, wherein $X_2$, $X_5$, and $X_7$ are N; $X_1$ is C-$E^1$; $X_3$, $X_4$, and $X_6$ are C; and the other variables are described as above for Formula I.

In a thirty-ninth aspect of the present invention, a compound is represented by Formula I, or a salt thereof, wherein $X_1$, $X_4$, $X_5$, and $X_6$ are N; $X_2$ is C-$E^1$; $X_3$ and $X_7$ are C; $R^1$ is absent; and the other variables are described as above for Formula I.

In a fortieth aspect of the present invention, a compound is represented by Formula I, or a salt thereof, wherein $X_2$, $X_4$, $X_5$, and $X_6$ are N; $X_1$ is C-$E^1$; $X_3$ and $X_7$ are C; $R^1$ is absent; and the other variables are described as above for Formula I.

In a forty-first aspect of the present invention, a compound is represented by Formula I, or a salt thereof, wherein $X_1$, $X_3$, $X_4$, and $X_5$ are N; $X_2$ is C-$E^1$; $X_6$ and $X_7$ are C; $R^1$ is absent; and the other variables are described as above for Formula I.

In a forty-second aspect of the present invention, a compound is represented by Formula I, or a salt thereof, wherein $X_2$, $X_3$, $X_4$, and $X_5$ are N; $X_1$ is C-$E^1$; $X_6$ and $X_7$ are C; $R^1$ is absent; and the other variables are described as above for Formula I.

The following embodiments refer to all of the forty-two aspects above:

In an embodiment of each of the above aspects, a compound is represented by Formula I, or a pharmaceutically acceptable salt thereof, wherein $R^1$ is —$OR^4$ and the other variables are as described in each of the above aspects.

In another embodiment of each of the above aspects, a compound is represented by Formula I, or a pharmaceutically acceptable salt thereof, wherein $R^1$ is —$CONR^4R^5$ and the other variables are as described in each of the above aspects.

In yet another embodiment of each of the above aspects, a compound is represented by Formula I, or a pharmaceutically acceptable salt thereof, wherein $R^1$ is —$S(O)_{j1}R^4$ and the other variables are as described in each of the above aspects.

The compounds of the present invention include any one of
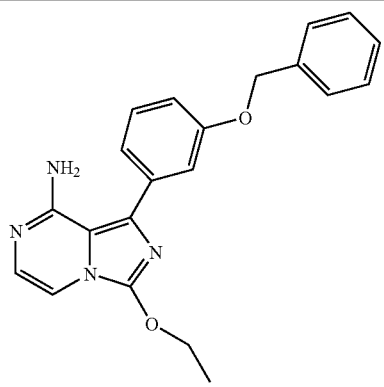
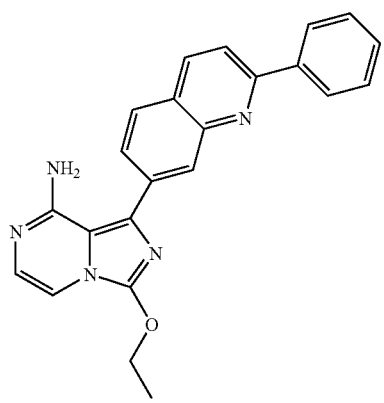
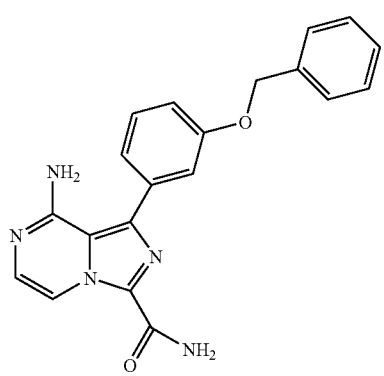
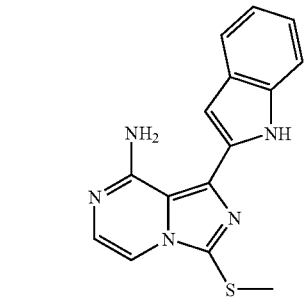
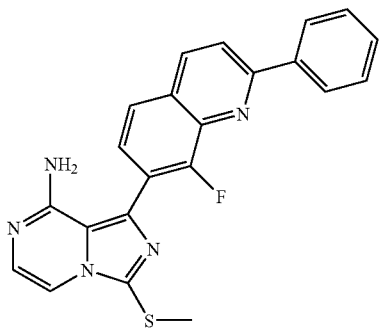
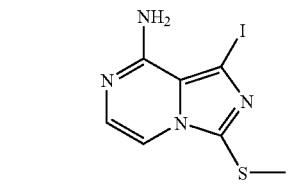
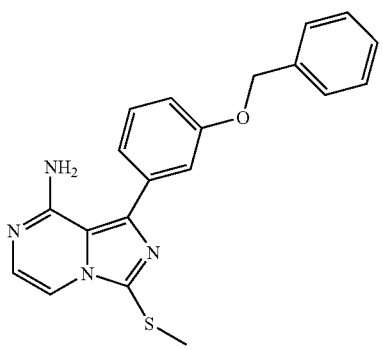
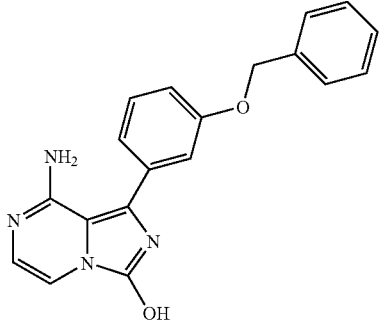
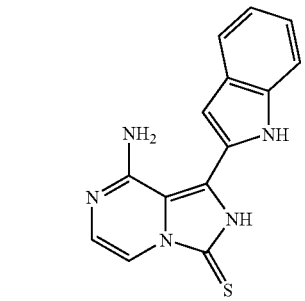

-continued
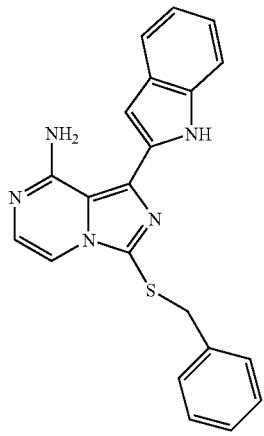
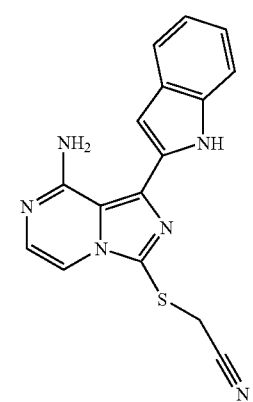
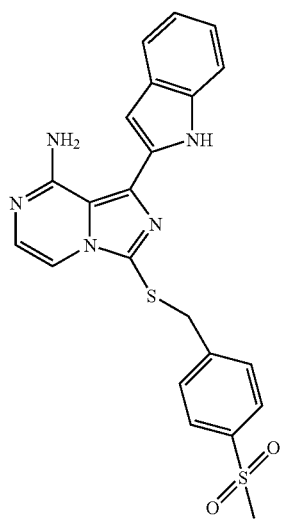
-continued
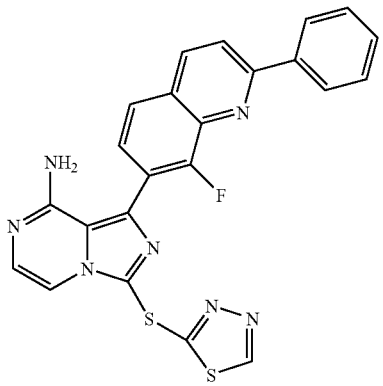
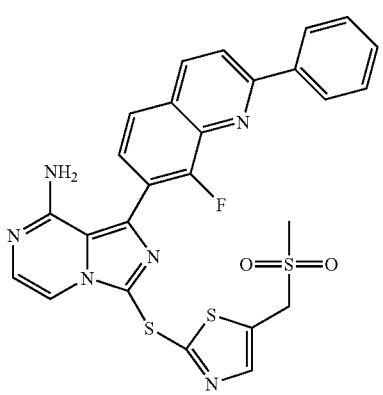
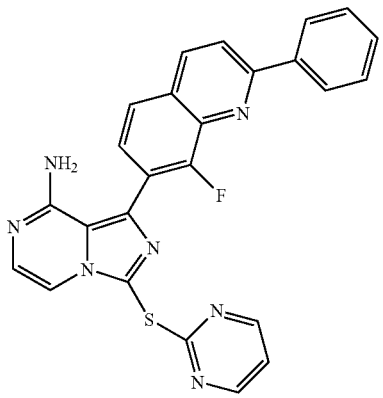
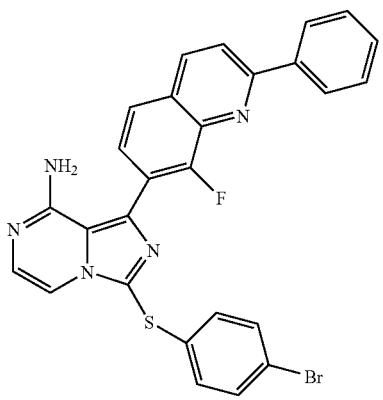

-continued
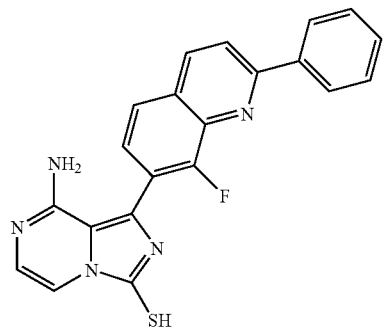
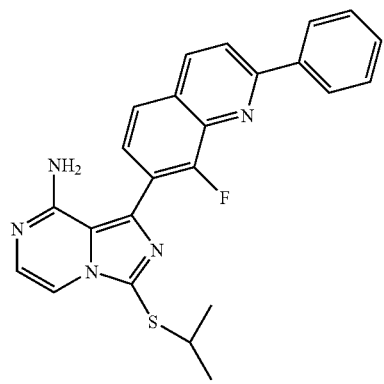
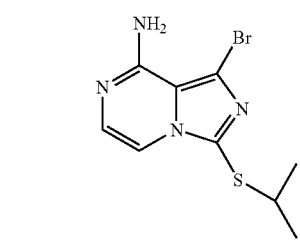
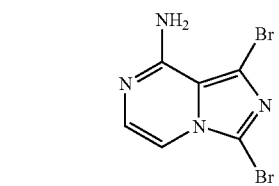
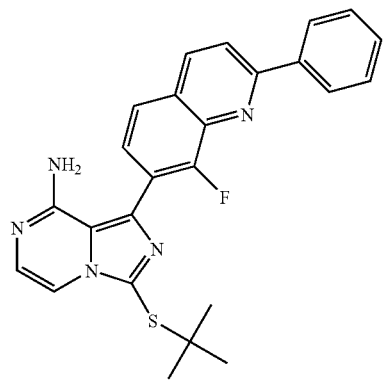
-continued
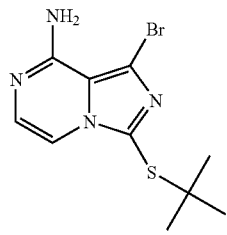
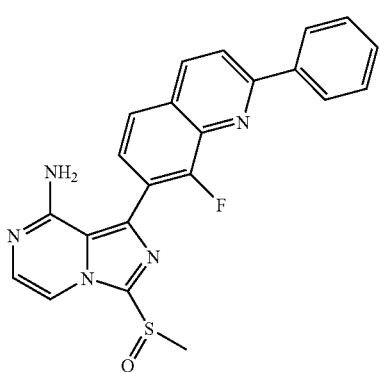
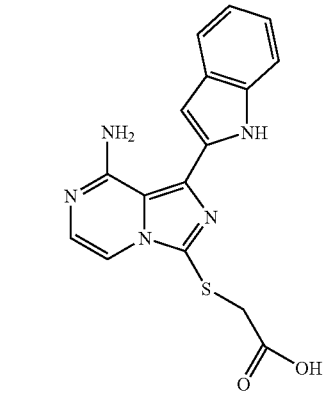
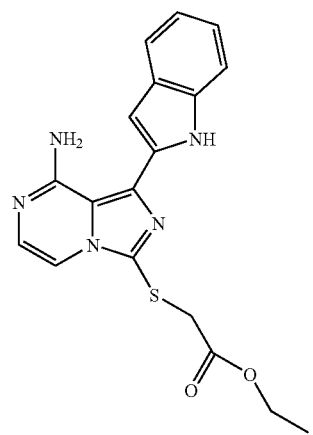

-continued
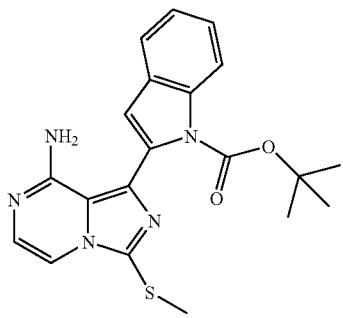
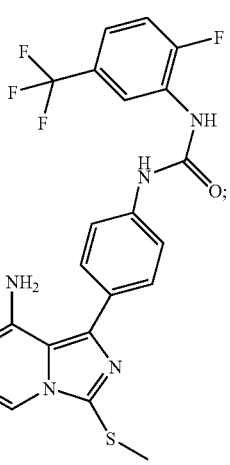
or a pharmaceutically acceptable salt thereof.
The compounds of the present invention include any one of,
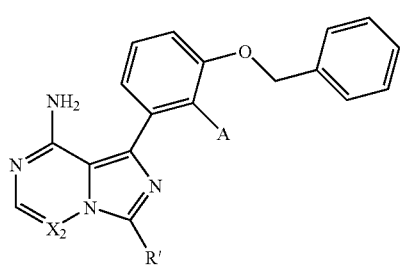
wherein $X_2$ is either N or CH, A is either H or F, $R^1$ is —$XR^a$, X is either S or O, and $XR^a$ is any one of:
$XCH_3$
XiPr
X-tBu
X—$(CH_2)_2CH_3$
X—$(CH_2)_3CH_3$
X—$(CH_2)_2OCH_3$
X—$(CH_2)_2N(CH_3)_2$
X-cyclobutyl
X-cyclopentyl
X-cyclohexyl
-continued
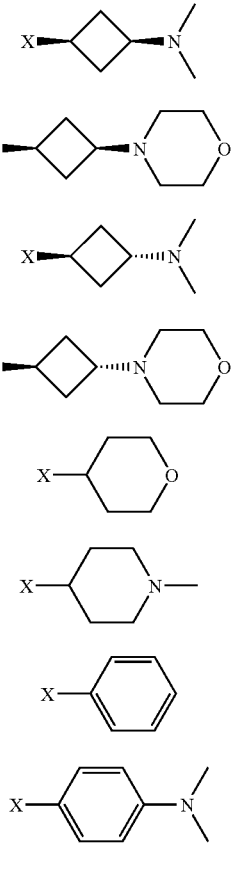
; or -continued

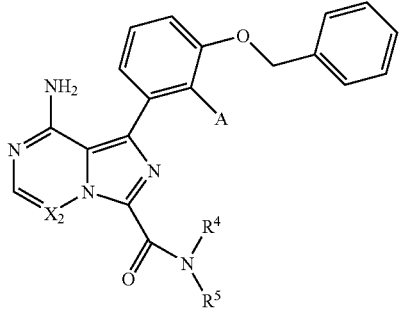

wherein $X_2$ is either N or CH, A is either H or F, and $NR^4R^5$ is any one of:

$N(CH_3)_2$
$N(CH_2CH_3)_2$
$NH(CH_3)$
$NH(CH_2CH_3)$
$NH(CH_2)_2OCH_3$
$NH(CH_2)_2N(CH_3)_2$
$N(CH_3)(CH_2)_2OCH_3$
$N(CH_3)(CH_2)_2N(CH_3)_2$
$NCH_3(CH_2CH_3)$
$NHPh$

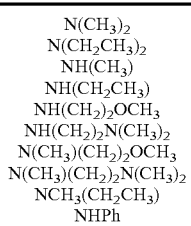

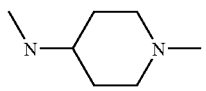

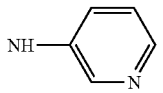

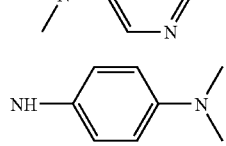

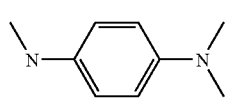

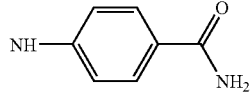

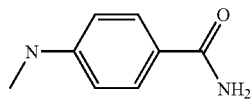

-continued

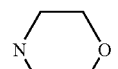

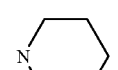

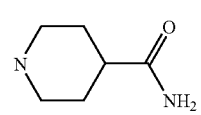

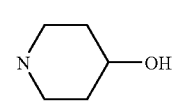

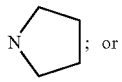; or

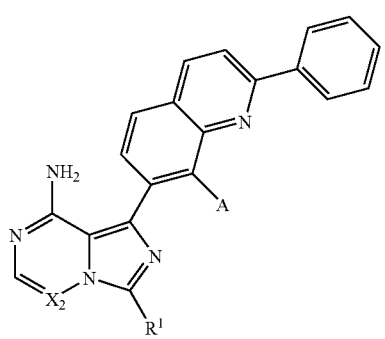

wherein $X_2$ is either N or CH, A is either H or F, $R^1$ is —$X^a$, X is either S or O, and $XR^a$ is any one of:

$XCH_3$
$XiPr$
$X$-$tBu$
$X—(CH_2)_2CH_3$
$X—(CH_2)_3CH_3$
$X—(CH_2)_2OCH_3$
$X—(CH_2)_2N(CH_3)_2$

X-cyclobutyl
X-cyclopentyl
X-cyclohexyl

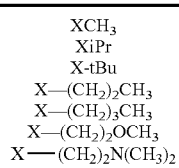

-continued
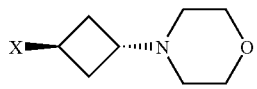
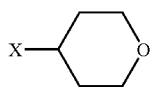
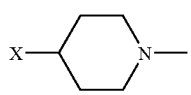
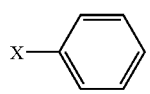
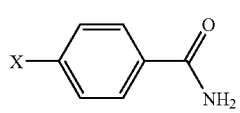
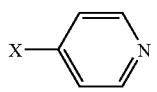
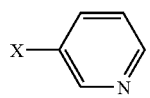
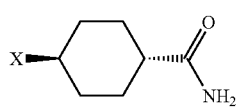
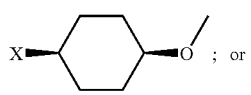
-continued
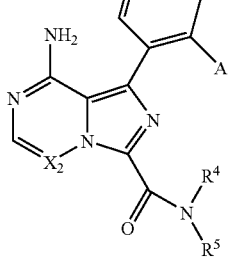
wherein $X_2$ is either N or CH, A is either H or F, and $NR^4R^5$ is any one of:
$N(CH_3)_2$
$N(CH_2CH_3)_2$
$NH(CH_3)$
$NH(CH_2CH_3)$
$NH(CH_2)_2OCH_3$
$NH(CH_2)_2N(CH_3)_2$
$N(CH_3)(CH_2)_2OCH_3$
$N(CH_3)(CH_2)_2N(CH_3)_2$
$NCH_3(CH_2CH_3)$
NHPh
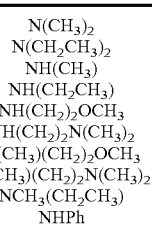
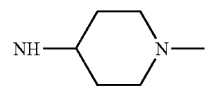
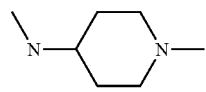
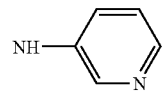
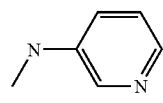
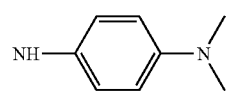
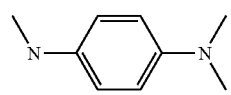
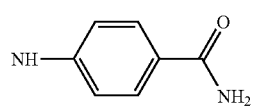
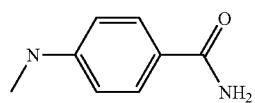

-continued
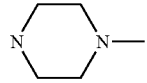
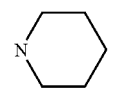
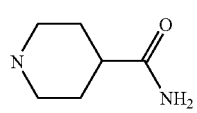
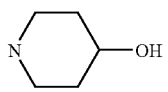
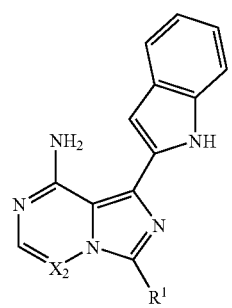
wherein $X_2$ is either N or CH, $R^1$ is —$XR^a$, X is either S or O, and $XR^a$ is any one of:
X-ethyl
XiPr
X-tBu
X—(CH$_2$)$_2$CH$_3$
X—(CH$_2$)$_3$CH$_3$
X—(CH$_2$)$_2$OCH$_3$
X—(CH$_2$)$_2$N(CH$_3$)$_2$
X-cyclobutyl
X-cyclopentyl
X-cyclohexyl
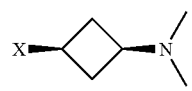
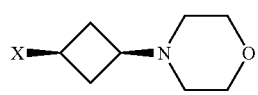
-continued
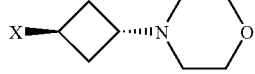
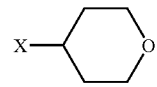
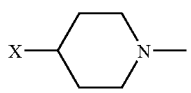
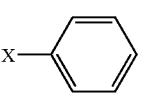
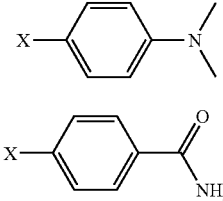
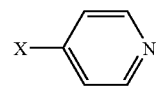
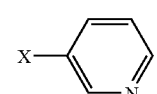
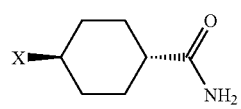
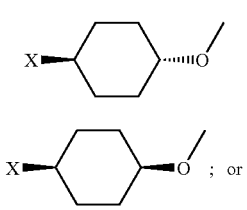
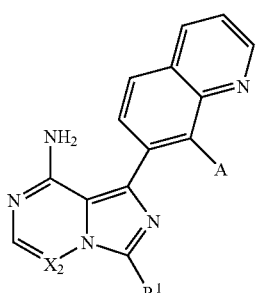
wherein $X_2$ is either N or CH, A is either H or F, $R^1$ is —$XR^a$, X is either S or O, and $XR^a$ is any one of:

XCH₃
XiPr
X-tBu
X—(CH₂)₂CH₃
X—(CH₂)₃CH₃
X—(CH₂)₂OCH₃
X—(CH₂)₂N(CH₃)₂
X-cyclobutyl
X-cyclopentyl
X-cyclohexyl
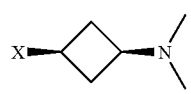
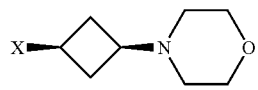
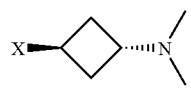
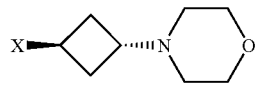
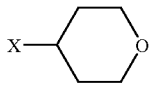
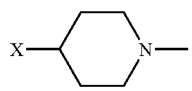
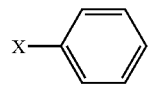
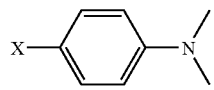
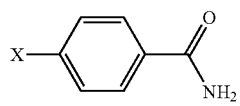
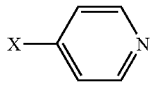
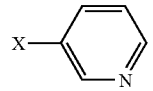
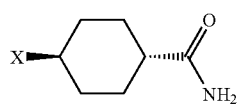
-continued
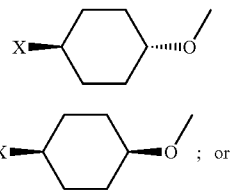
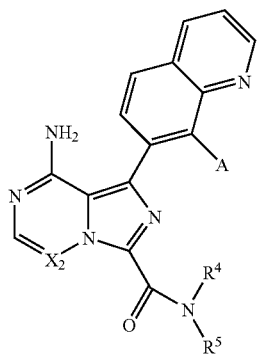
wherein $X_2$ is either N or CH, A is either H or F, and $NR^4R^5$ is any one of:
N(CH₃)₂
N(CH₂CH₃)₂
NH(CH₃)
NH(CH₂CH₃)
NH(CH₂)₂OCH₃
NH(CH₂)₂N(CH₃)₂
N(CH₃)(CH₂)₂OCH₃
N(CH₃)(CH₂)₂N(CH₃)₂
NCH₃(CH₂CH₃)
NHPh
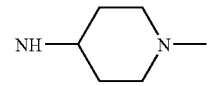
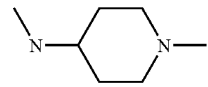
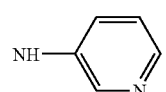
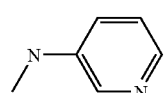
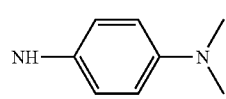

-continued
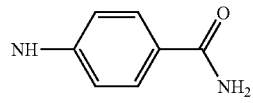
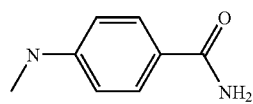
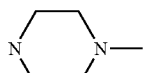
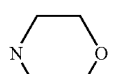
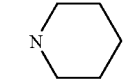
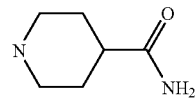
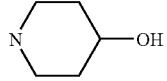
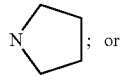
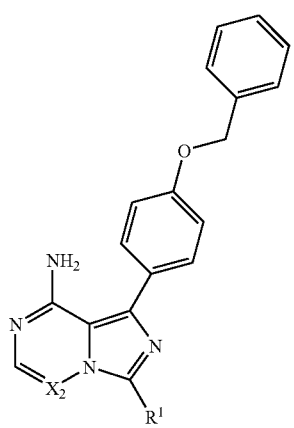
wherein $X_2$ is either N or CH, $R^1$ is —$XR^a$, X is either S or O, and $XR^a$ is any one of:
XCH$_3$
XiPr
X-tBu
X—(CH$_2$)$_2$CH$_3$
X—(CH$_2$)$_3$CH$_3$
X—(CH$_2$)$_2$OCH$_3$
X—(CH$_2$)$_2$N(CH$_3$)$_2$
X-cyclobutyl
X-cyclopentyl
-continued
X-cyclohexyl
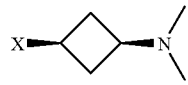
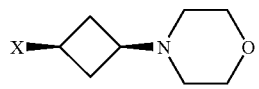
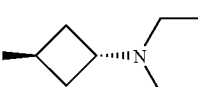
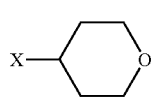
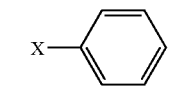
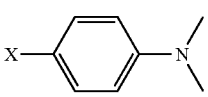
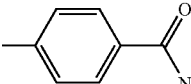
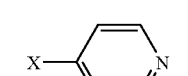
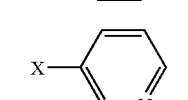
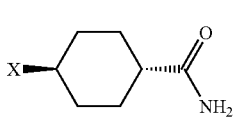
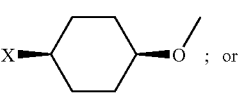

-continued
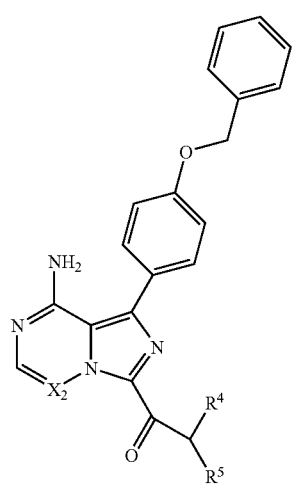
wherein $X_2$ is either N or CH, and $NR^4R^5$ is any one of:
$N(CH_3)_2$
$N(CH_2CH_3)_2$
$NH(CH_3)$
$NH(CH_2CH_3)$
$NH(CH_2)_2OCH_3$
$NH(CH_2)_2N(CH_3)_2$
$N(CH_3(CH_2)_2OCH_3$
$N(CH_3)(CH_2)_2N(CH_3)_2$
$NCH_3(CH_2CH_3)$
NHPh
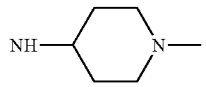
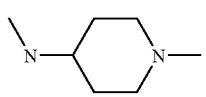
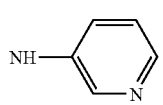
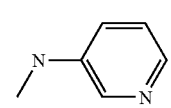
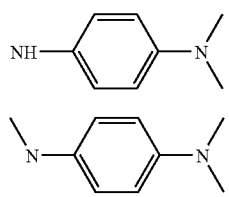
-continued
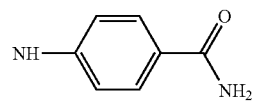
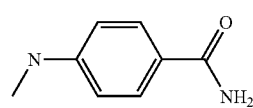
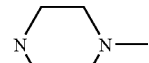
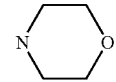
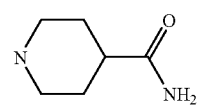
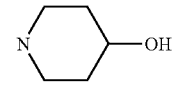
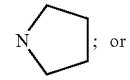 ; or
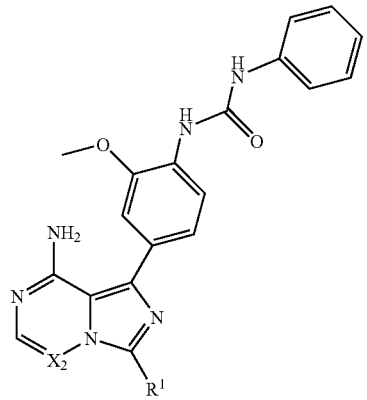
wherein $X_2$ is either N or CH, $R^1$ is —$XR^a$, X is either S or O, and $XR^a$ is any one of:
$XCH_3$
XiPr
X—tBu
X—$(CH_2)_2CH_3$
X—$(CH_2)_3CH_3$
X—$(CH_2)_2OCH_3$
X—$(CH_2)_2N(CH_3)_2$
X-cyclobutyl
X-cyclopentyl
X-cyclohexyl -continued wherein $X_2$ is either N or CH, and $NR^4R^5$ is any one of:

$N(CH_3)_2$
$N(CH_2CH_3)_2$
$NH(CH_3)$
$NH(CH_2CH_3)$
$NH(CH_2)_2OCH_3$
$NH(CH_2)_2N(CH_3)_2$
$N(CH_3)(CH_2)_2OCH_3$
$N(CH_3)(CH_2)_2N(CH_3)_2$
$NCH_3(CH_2CH_3)$
$NHPh$

-continued
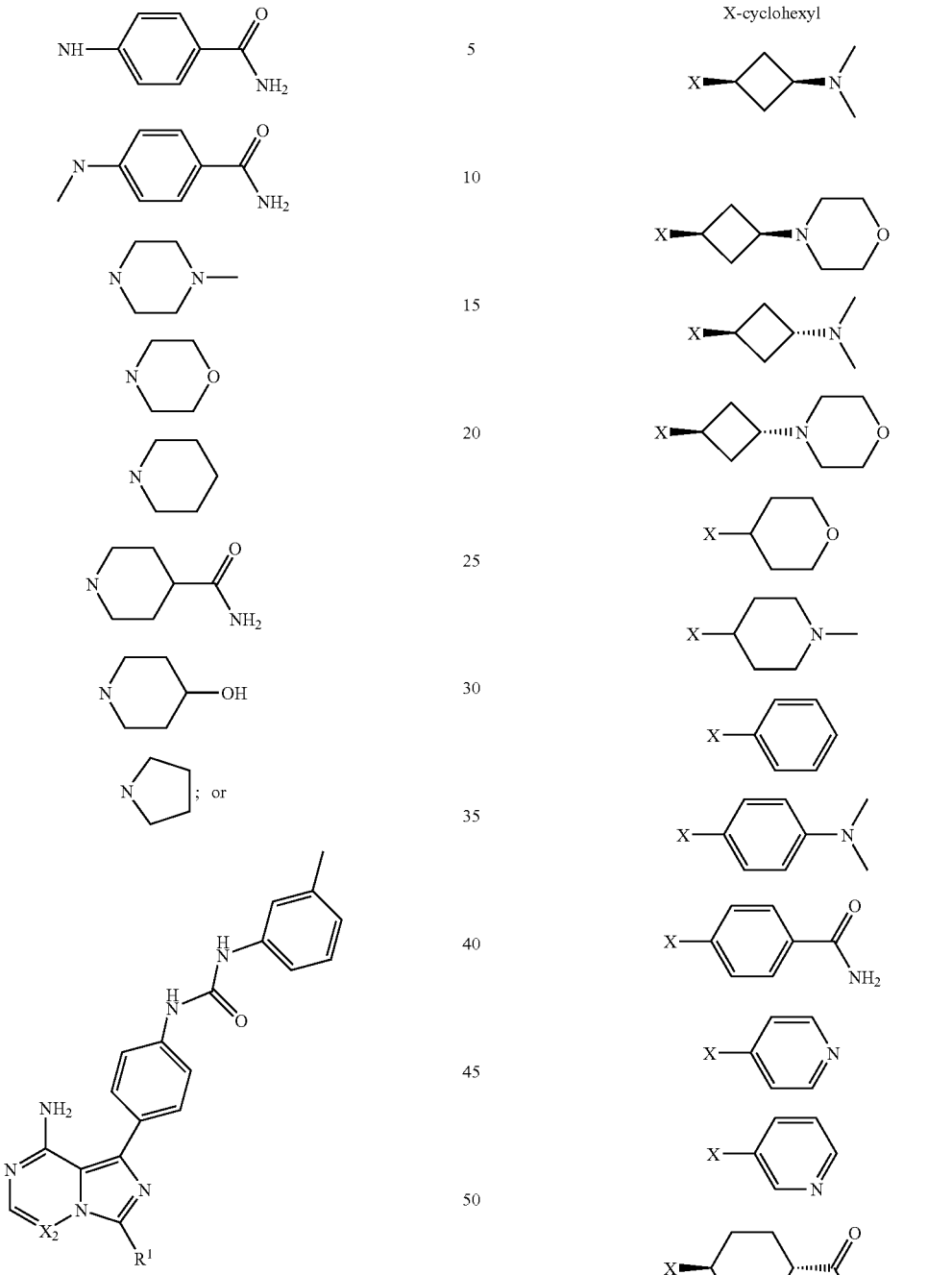
wherein $X_2$ is either N or CH, $R^1$ is —$XR^a$, X is either S or O, and $XR^a$ is any one of:
$XCH_3$
$XiPr$
$X$-$tBu$
$X$-$(CH_2)_2CH_3$
$X$—$(CH_2)_3CH_3$
$X$—$(CH_2)_2OCH_3$
$X$—$(CH_2)_2N(CH_3)_2$
$X$-cyclobutyl
$X$-cyclopentyl
-continued
$X$-cyclohexyl
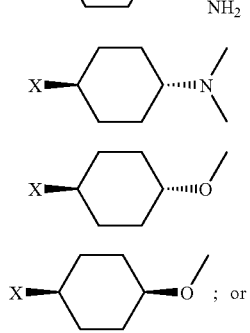

-continued
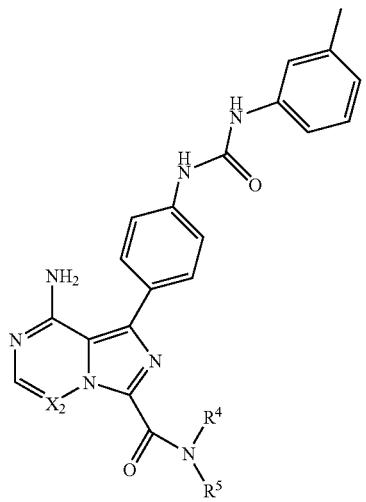
wherein X₂ is either N or CH, and NR⁴R⁵ is any one of:
N(CH₃)₂
N(CH₂CH₃)₂
NH(CH₃)
NH(CH₂CH₃)
N(CH₂)₂OCH₃
NH(CH₂)₂N(CH₃)₂
N(CH₃)(CH₂)₂OCH₃
N(CH₂CH₃)(CH₂)₂N(CH₃)₂
NCH₃)(CH₂CH₃)
NHPh
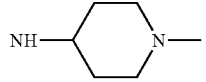
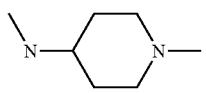
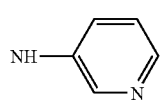
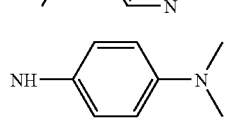
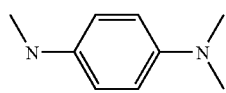
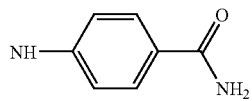
-continued
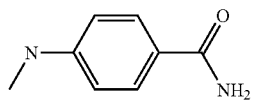
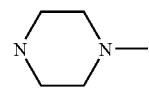
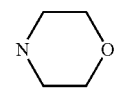
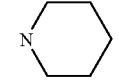
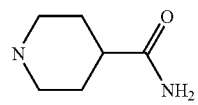
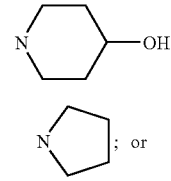
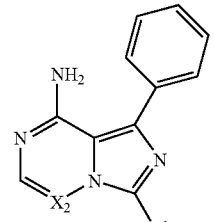; or
wherein X₂ is either N or CH, R¹ is —XRᵃ, X is either S or O, and XRᵃ is any one of:
XCH₃
XiPr
X-tBu
X—(CH₂)₂CH₃
X—(CH₂)₃CH₃
X—(CH₂)₂OCH₃
X—(CH₂)₂N(CH₃)₂
X-cyclobutyl
X-cyclopentyl
X-cyclohexyl
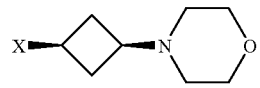

-continued
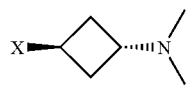
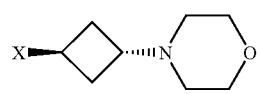
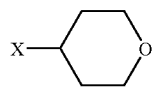
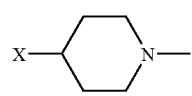
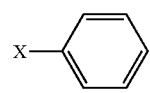
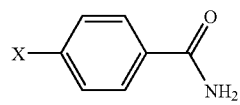
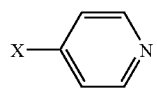
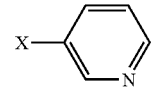
-continued
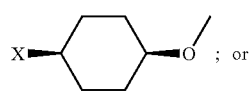
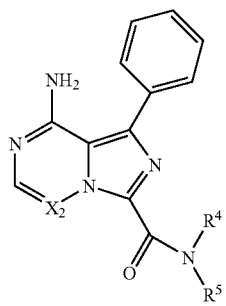
wherein $X_2$ is either N or CH, and $NR^4R^5$ is any one of:
$N(CH_3)_2$
$N(CH_2CH_3)_2$
$NH(CH_3)$
$NH(CH_2CH_3)$
$NH(CH_2)_2OCH_3$
$NH(CH_2)_2N(CH_3)_2$
$N(CH_3)(CH_2)_2OCH_3$
$N(CH_3)(CH_2)_2N(CH_3)_2$
$NCH_3(CH_2CH_3)$
$NHPh$
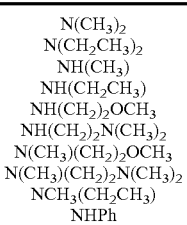
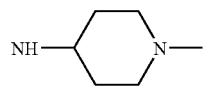
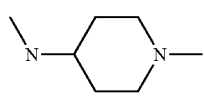
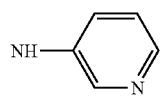
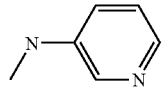
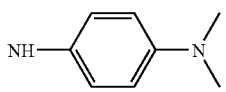
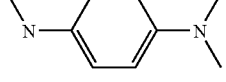
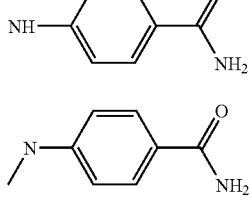

-continued
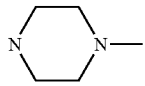
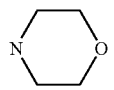
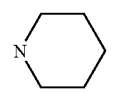
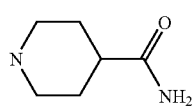
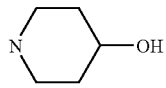
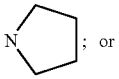 ; or
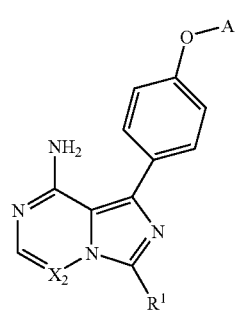
wherein $X_2$ is either N or CH, A is either H or Me, $R^1$ is —$XR^a$, X is either S or O, and $XR^a$ is any one of:
$XCH_3$
$XiPr$
$X\text{-}tBu$
$X—(CH_2)_2CH_3$
$X—(CH_2)_3CH_3$
$X—(CH_2)_2OCH_3$
$X—(CH_2)_2N(CH_3)_2$
X-cyclobutyl
X-cyclopentyl
X-cyclohexyl
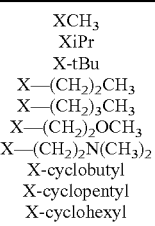
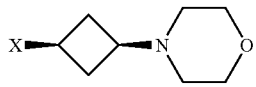
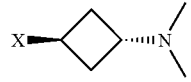
-continued
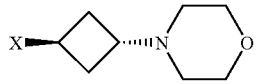
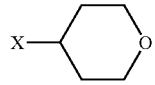
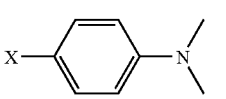
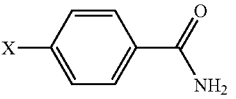
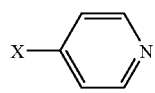
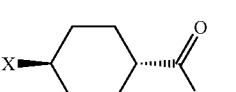
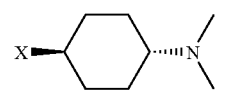
 ; or
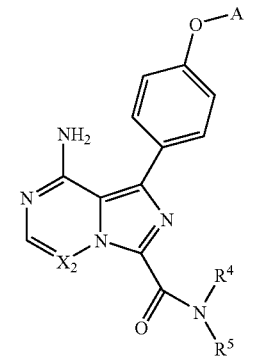

wherein X$_2$ is either N or CH, A is either H or Me, and NR$^4$R$^5$ is any one of:

N(CHhd 3)$_2$
N(CH$_2$CH$_3$)$_2$
NH(CH$_3$)
NH(CH$_2$CH$_3$)
NH(CH$_2$)$_2$OCH$_3$
NH(CH$_2$)$_2$N(CH$_3$)$_2$
N(CH$_3$)$_2$(CH$_2$)$_2$OCH$_3$
N(CH$_3$)(CH$_2$)$_2$N(CH$_3$)$_2$
NCH$_3$(CH$_2$CH$_3$)
NHPh

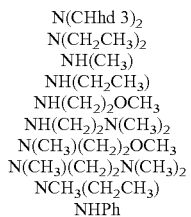
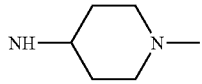
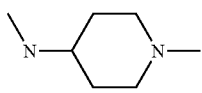
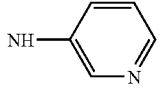
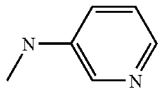
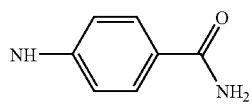
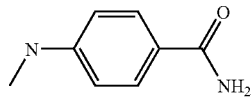
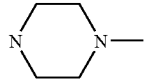
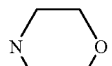
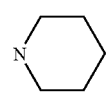
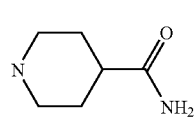

-continued

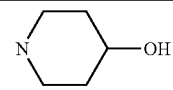
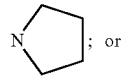; or

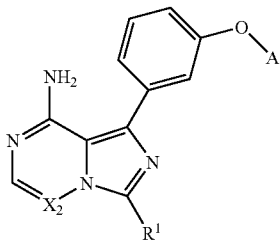

wherein X$_2$ is either N or CH, A is either H or Me, R$^1$ is —XR$^a$, X is either S or O, and XR$^a$ is any one of:

XCH$_3$
XiPr
X-tBu
X—(CH$_2$)$_2$CH$_3$
X—(CH$_2$)$_3$CH$_3$
X—(CH$_2$)$_2$OCH$_3$
X—(CH$_2$)$_2$N(CH$_3$)$_2$
X-cyclobutyl
X-cyclopentyl
X-cyclohexyl

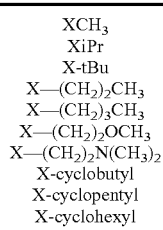
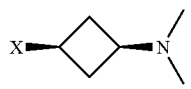
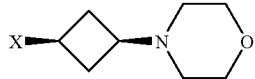
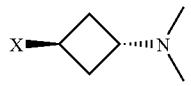
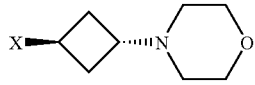
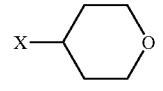
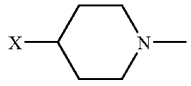
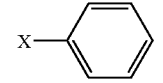

-continued
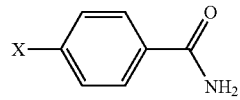
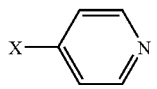
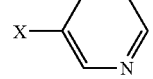
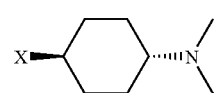
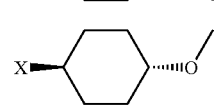
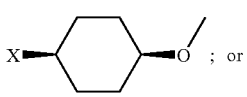
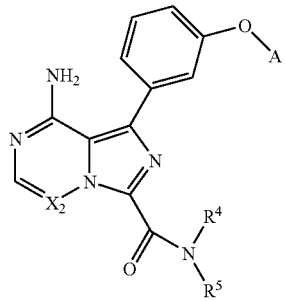
wherein X$_2$ is either N or CH, A is either H or Me, and NR$^4$R$^5$ is any one of:
N(CH$_3$)$_2$
N(CH$_2$CH$_3$)$_2$
NH(CH$_3$)
NH(CH$_2$CH$_3$)
NH(CH$_2$)$_2$OCH$_3$
NH(CH$_2$)$_2$N(CH$_3$)$_2$
N(CH$_3$)(CH$_2$)$_2$OCH$_3$
N(CH$_3$)(CH$_2$)$_2$N(CH$_3$)$_2$
NCH$_2$(CH$_2$CH$_3$)
NHPh
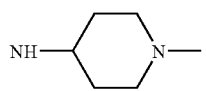
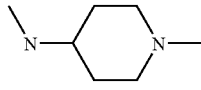
-continued
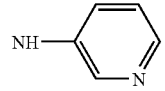
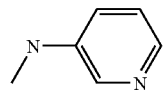
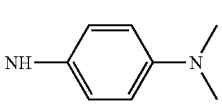
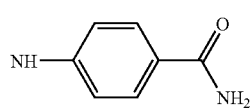
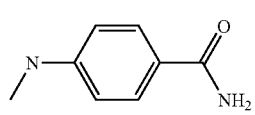
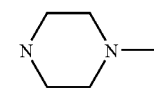
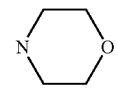
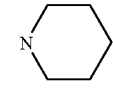
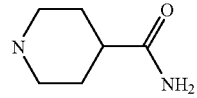
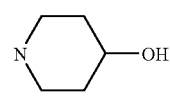
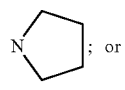

51
-continued
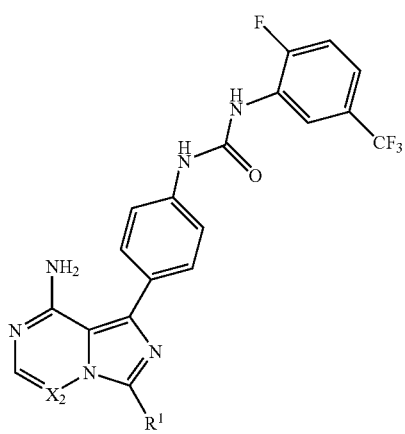
wherein $X_2$ is either N or CH, $R^1$ is —$XR^a$, X is either S or O, and $XR^a$ is any one of:
XCH₃
XiPr
X-tBu
X—(CH₂)₂CH₃
X—(CH₂)₃CH₃
X—(CH₂)₂OCH₃
X—(CH₂)₂N(CH₃)₂
X-cyclobutyl
X-cyclopentyl
X-cyclohexyl
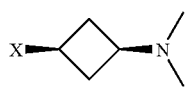
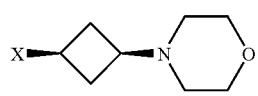
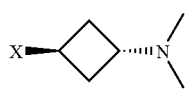
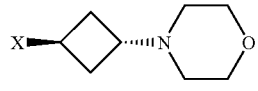
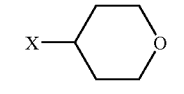
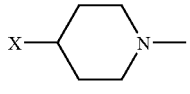
52
-continued
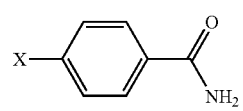
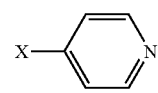
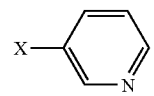
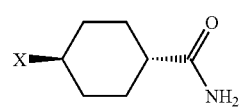
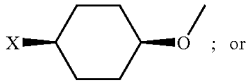
; or
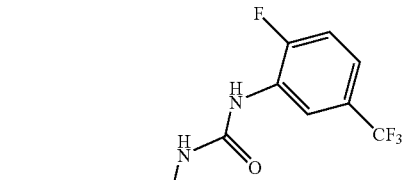
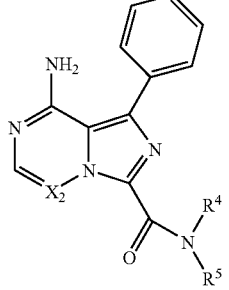

wherein $X_2$ is either N or CH, and $NR^4R^5$ is any one of:

N(CH$_3$)$_2$
N(CH$_2$CH$_3$)$_2$
NH(CH$_3$)
NH(CH$_2$CH$_3$)
NH(CH$_2$)$_2$OCH$_3$
NH(CH$_2$)$_2$N(CH$_3$)$_2$
N(CH$_3$)(CH$_2$)$_2$OCH$_3$
N(CH$_3$)(CH$_2$)$_2$N(CH$_3$)$_2$
NCH$_2$(CH$_2$CH$_3$)
NHPh

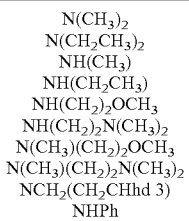
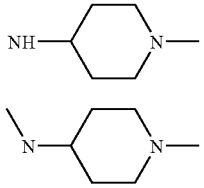
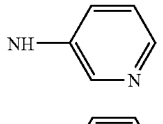
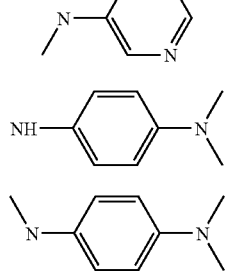
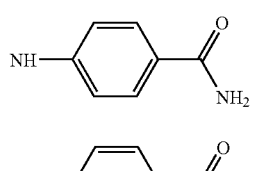
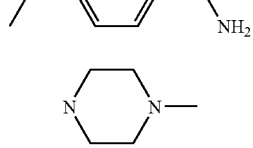
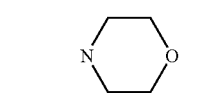
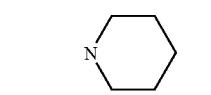
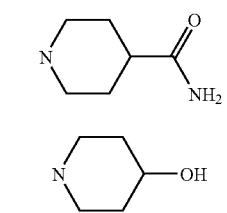

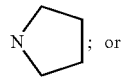

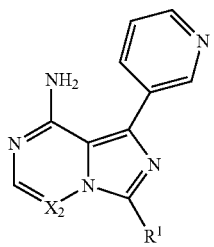

wherein $X_2$ is either N or CH, $R^1$ is —$XR^a$, X is either S or O, and $XR^a$ is any one of:

XCH$_3$
XiPr
X-tBu
X—(CH$_2$)$_2$CH$_3$
X—(CH$_2$)$_3$CH$_3$
X—(CH$_2$)$_2$OCH$_3$
X—(CH$_2$)$_2$N(CH$_3$)$_2$
X-cyclobutyl
X-cyclopentyl
X-cyclohexyl

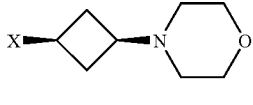
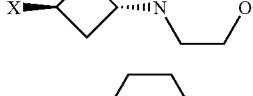
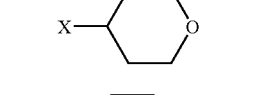
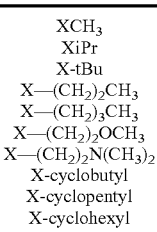
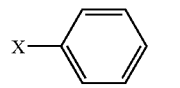
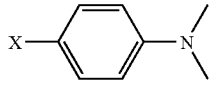

-continued

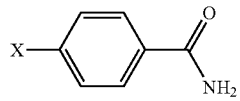

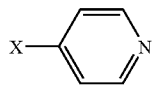

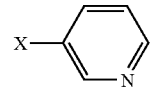

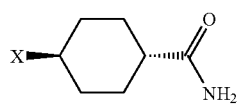

; or

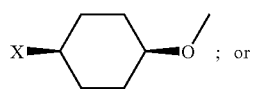

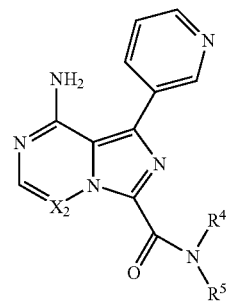

wherein $X_2$ is either N or CH, and $NR^4R^5$ is any one of:

N(CH$_3$)$_2$
N(CH$_2$CH$_3$)$_2$
NH(CH$_3$)
NH(CH$_2$CH$_3$)
NH(CH$_2$)$_2$OCH$_3$
NH(CH$_2$)$_2$N(CH$_3$)$_2$
N(CH$_3$)(CH$_2$)$_2$OCH$_3$
N(CH$_3$)(CH$_2$)$_2$N(CH$_3$)$_2$
NCH$_2$(CH$_2$CH$_3$)
NHPh

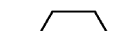

-continued (further structures including NH-pyridine, N-methylpyridine, NH-phenyl-N(CH$_3$)$_2$, N,N'-dimethyl phenylenediamine, NH-benzamide, N-methyl benzamide, N-methylpiperazine, morpholine, piperidine, piperidine-4-carboxamide, 4-hydroxypiperidine, pyrrolidine; or)

[4-amino-1-bromo-imidazo-triazine structure with $X_2$ and $R^1$]

wherein X$_2$ is either N or CH, R$^1$ is —XR$^a$, X is either S or O, and XR$^a$ is any one of:

XCH$_3$
XiPr
X-tBu
X—(CH$_2$)$_2$CH$_3$
X—(CH$_2$)$_3$CH$_3$
X—(CH$_2$)$_2$OCH$_3$
X—(CH$_2$)$_2$N(CH$_3$)$_2$
X-cyclobutyl
X-cyclopentyl
X-cyclohexyl

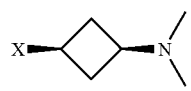

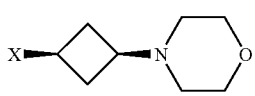

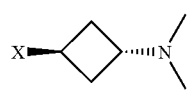

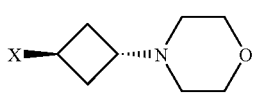

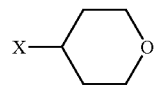

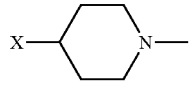

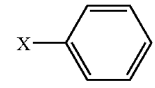

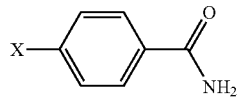

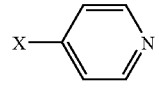

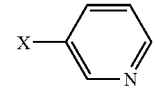

-continued

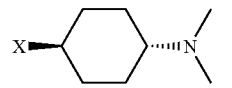

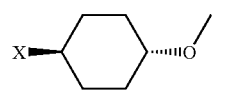

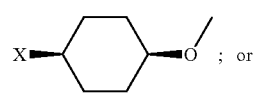

; or

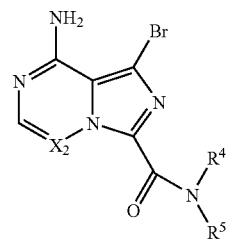

wherein X$_2$ is either N or CH, and NR$^4$R$^5$ is any one of:

N(CH$_3$)$_2$
N(CH$_2$CH$_3$)$_2$
NH(CH$_3$)
NH(CH$_2$CH$_3$)
NH(CH$_2$)$_2$OCH$_3$
NH(CH$_2$)$_2$N(CH$_3$)$_2$
N(CH$_3$)(CH$_2$)$_2$OCH$_3$
N(CH$_3$)(CH$_2$)$_2$N(CH$_3$)$_2$
NCH$_2$(CH$_2$CHhd 3)
NHPh

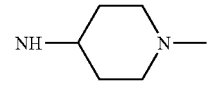

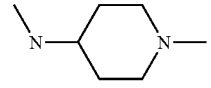

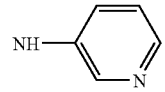

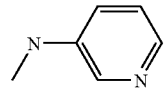

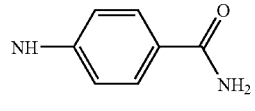

-continued
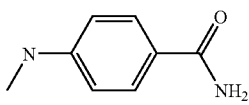
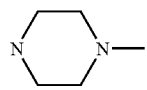
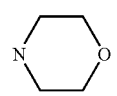
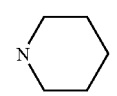
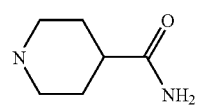
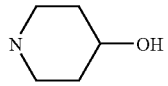
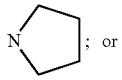 ; or
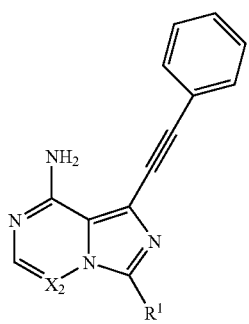
wherein $X_2$ is either N or CH, $R^1$ is —$XR^a$, X is either S or O, and $XR^a$ is any one of:
XCH₃
XiPr
X-tBu
X—(CH₂)₂CH₃
X—(CH₂)₃CH₃
X—(CH₂)₂OCH₃
X—(CH₂)₂N(CH₃)₂
X-cyclobutyl
X-cyclopentyl
-continued
X-cyclohexyl
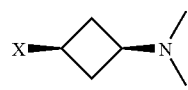
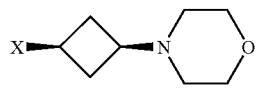
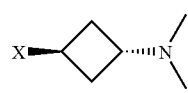
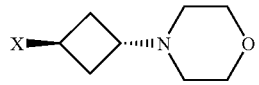
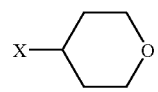
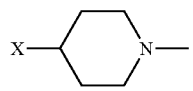
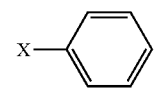
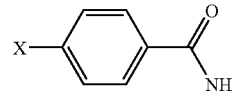
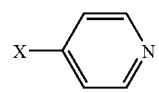
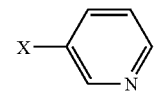
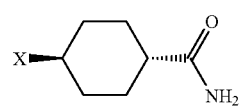
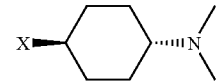

-continued
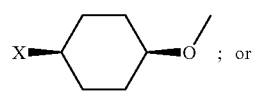 ; or
-continued
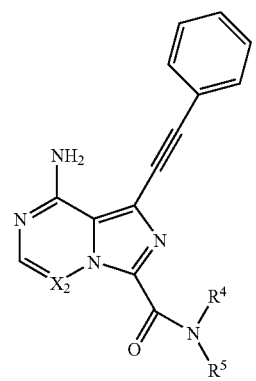
wherein $X_2$ is either N or CH, and $NR^4R^5$ is any one of:
| | | | |
|---|---|---|---|
| N(CH₃)₂ | N(CH₂CH₃)₂ | NH(CH₃) | NH(CH₂CH₃) |
| NH(CH₂)₂OCH₃ | NH(CH₂)₂N(CH₃)₂ | N(CH₃)(CH₂)₂OCH₃ | N(CH₃)(CH₂)₂N(CH₃)₂ |
| NCH₃(CH₂CH₃) | NHPh | 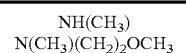 | 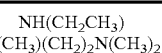 |
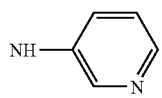  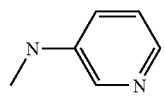  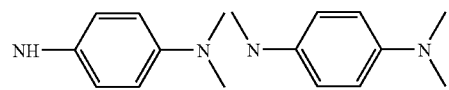
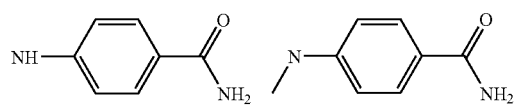  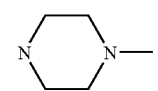  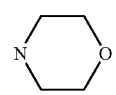

-continued
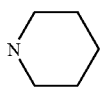 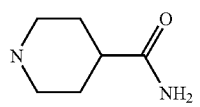 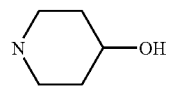 
or
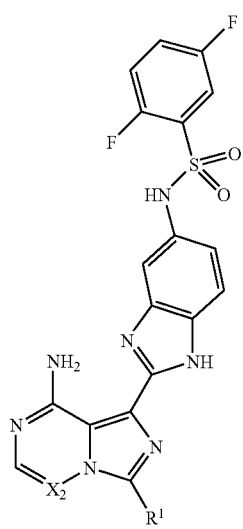
wherein X₂ is either N or CH, R¹ is —XR$^a$, X is either S or O, and XR$^a$ is any one of:
XCH₃
XiPr
X-tBu
X—(CH₂)₂CH₃
X—(CH₂)₃CH₃
X—(CH₂)₂OCH₃
X—(CH₂)₂N(CH₃)₂
X-cyclobutyl
X-cyclopentyl
X-cyclohexyl
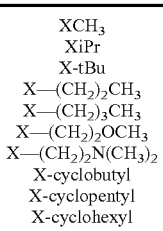
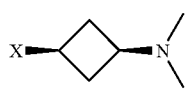
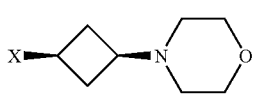
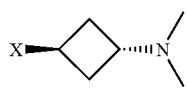
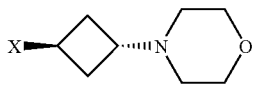
-continued
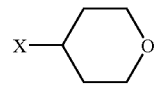
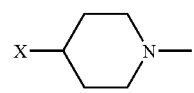
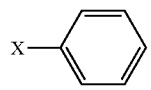
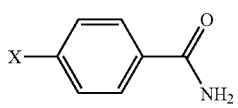
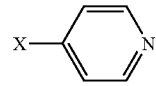

-continued
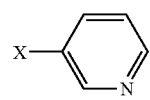
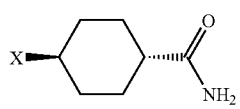
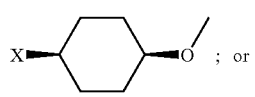 ; or
-continued
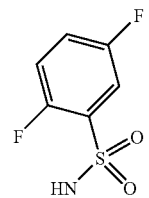
wherein X₂ is either N or CH, and NR⁴R⁵ is any one of:
| | | | |
|---|---|---|---|
| N(CH₃)₂ | N(CH₂CH₃)₂ | NH(CH₃) | NH(CH₂CH₃) |
| NH(CH₂)₂OCH₃ | NH(CH₂)₂N(CH₃)₂ | N(CH₃)(CH₂)₂OCH₃ | N(CH₃)(CH₂)₂N(CH₃)₂ |
| NCH₃(CH₂CH₃) | NHPh | 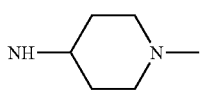 | 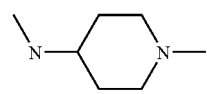 |
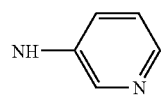 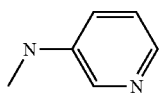 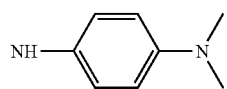 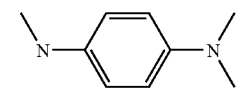
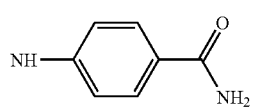 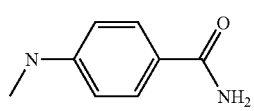 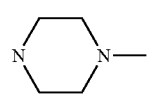 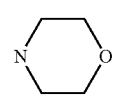
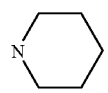 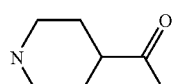 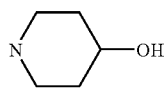  ;
or any one of the following -continued
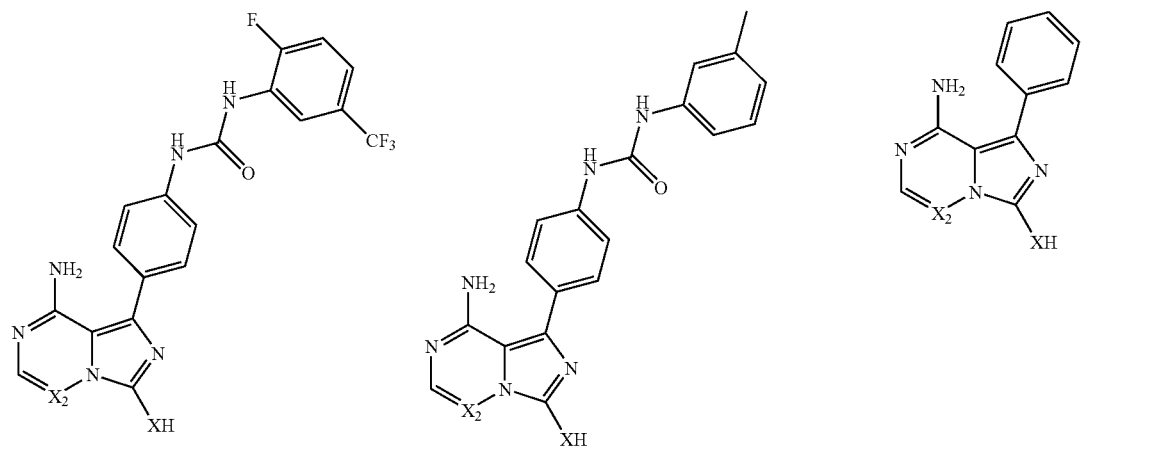
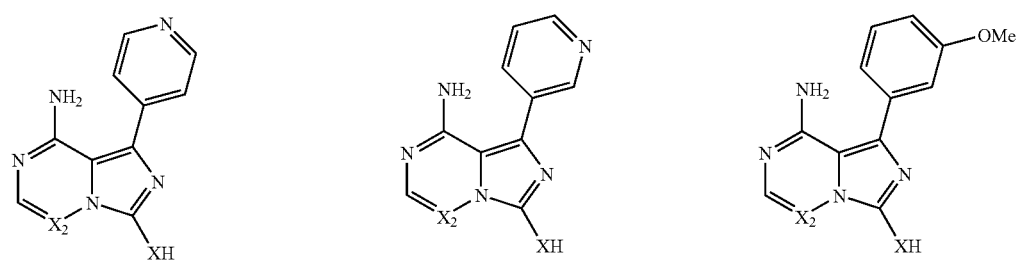
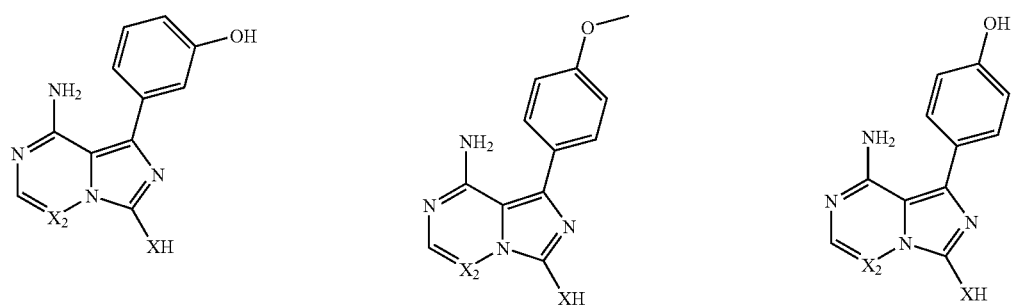
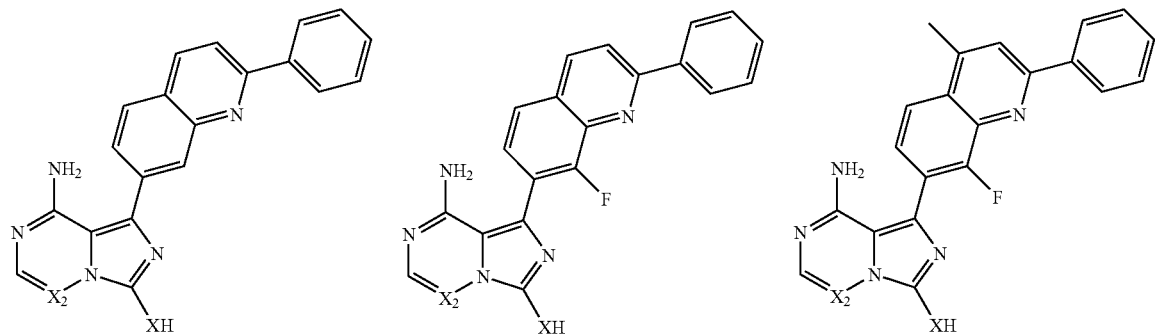

-continued
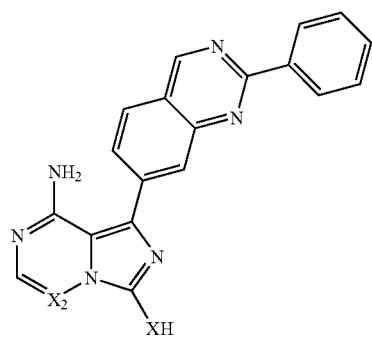 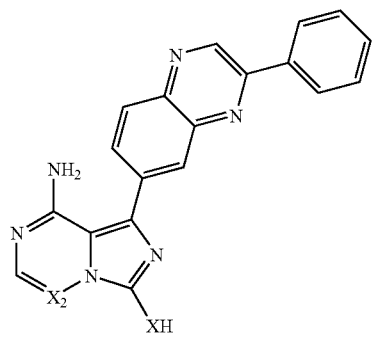 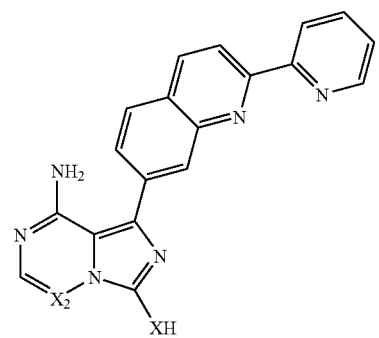
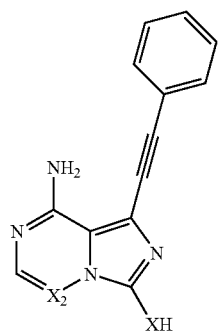 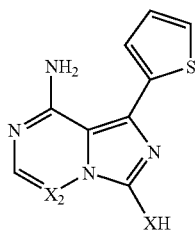 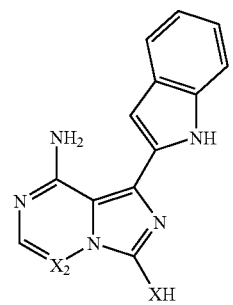
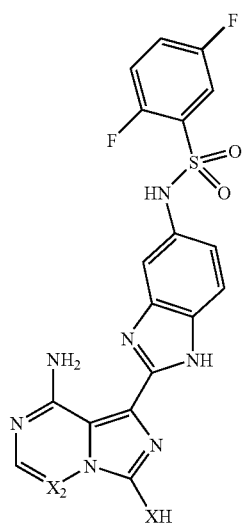 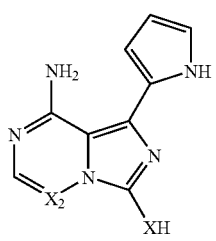 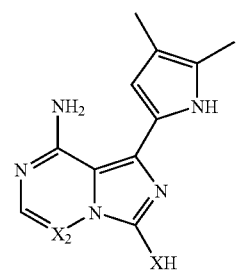
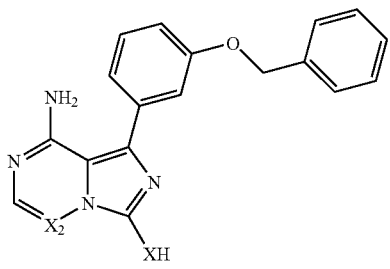 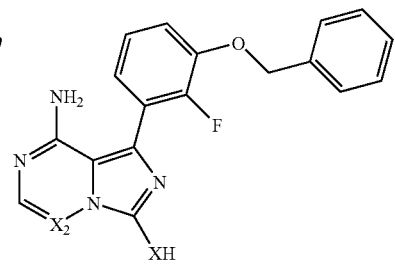 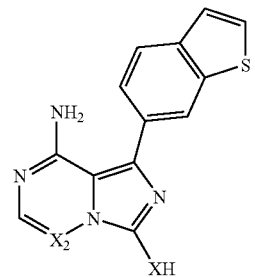

wherein $X_2$ is either N or CH, and X is either O or S;
or a pharmaceutically acceptable salt thereof.

The compounds of the present invention include any one of:

1-(3-Benzyloxy-phenyl)-3-ethoxy-imidazo[1,5-a]pyrazin-8-ylamine;

3-Ethoxy-1-(2-phenyl-quinolin-7-yl)-imidazo[1,5-a]pyrazin-8-ylamine;

8-Amino-1-(3-benzyloxy-phenyl)-imidazo[1,5-a]pyrazine-3-carboxylic acid amide;

1-(1H-Indol-2-yl)-3-methylsulfanyl-imidazo[1,5-a]pyrazin-8-ylamine;

1-(8-Fluoro-2-phenyl-quinolin-7-yl)-3-methylsulfanyl-imidazo[1,5-a]pyrazin-8-ylamine;

1-(3-Benzyloxy-phenyl)-3-methylsulfanyl-imidazo[1,5-a]pyrazin-8-ylamine;

1-Iodo-3-methylsulfanyl-imidazo[1,5-a]pyrazin-8-ylamine;

8-Amino-1-(3-benzyloxy-phenyl)-imidazo[1,5-a]pyrazin-3-ol;

3-Benzylsulfanyl-1-(1H-indol-2-yl)-imidazo[1,5-a]pyrazin-8-ylamine;

8-Amino-1-(1H-indol-2-yl)-imidazo[1,5-a]pyrazine-3-thiol;

{[8-Amino-1-(1H-indol-2-yl)imidazo[1,5-a]pyrazin-3-yl]thio}acetonitrile;

1-(1H-Indol-2-yl)-3-{[4-(methylsulfonyl)benzyl]thio}imidazo[1,5-a]pyrazin-8-amine;

or a pharmaceutically acceptable salt thereof.

The present invention includes a method of inhibiting protein kinase activity according to the present invention comprises administering a compound of Formula I, or a pharmaceutically acceptable salt thereof. The method includes wherein the protein kinase is IGF-1R, mTOR, Aurora A, Blk, CHK1, c-RAF, Flt3, Fyn, Lck, MAPK2, ROCK-II, Tie-2, KDR, or Fak. The method includes wherein the activity of the protein kinase affects hyperproliferative disorders. The method includes wherein the activity of the protein kinase influences angiogenesis, vascular permeability, immune response, cellular apoptosis, tumor growth, or inflammation.

A method of the present invention of treating a patient having a condition which is mediated by protein kinase activity, comprises administering to the patient a therapeutically effective amount of a compound of Formula I, or a pharmaceutically acceptable salt thereof. The method includes wherein the protein kinase is IGF-1R or mTOR. The method includes wherein the protein kinase is Aurora A, Blk, CHK1, c-RAF, Flt3, Fyn, Lck, MAPK2, ROCK-II, Tie-2, KDR, or Fak. The method includes wherein the condition mediated by protein kinase activity is a hyperproliferative disorder. The method includes wherein the activity of the protein kinase influences angiogenesis, vascular permeability, immune response, cellular apoptosis, tumor growth, or inflammation. The method includes wherein the protein kinase is a protein serine/threonine kinase or a protein tyrosine kinase. The method includes wherein the condition mediated by protein kinase activity is one or more ulcers. The method includes wherein the ulcer or ulcers are caused by a bacterial or fungal infection; or the ulcer or ulcers are Mooren ulcers; or the ulcer or ulcers are a symptom of ulcerative colitis. The method includes wherein the condition mediated by protein kinase activity is Lyme disease, sepsis or infection by Herpes simplex, Herpes Zoster, human immunodeficiency virus, parapoxvirus, protozoa, or toxoplasmosis. The method includes wherein the condition mediated by protein kinase activity is von Hippel Lindau disease, pemphigoid, psoriasis, Paget's disease, or polycystic kidney disease. The method includes wherein the condition mediated by protein kinase activity is fibrosis, sarcoidosis, cirrhosis, thyroiditis, hyperviscosity syndrome, Osler-Weber-Rendu disease, chronic occlusive pulmonary disease, asthma, exudtaes, ascites, pleural effusions, pulmonary edema, cerebral edema or edema following burns, trauma, radiation, stroke, hypoxia, or ischemia. The method includes wherein the condition mediated by protein kinase activity is ovarian hyperstimulation syndrome, preeclampsia, menometrorrhagia, or endometriosis. The method includes wherein the condition mediated by protein kinase-activity is chronic inflammation, systemic lupus, glomerulonephritis, synovitis, inflammatory bowel disease, Crohn's disease, glomerulonephritis, rheumatoid arthritis and osteoarthritis, multiple sclerosis, or graft rejection. The method includes wherein the condition mediated by protein kinase activity is sickle cell anaemia. The method includes wherein the condition mediated by protein kinase activity is an ocular condition. The method includes wherein the ocular condition is ocular or macular edema, ocular neovascular disease, seleritis, radial keratotomy, uveitis, vitritis, myopia, optic pits, chronic retinal detachment, post-laser treatment complications, conjunctivitis, Stargardt's disease, Eales disease, retinopathy, or macular degeneration. The method includes wherein the condition mediated by protein kinase activity is a cardiovascular condition. The method includes wherein the condition mediated by protein kinase activity is atherosclerosis, restenosis, ischemia/reperfusion injury, vascular occlusion, venous malformation, or carotid obstructive disease. The method includes wherein the condition mediated by protein kinase activity is cancer. The method includes wherein the cancer is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, or malignant ascites. The method includes wherein the cancer is Kaposi's sarcoma, Hodgkin's disease, lymphoma, myeloma, or leukemia. Further, the method includes wherein the condition mediated by protein kinase activity is Crow-Fukase (POEMS) syndrome or a diabetic condition. The method includes wherein the diabetic condition is insulin-dependent diabetes mellitus glaucoma, diabetic retinopathy, or microangiopathy. The method also includes wherein the protein kinase activity is involved in T cell activation, B cell activation, mast cell degranulation, monocyte activation, signal transduction, apoptosis, the potentiation of an inflammatory response or a combination thereof.

The present invention includes the use of a compound of Formula I, or a pharmaceutically acceptable salt thereof, for the preparation of a pharmaceutical composition for the treatment of a disease which responds to an inhibition of the IGF-1R-dependent cell proliferation, mTOR, Aurora A, Blk, CHK1, c-RAF, Flt3, Fyn, Lck, MAPK2, ROCK-II, Tie-2, KDR, or Fak.

The present invention includes the use of a compound of Formula I, or a pharmaceutically acceptable salt thereof, for the preparation of a pharmaceutical composition for the treatment of a disease which responds to an inhibition of the IGF-1R tyrosine kinase, mTOR, Aurora A, Blk, CHK1, c-RAF, Flt3, Fyn, Lck, MAPK2, ROCK-II, Tie-2, KDR, or Fak.

The present invention includes a pharmaceutical composition comprising a therapeutically effective amount of a compound of Formula I, or a pharmaceutically acceptable salt thereof, and a pharmaceutically acceptable carrier. The invention includes a method of inhibiting protein kinase activity that comprises administering such pharmaceutical composition. The invention includes a method of inhibiting IGF-1R, mTOR, Aurora A, Blk, CHK1, c-RAF, Flt3, Fyn, Lck, MAPK2, ROCK-II, Tie-2, KDR, or Fak activity that comprises administering such pharmaceutical composition. The invention includes a method of treating a patient having a condition which is mediated by protein kinase activity by administering to the patient a therapeutically effective amount of such pharmaceutical composition.

The following include core structures of the present invention wherein at least one of $X_3$-$X_7$ is optionally substituted N and the core structure can have $Q^1$ and $R^1$ substituents as defined above (the substituent is hydrogen where hydrogen is specified):

| Structure | Name of unsubstituted core with NH$_2$ group |
|---|---|
| 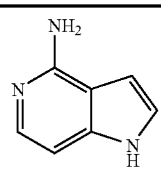 | 1H-Pyrrolo[3,2-c]-pyridin-4-ylamine |
| 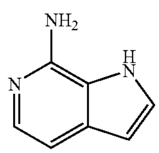 | 1H-Pyrrolo[2,3-c]-pyridin-7-ylamine |
| 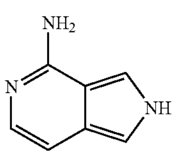 | 2H-Pyrrolo[3,4-c]-pyridin-4-ylamine |
| 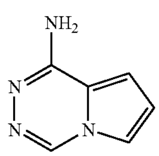 | Pyrrolo[1,2-d]-[1,2,4]triazin-1-ylamine |
| 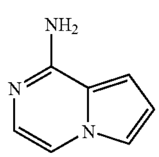 | Pyrrolo[1,2-a]-pyrazin-1-ylamine |
| 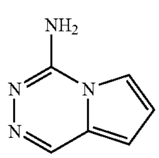 | Pyrrolo[1,2-d]-[1,2,4]triazin-4-ylamine |
| 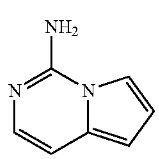 | Pyrrolo[1,2-c]-pyrimidin-1-ylamine |

-continued

| Structure | Name of unsubstituted core with NH$_2$ group |
|---|---|
| 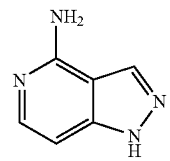 | 1H-Pyrazolo[4,3-c]-pyridin-4-ylamine |
| 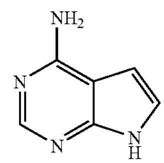 | 7H-Pyrrolo[2,3-d]pyrimidin-4-ylamine |
| 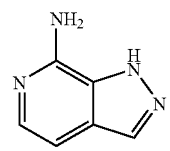 | 1H-Pyrazolo[3,4-c]-pyridin-7-ylamine |
| 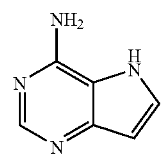 | 5H-Pyrrolo[3,2-d]-pyrimidin-4-ylamine |
| 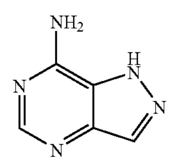 | 1H-Pyrazolo[4,3-d]-pyrimidin-7-ylamine |
| 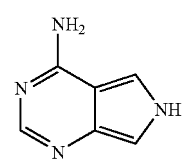 | 6H-Pyrrolo[3,4-d]-pyrimidin-4-ylamine |
| 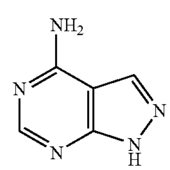 | 1H-Pyrazolo[3,4-d]-pyrimidin-4-ylamine |
| 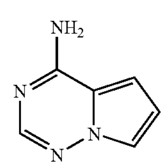 | Pyrrolo[2,1-f]-[1,2,4]triazin-4-ylamine |
| 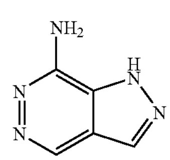 | 1H-Pyrazolo[3,4-d]-pyridazin-7-ylamine |

-continued

| Structure | Name of unsubstituted core with NH₂ group |
|---|---|
| 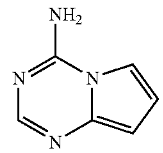 | Pyrrolo[1,2-a]-[1,3,5]triazin-4-ylamine |
| 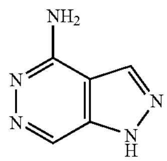 | 1H-Pyrazolo[3,4-d]-pyridazin-4-ylamine |
| 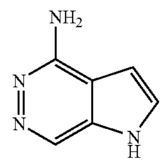 | 1H-Pyrrolo[2,3-d]-pyridazin-4-ylamine |
| 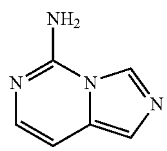 | Imidazo[1,5-c]-pyrimidin-5-ylamine |
| 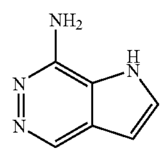 | 1H-Pyrrolo[2,3-d]-pyridazin-7-ylamine |
| 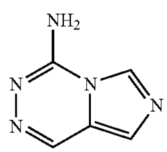 | Imidazo[1,5-d]-[1,2,4]triazin-4-ylamine |
| 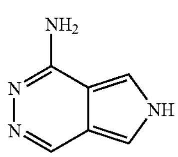 | 1-Methyl-6H-pyrrolo[3,4-d]-pyridazine |
| 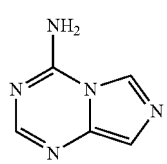 | Imidazo[1,5-a]-[1,3,5]triazin-4-ylamine |
| 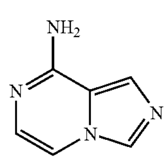 | Imidazo[1,5-a]-pyrazin-8-ylamine |

-continued

| Structure | Name of unsubstituted core with NH₂ group |
|---|---|
| 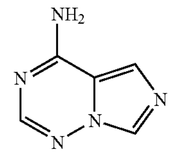 | Imidazo[1,5-f]-[1,2,4]triazin-4-ylamine |
| 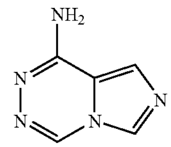 | Imidazo[1,5-d]-[1,2,4]triazin-1-ylamine |

Unless otherwise stated, the connections of compound name moieties are at the rightmost recited moiety. That is, the substituent name starts with a terminal moiety, continues with any bridging moieties, and ends with the connecting moiety. For example, hetarylthio$C_{1-4}$alkyl has a heteroaryl group connected through a thio sulfur to a $C_{1-4}$ alkyl that connects to the chemical species bearing the substituent.

In all of the above circumstances forbidden or unstable valences, such as, but not limited to, N-halogen or oxygen-oxygen bonds, are excluded.

As used herein, for example, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group. Further, Coalkyl includes being a substituted bond—that is, for example, —X-Y-Z is —C(O)—$C_{2-4}$alkyl when X is Coalkyl, Y is Coalkyl, and Z is —C(O)—$C_{2-4}$alkyl.

In all embodiments of this invention, the term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl, and the like.

The term "halo" refers to fluoro, chloro, bromo, or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, and the like.

The term "acyl" refers to the structure —C(═O)—R, in which R is a general substituent variable such as, for example $R^1$ described above. Examples include, but are not limited to, (bi)(cyclo)alkylketo, (cyclo)alkenylketo, alkynylketo, arylketo, hetarylketo, heterocyclylketo, heterobicycloalkylketo, spiroalkylketo.

Unless otherwise specified, the term "cycloalkyl" refers to a 3-8 carbon cyclic aliphatic ring structure, optionally substituted with for example, alkyl, hydroxy, oxo, and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like.

The term "bicycloalkyl" refers to a structure consisting of two cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" refers to a structure consisting of two cycloalkyl moieties that have exactly one atom in common. Examples include, but are not limited to, spiro[4.5]decyl, spiro[2.3]hexyl, and the like.

The term "heterobicycloalkyl" refers to a bicycloalkyl structure in which at least one carbon atom is replaced with a heteroatom independently selected from oxygen, nitrogen, and sulfur.

The term "heterospiroalkyl" refers to a spiroalkyl structure in which at least one carbon atom is replaced with a heteroatom independently selected from oxygen, nitrogen, and sulfur.

The term "alkylcarbonyloxyalkyl" refers to an ester moiety, for example acetoxymethyl, n-butyryloxyethyl, and the like.

The term "alkynylcarbonyl" refers to an alkynylketo functionality, for example propynoyl and the like.

The term "hydroxyalkyl" refers to an alkyl group substituted with one or more hydroxy groups, for example hydroxymethyl, 2,3-dihydroxybutyl, and the like.

The term "alkylsulfonylalkyl" refers to an alkyl group substituted with an alkylsulfonyl moiety, for example mesylmethyl, isopropylsulfonylethyl, and the like.

The term "alkylsulfonyl" refers to a sulfonyl moiety substituted with an alkyl group, for example mesyl, n-propylsulfonyl, and the like.

The term "acetylaminoalkyl" refers to an alkyl group substituted with an amide moiety, for example acetylaminomethyl and the like.

The term "acetylaminoalkenyl" refers to an alkenyl group substituted with an amide moiety, for example 2-(acetylamino)vinyl and the like.

The term "alkenyl" refers to an ethylenically unsaturated hydrocarbon group, straight or branched chain, having 1, or 2 ethylenic bonds, for example vinyl, allyl, 1-butenyl, 2-butenyl, isopropenyl, 2-pentenyl, and the like.

The term "haloalkenyl" refers to an alkenyl group substituted with one or more halo groups.

Unless otherwise specified, the term "cycloalkenyl" refers to a cyclic aliphatic 3 to 8 ring structure, optionally substituted with alkyl, hydroxy and halo, having 1, or 2 ethylenic bonds such as methylcyclopropenyl, trifluoromethylcyclopropenyl, cyclopentenyl, cyclohexenyl, 1,4-cyclohexadienyl, and the like.

The term "alkynyl" refers to an unsaturated hydrocarbon group, straight or branched, having at least one acetylenic bond, for example ethynyl, propargyl, and the like.

The term, "haloalkynyl" refers to an alkynyl group substituted with one or more independent halo groups.

The term "alkylcarbonyl" refers to an alkylketo functionality, for example acetyl, n-butyryl, and the like.

The term "alkenylcarbonyl" refers to an alkenylketo functionality, for example, propenoyl and the like.

The term "aryl" refers to phenyl or naphthyl which may be optionally substituted. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methylphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, 3-benzyloxyphenyl, 4-benzyloxyphenyl, 3-benzyloxy-2-fluorophenyl, 7-phenyl-naphthalen-2-yl, 1-fluoro-7-phenyl-naphthalen-2-yl, 8-fluoro-7-phenyl-naphthalen-2-yl, 7-(2-fluorophenyl)naphthalen-2-yl, 7-(pyridin-2-yl)-naphthalen-2-yl, 1-fluoro-7-(pyridin-2-yl)naphthalen-2-yl, and 2-iodo-4-methylphenyl. The aryl ring may be optionally substituted with one or more substituents.

The terms "heteroaryl" or "hetaryl" or "heteroar-" or "hetar-" refer to a substituted or unsubstituted 5- or 6-membered unsaturated ring containing one, two, three, or four independently selected heteroatoms, preferably one or two heteroatoms independently selected from oxygen, nitrogen, and sulfur or to a bicyclic unsaturated ring system containing up to 10 atoms including at least one heteroatom selected from oxygen, nitrogen, and sulfur. Examples of hetaryls include, but are not limited to, 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, benzothienyl, 2-, 3-, 4-, 5-, 6-, or 7-(1H-indolyl), 2-phenyl-quinolin-7-yl, 8-fluoro-2-phenyl-quinolin-7-yl, 8-fluoro-4-methyl-2-phenyl-quinolin-7-yl, and 4-methyl-2-phenyl-quinolin-7-yl. The heterocyclic ring may be optionally substituted with one or more substituents.

The terms "aryl-alkyl" or "arylalkyl" or "aralkyl" are used to describe a group wherein the alkyl chain can be branched or straight chain forming a bridging portion with the terminal aryl, as defined above, of the aryl-alkyl moiety. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxphenyl)butyl, and 10-phenyldecyl.

The terms "aryl-cycloalkyl" or "arylcycloalkyl" are used to describe a group wherein the terminal aryl group is attached to a cycloalkyl group, for example phenylcyclopentyl and the like.

The terms "aryl-alkenyl" or "arylalkenyl" or "aralkenyl" are used to describe a group wherein the alkenyl chain can be branched or straight chain forming a bridging portion of the aralkenyl moiety with the terminal aryl portion, as defined above, for example styryl (2-phenylvinyl), phenpropenyl, and the like.

The terms "aryl-alkynyl" or "arylalkynyl" or "aralkynyl" are used to describe a group wherein the alkynyl chain can be branched or straight chain forming a bridging portion of the aryl-alkynyl moiety with the terminal aryl portion, as defined above, for example 3-phenyl-1-propynyl, and the like.

The terms "aryl-oxy" or "aryloxy" or "aroxy" are used to describe a terminal aryl group attached to a bridging oxygen atom. Typical aryl-oxy groups include phenoxy, 3,4-dichlorophenoxy, and the like.

The terms "aryl-oxyalkyl" or "aryloxyalkyl" or "aroxyalkyl" are used to describe a group wherein an alkyl group is substituted with a terminal aryl-oxy group, for example pentafluorophenoxymethyl and the like.

The term "heterocycloalkenyl" refers to a cycloalkenyl structure in which at least one carbon atom is replaced with a heteroatom selected from oxygen, nitrogen, and sulfur.

The terms "hetaryl-oxy" or "heteroaryl-oxy" or "hetaryloxy" or "heteroaryloxy" or "hetaroxy" or "heteroaroxy" are used to describe a terminal hetaryl group attached to a bridging oxygen atom. Typical hetaryl-oxy groups include 4,6-dimethoxypyrimidin-2-yloxy and the like.

The terms "hetarylalkyl" or "heteroarylalkyl" or "hetarylalkyl" or "heteroaryl-alkyl" or "hetaralkyl" or "heteroaralkyl" are used to describe a group wherein the alkyl chain can be branched or straight chain forming a bridging portion of the heteroaralkyl moiety with the terminal heteroaryl portion, as defined above, for example 3-furylmethyl, thenyl, furfuryl, and the like.

The terms "hetarylalkenyl" or "heteroarylalkenyl" or "hetaryl-alkenyl" or "heteroaryl-alkenyl" or "hetaralkenyl" or "heteroaralkenyl" are used to describe a group wherein the alkenyl chain can be branched or straight chain forming a bridging portion of the heteroaralkenyl moiety with the terminal heteroaryl portion, as defined above, for example 3-(4-pyridyl)-1-propenyl.

The terms "hetarylalkynyl" or "heteroarylalkynyl" or "hetaryl-alkynyl" or "heteroaryl-alkynyl" or "hetaralkynyl" or "heteroaralkynyl" are used to describe a group wherein the alkynyl chain can be branched or straight chain forming a bridging portion of the heteroaralkynyl moiety with the heteroaryl portion, as defined above, for example 4-(2-thienyl)-1-butynyl.

The term "heterocyclyl" or "hetcyclyl" refers to a substituted or unsubstituted 4-, 5-, or 6-membered saturated or partially unsaturated ring containing one, two, or three heteroatoms, preferably one or two heteroatoms independently selected from oxygen, nitrogen and sulfur; or to a bicyclic ring system containing up to 10 atoms including at least one heteroatom independently selected from oxygen, nitrogen, and sulfur wherein the ring containing the heteroatom is saturated. Examples of heterocyclyls include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl, and 5-methyl-6-chromanyl.

The terms "heterocyclylalkyl" or "heterocyclyl-alkyl" or "hetcyclylalkyl" or "hetcyclyl-alkyl" are used to describe a group wherein the alkyl chain can be branched or straight chain forming a bridging portion of the heterocyclylalkyl moiety with the terminal heterocyclyl portion, as defined above, for example 3-piperidinylmethyl and the like.

The terms "heterocyclylalkenyl" or "heterocyclyl-alkenyl" or "hetcyclylalkenyl" or "hetcyclyl-alkenyl" are used to describe a group wherein the alkenyl chain can be branched or straight chain forming a bridging portion of the heterocyclylalkenyl moiety with the terminal heterocyclyl portion, as defined above, for example 2-morpholinyl-1-propenyl and the like.

The terms "heterocyclylalkynyl" or "heterocyclyl-alkynyl" or "hetcyclylalkynyl" or "hetcyclyl-alkynyl" are used to describe a group wherein the alkynyl chain can be branched or straight chain forming a bridging portion of the heterocyclylalkynyl moiety with the terminal heterocyclyl portion, as defined above, for example 2-pyrrolidinyl-1-butynyl and the like.

The term "carboxylalkyl" refers to a terminal carboxyl (—COOH) group attached to branched or straight chain alkyl groups as defined above.

The term "carboxylalkenyl" refers to a terminal carboxyl (—COOH) group attached to branched or straight chain alkenyl groups as defined above.

The term "carboxylalkynyl" refers to a terminal carboxyl (—COOH) group attached to branched or straight chain alkynyl groups as defined above.

The term "carboxylcycloalkyl" refers to a terminal carboxyl (—COOH) group attached to a cyclic aliphatic ring structure as defined above.

The term "carboxylcycloalkenyl" refers to a terminal carboxyl (—COOH) group attached to a cyclic aliphatic ring structure having ethylenic bonds as defined above.

The terms "cycloalkylalkyl" or "cycloalkyl-alkyl" refer to a terminal cycloalkyl group as defined above attached to an alkyl group, for example cyclopropylmethyl, cyclohexylethyl, and the like.

The terms "cycloalkylalkenyl" or "cycloalkyl-alkenyl" refer to a terminal cycloalkyl group as defined above attached to an alkenyl group, for example cyclohexylvinyl, cycloheptylallyl, and the like.

The terms "cycloalkylalkynyl" or "cycloalkyl-alkynyl" refer to a terminal cycloalkyl group as defined above attached to an alkynyl group, for example cyclopropylpropargyl, 4-cyclopentyl-2-butynyl, and the like.

The terms "cycloalkenylalkyl" or "cycloalkenyl-alkyl" refer to a terminal cycloalkenyl group as defined above attached to an alkyl group, for example 2-(cyclopenten-1-yl)ethyl and the like.

The terms "cycloalkenylalkenyl" or "cycloalkenyl-alkenyl" refer to terminal a cycloalkenyl group as defined above attached to an alkenyl group, for example 1-(cyclohexen-3-yl)allyl and the like.

The terms "cycloalkenylalkynyl" or "cycloalkenyl-alkynyl" refer to terminal a cycloalkenyl group as defined above attached to an alkynyl group, for example I-(cyclohexen-3-yl)propargyl and the like.

The term "carboxylcycloalkylalkyl" refers to a terminal carboxyl (—COOH) group attached to the cycloalkyl ring portion of a cycloalkylalkyl group as defined above.

The term "carboxylcycloalkylalkenyl" refers to a terminal carboxyl (—COOH) group attached to the cycloalkyl ring portion of a cycloalkylalkenyl group as defined above.

The term "carboxylcycloalkylalkynyl" refers to a terminal carboxyl (—COOH) group attached to the cycloalkyl ring portion of a cycloalkylalkynyl group as defined above.

The term "carboxylcycloalkenylalkyl" refers to a terminal carboxyl (—COOH) group attached to the cycloalkenyl ring portion of a cycloalkenylalkyl group as defined above.

The term "carboxylcycloalkenylalkenyl" refers to a terminal carboxyl (—COOH) group attached to the cycloalkenyl ring portion of a cycloalkenylalkenyl group as defined above.

The term "carboxylcycloalkenylalkynyl" refers to a terminal carboxyl (—COOH) group attached to the cycloalkenyl ring portion of a cycloalkenylalkynyl group as defined above.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

The term "haloalkoxy" refers to an alkoxy group substituted with one or more halo groups, for example chloromethoxy, trifluoromethoxy, difluoromethoxy, perfluoroisobutoxy, and the like.

The term "alkoxyalkoxyalkyl" refers to an alkyl group substituted with an alkoxy moiety which is in turn is substituted with a second alkoxy moiety, for example methoxymethoxymethyl, isopropoxymethoxyethyl, and the like.

The term "alkylthio" includes both branched and straight chain alkyl groups attached to a bridging sulfur atom, for example methylthio and the like.

The term "haloalkylthio" refers to an alkylthio group substituted with one or more halo groups, for example trifluoromethylthio and the like.

The term "alkoxyalkyl" refers to an alkyl group substituted with an alkoxy group, for example isopropoxymethyl and the like.

The term "alkoxyalkenyl" refers to an alkenyl group substituted with an alkoxy group, for example 3-methoxyallyl and the like.

The term "alkoxyalkynyl" refers to an alkynyl group substituted with an alkoxy group, for example 3-methoxypropargyl.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkoxycarbonylalkenyl" refers to a straight chain or branched alkenyl as defined above substituted with an alkoxycarbonyl, for example 4-(ethoxycarbonyl)-2-butenyl and the like.

The term "alkoxycarbonylalkynyl" refers to a straight chain or branched alkynyl as defined above substituted with an alkoxycarbonyl, for example 4-(ethoxycarbonyl)-2-butynyl and the like.

The term "haloalkoxyalkyl" refers to a straight chain or branched alkyl as defined above substituted with a haloalkoxy, for example 2-chloroethoxymethyl, trifluoromethoxymethyl and the like.

The term "haloalkoxyalkenyl" refers to a straight chain or branched alkenyl as defined above substituted with a haloalkoxy, for example 4-(chloromethoxy)-2-butenyl and the like.

The term "haloalkoxyalkynyl" refers to a straight chain or branched alkynyl as defined above substituted with a haloalkoxy, for example 4-(2-fluoroethoxy)-2-butynyl and the like.

The term "alkylthioalkyl" refers to a straight chain or branched alkyl as defined above substituted with an alkylthio group, for example methylthiomethyl, 3-(isobutylthio)heptyl, and the like.

The term "alkylthioalkenyl" refers to a straight chain or branched alkenyl as defined above substituted with an alkylthio group, for example 4-(methylthio)-2-butenyl and the like.

The term "alkylthioalkynyl" refers to a straight chain or branched alkynyl as defined above substituted with an alkylthio group, for example 4-(ethylthio)-2-butynyl and the like.

The term "haloalkylthioalkyl" refers to a straight chain or branched alkyl as defined above substituted with an haloalkylthio group, for example 2-chloroethylthiomethyl, trifluoromethylthiomethyl and the like.

The term "haloalkylthioalkenyl" refers to a straight chain or branched alkenyl as defined above substituted with an haloalkylthio group, for example 4-(chloromethylthio)-2-butenyl and the like.

The term "haloalkylthioalkynyl" refers to a straight chain or branched alkynyl as defined above substituted with a haloalkylthio group, for example 4-(2-fluoroethylthio)-2-butynyl and the like.

The term "dialkoxyphosphorylalkyl" refers to two straight chain or branched alkoxy groups as defined above attached to a pentavalent phosphorous atom, containing an oxo substituent, which is in turn attached to an alkyl, for example diethoxyphosphorylmethyl and the like.

One in the art understands that an "oxo" requires a second bond from the atom to which the oxo is attached. Accordingly, it is understood that oxo cannot be subststituted onto an aryl or heteroaryl ring.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I in combination with a pharmaceutically acceptable carrier.

Preferably the composition is comprised of a pharmaceutically acceptable carrier and a non-toxic therapeutically effective amount of a compound of Formula I as described above (or a pharmaceutically acceptable salt thereof).

Moreover, within this preferred embodiment, the invention encompasses a pharmaceutical composition for the treatment of disease by inhibiting kinases, comprising a pharmaceutically acceptable carrier and a non-toxic therapeutically effective amount of compound of Formula I as described above (or a pharmaceutically acceptable salt thereof).

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid.

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or a pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

BIOLOGICAL ASSAYS

The efficacy of the Examples of the invention, compounds of Formula I, as inhibitors of at least one of the following kinases, including but not limited to, insulin-like growth factor-1 receptor (IGF-1R), mTOR, Aurora A, Blk, CHK1, c-RAF, Flt3, Fyn, Lck, MAPK2, ROCK-II, Tie-2, KDR, or Fak were demonstrated and confirmed by pharmacological in vitro assays. The following assays and their respective methods can be carried out with the compounds according to the invention. Activity possessed by compounds of Formula I may be demonstrated in vivo.

In Vitro Tyrosine Kinase Assay

The IGF-1R inhibitory of a compound of Formula I can be shown in a tyrosine kinase assay using purified GST fusion protein containing the cytoplasmic kinase domain of human IGF-1R expressed in Sf9 cells. This assay is carried out in a final volume of 90 µL containing I-100 nM (depending on the specific activity) in an Immulon-4 96-well plate (Thermo Labsystems) pre-coated with 1 µg/well of substrate poly-glutyr (4:1 ratio) in kinase buffer (50 mM Hepes, pH 7.4, 125 mM NaCl, 24 mM $MgCl_2$, 1 mM $MnCl_2$, 1% glycerol, 200 µM $Na_3VO_4$, and 2 mM DTT). The enzymatic reaction was initiated by addition of ATP at a final concentration of 1001M. After incubation at rt for 30 min, the plates were washed with 2 mM imidazole buffered saline with 0.02% Tween-20. Then the plate was incubated with anti-phosphotyrosine mouse monoclonal antibody pY-20 conjugated with horseradish peroxidase (HRP) (Calbiochem) at 167 ng/mL diluted in phosphate buffered saline (PBS) containing 3% bovine serum albumin (BSA), 0.5% Tween-20 and 200 µM $Na_3VO_4$ for 2 h at rt. Following 3×250 µL washes, the bound anti-phosphotyrosine antibody was detected by incubation with 100 µL/well ABTS (Kirkegaard & Perry Labs, Inc.) for 30 min at rt. The reaction was stopped by the addition of 100 µL/well 1% SDS, and the phosphotyrosine dependent signal was measured by a plate reader at 405/490 nm.

EXAMPLES showed inhibition of at least one of the following kinases, including but not limited to, insulin-like growth factor-1 receptor (IGF-1R), mTOR, Aurora A, Blk, CHK1, c-RAF, Flt3, Fyn, Lck, MAPK2, ROCK-II, Tie-2, KDR, or Fak. The following EXAMPLES showed efficacy and activity by inhibiting at least one of the following kinases, including but not limited to, insulin-like growth factor-1 receptor (IGF-1R), mTOR, Aurora A, Blk, CHK1, c-RAF, Flt3, Fyn, Lck, MAPK2, or ROCK-II, Tie-2, KDR, or Fak in the biochemical assay with $IC_{50}$ values less than 50 µM to less than 50 nM. Preferably the $IC_{50}$ value is less than 5 µM. Advantageously, the $IC_{50}$ value is less than 1 µM. More advantageously, the $IC_{50}$ value is less than 200 nM. Even more advantageously, the $IC_{50}$ value is less than 100 nM. Still more advantageously, the $IC_{50}$ value is less than 50 nM.

Cell-based Autophosphotyrosine Assay

NIH 3T3 cells stably expressing full-length human IGF-1R were seeded at $1\times10^4$ cells/well in 0.1 mL Dulbecco's minimal essential medium (DMEM) supplemented with 10% fetal calf serum (FCS) per well in 96-well plates. On Day 2, the medium is replaced with starvation medium (DMEM containing 0.5% FCS) for 2 h and a compound was diluted in 100% dimethyl sulfoxide (DMSO), added to the cells at six final concentrations in duplicates (20, 6.6, 2.2, 0.74, 0.25 and 0.082 µM), and incubated at 37° C. for additional 2 h. Following addition of recombinant human IGF-1 (100 ng/mL) at 37° C. for 15 min, the media was then removed and the cells were washed once with PBS (phosphate-buffered saline), then lysed with cold TGH buffer (1% Triton-100, 10% glycerol, 50 mM HEPES [pH 7.4]) supplemented with 150 mM NaCl, 1.5 mM MgCl, 1 mM EDTA and fresh protease and phosphatase inhibitors [10 µg/mL leupeptin, 25 µg/mL aprotinin, 1 mM phenyl methyl sulphonyl fluoride (PMSF), and 200 µM $Na_3$ $VO_4$]. Cell lysates were transferred to a 96-well microlite2 plate (Corning CoStar #3922) coated with 10 ng/well of IGF-1R antibody (Calbiochem, Cat#GR31L) and incubated at 4° C. overnight. Following washing with TGH buffer, the plate was incubated with anti-phosphotyrosine mouse monoclonal antibody pY-20 conjugated with horseradish peroxidase (HRP) for 2 h at rt. The autophosphotyrosine was then detected by addition of Super Signal ELISA Femto Maximum Sensitivity Substrate (Pierce) and chemiluminescence was read on a Wallac Victor$^2$ 1420 Multilabel Counter. The $IC_{50}$ curves of the compounds were plotted using an ExcelFit program.

Biochemical Assay for Inhibition of mTOR Activity:

The ability of compounds to inhibit the mTOR kinase activity was determined in an in vitro immunoprecipitation (IP) kinase assay using recombinant 4E-BP1 as a substrate. The assay determines the ability of compounds to inhibit phosphorylation of 4E-BP1 a well-known physiological substrate of mTOR. The immunocapture mTOR complex from HeLa cells is incubated with various concentrations of compounds and His-tag 4E-BP1 in kinase assay buffer prior to addition of ATP to start the reaction at RT. The reaction is stopped after 30 mins and the phosphorylated His-tag 4E-BP1 is captured on a Nickel-chelate plate overnight at 4° C. The phosphothreonine content of 4E-BP1 is then measured using phospho-4E-BP1 (T37/46) primary antibody and corresponding anti rabbit IgG HRP conjugated, secondary antibody. The secondary antibody has a reporter enzyme (eg. horseradish peroxidase, HRP) covalently attached, such that binding of primary antibody to phosphorylated 4E-BP1 can be determined quantitatively which is equal to the amount secondary antibody bound to it. The amount of secondary antibody can be determined by incubation with an appropriate HRP substrate.

The stock reagents used are as follows:

Cell Lysis Buffer:
  40 mM HEPES, pH 7.5 containing 120 mM NaCl, 1 mM EDTA, 10 mM sodium pyrophosphate, 10 mM β-glycerophosphate, 50 mM sodium fluoride, 1.5 mM sodium vanadate and 0.3% CHAPS.

Complete mini EDTA-free protease inhibitors (Roche, catalog #11 836 170 001)

HeLa cell pellets (Paragon Bioservices)

Protein G coated plates for immunoprecipitation (Pierce, catalog #15131)

mTOR (aka FRAP) N-19 antibody (Santa Cruz Biotechnology, catalog #sc-1549)

IP Wash Buffer:
  50 mM HEPES, pH 7.5 containing 150 mM NaCl

Kinase Buffer:
  20 mM HEPES, pH 7.5 containing 10 mM MgCl2, 4 mM MnCl2, 10 mM b-mercaptoethanol and 200 uM sodium vanadate. Make fresh for assay.

Recombinant 4E-BP1 (aka PHAS I) (Calbiochem, catalog #516675)
  Dilute 4E-BP1 stock (1 mg/mL) 120 times in kinase assay buffer to obtain a concentration of 0.25 ug/well in 30 uL ATP Solution
  Prepare 330 uM ATP stock in kinase buffer Ni-chelate Plate (Pierce, catalog #15242)

Antibody Dilution Buffer:
  TBST containing 5% skim milk

Phospho-4E-BP1 (T37/46) Antibody:
  1:1000 dilution of phospho-4E-BP1 (T37/46) antibody (Cell Signaling Technology, catalog #9459) in antibody dilution buffer Donkey Anti Rabbit IgG, HRP Conjugated
  1:10,000 dilution of anti rabbit IgG HRP conjugated (GE Healthcare, Catalog #NA934) in antibody dilution buffer HRP Substrate;
  Chemiluminescent reagents (Pierce, catalog #37074)

Assay Protocol:
  HeLa cell lysate was prepared in bulk by homogenizing 25 g of cell pellet in 60 mL of cell lysis buffer and then, centrifuged at 12,000 rpm for 30 mins. The clear supernatant was transferred to fresh tube, aliquoted, quickly frozen and stored at −80° C. until use.

Protein G coated 96-well plate is washed once with lysis buffer and 50 ul of diluted mTOR antibody is added to each well, and incubated at RT for 30-60 mins. Then, 50ug of HeLa cell lysate was added to each well in 50 uL of lysis buffer and incubated at 4° C. in a cold room on a shaker for 2-3 h. Lysate was removed and the plate was washed with 100 uL of complete lysis buffer for 3 times. The plate was further washed 2 times with 100 uL of high salt wash buffer. Diluted 4E-BP1 (substrate) is added to each well in 30 uL. The compounds were added in various concentrations in 5 uL to each well. The drug concentrations varied from 30 uM to 0.1 nM. The final DMSO concentration was 1%. Only DMSO was added to positive control wells. For negative control wells, no ATP solution was added but instead 15 uL of kinase buffer was added, the reaction was started by addition of ATP in 15 uL to a final concentration of 100 uM to rest of the wells except negative control wells. The reaction was carried out for 30 mins at RT. Then, 45 uL of the reaction mixture was transferred to Ni-chelate plate and incubated overnight at 4° C. The plate was washed once with antibody dilution buffer and 50 uL of diluted phospho-4E-BP1 antibody was added to each well, and incubated at RT for 1 h. Then, the plate was washed 4 times with TBST and 50 uL of diluted anti-rabbit secondary antibody was added to each plate, and incubated at RT for 1 h. The plate was washed 4 times with 100 uL of TBST. To each well, 50 uL of Pierce Femto chemiluminescent reagent was added and the chemiluminescence was measured using victor machine.

Comparison of the assay signals obtained in the presence of compound with those of positive and negative controls, allows the degree of inhibition of phospho-4E-BP1 phosphorylation to be determined over a range of compound concentrations. These inhibition values were fitted to a sigmoidal dose-response inhibition curve to determine the $IC_{50}$ values (i.e. the concentration of the compound that inhibits phosphorylation of 4E-BP1 by 50%).

The preferred EXAMPLES showed inhibition of at least one of the following kinases, including but not limited to, insulin-like growth factor-1 receptor (IGF-1R), mTOR, Aurora A, Blk, CHK1, c-RAF, Flt3, Fyn, Lck, MAPK2, ROCK-II, Tie-2, KDR, or Fak in a cell based assay. For example, some EXAMPLES of this invention inhibited phosphorylation of 4E-BP1 by immunocaptured human mTOR as determined in the above assay with $IC_{50}$ values between 0.001 uM and 11.00 uM.

EXPERIMENTAL

Schemes 1-17 below, as well as the experimental procedures that follow, show how to synthesize compounds of this invention and utilize the following abbreviations: Me for methyl, Et for ethyl, $^{i}$Pr or $^{i}$Pr for isopropyl, n-Bu for n-butyl, t-Bu for tert-butyl, Ac for acetyl, Ph for phenyl, 4Cl-Ph or (4Cl)Ph for 4-chlorophenyl, 4Me-Ph or (4Me)Ph for 4-methylphenyl, (p-CH$_3$O)Ph for p-methoxyphenyl, (p-NO$_2$)Ph for p-nitrophenyl, 4Br-Ph or (4Br)Ph for 4-bromophenyl, 2-CF$_3$-Ph or (2CF$_3$)Ph for 2-trifluoromethylphenyl, DMAP for 4-(dimethylamino)pyridine, DCC for 1,3-dicyclohexylcarbodiimide, EDC for 1-(3-dimethylaminopropyl)-3-ethylcarbodiimide hydrochloride, HOBt for 1-hydroxybenzotriazole, HOAt for 1-hydroxy-7-azabenzotriazole, CDI for 1,1'-carbonyldiimidazole, NMO for 4-methylmorpholine N-oxide, DEAD for diethyl azodicarboxylate, DIAD for diisopropyl azodicarboxylate, DBAD for di-tert-butyl azodicarboxylate, HPFC for high performance flash chromatography, rt for room temperature, min for minute, h for hour, Bn for benzyl, DMF for N,N-dimethylforamide, DMA for N,N-dimethylacetamide, NMP for N-methylpyrolidinone, DCE for 1,2-dichloroethane, K$_2$CO$_3$ for potassium carbonate, Cs$_2$CO$_3$ for cesium carbonate, Ag$_2$CO$_3$ for silver carbonate, NaH for sodium hydride.

Accordingly, the following are compounds which are useful as intermediates in the formation of kinase inhibiting Examples.

The compounds of Formula I of this invention and the intermediates used in the synthesis of the compounds of this invention were prepared according to the following methods.

Compound of Formula I-A is equal to compound of Formula I wherein $R^1=OR^4$; $X_1$ and $X_2$=CH, $X_3$ and $X_5$=N, and $X_4$, $X_6$, and $X_7$=C:

I-A

Method A was used when preparing compounds of Formula I-A as shown below in Scheme 1:
Method A:

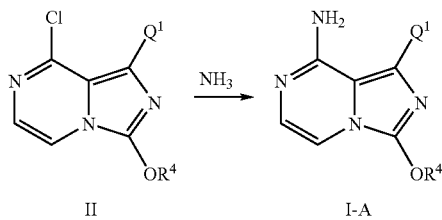

Scheme 1 where $Q^1$ and $R^4$ are as defined previously for compound of Formula I.

In a typical preparation of compounds of Formula I-A, compound of Formula II was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcoholics such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between −78° C. and 120° C. Preferably, the reaction was carried out between 80° C. and about 120° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula II of Scheme I were prepared as shown below in Scheme 2.

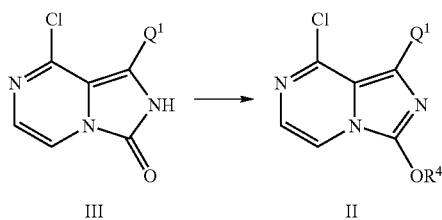

Scheme 2 where $Q^1$ and $R^4$ are defined previously for compound of Formula I.

In a typical preparation of a compound of Formula II, an intermediate of Formula III was treated with an alkylhalide and a suitable base in a suitable solvent at a suitable reaction temperature. Suitable solvents for use in the above process included, but were not limited to DMF, DMA, NMP, acetone, alcohols such as ethanol (EtOH), ethers such as tetrahydrofuran (THF), alkanes such as hexane, and also benzene, halogenated solvents such as methylene chloride ($CH_2Cl_2$), DCE, and chloroform ($CHCl_3$). If desired, mixtures of these solvents were used. The preferred solvent was ethanol. Suitable bases included but were not limited to $K_2CO_3$, $Cs_2CO_3$, $Ag_2CO_3$, and NaH. The preferred base was $Ag_2CO_3$ The above process was carried out at temperatures between about −78° C. and about 120° C. Preferably, the reaction was carried out between rt and about 70° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula III of Scheme 2, were prepared as shown below in Scheme 3:

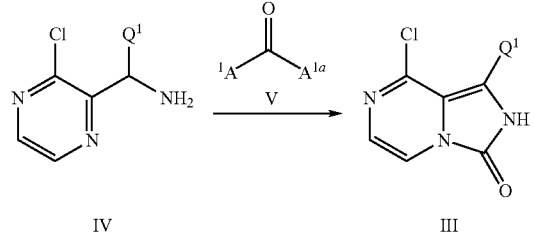

Scheme 3 where $Q^1$ is defined previously for compound of Formula I; $A^1$ and $A^{1a}$ are each independently equal to a suitable leaving group such as chloro, imidazole, triazole, or p-$NO_2$-phenol.

In a typical preparation of a compound of Formula III, a compound of Formula IV and a compound of Formula V where compound V is equal to but not limited to phosgene, triphosgene, N,N'-carbonyldiimidazole, or 4-nitrophenyl chloroformate and the like were reacted in a suitable solvent and a suitable base. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was THF. Suitable bases for use in the process included but were not limited to triethylamine or N,N-diisopropylethylamine, however the desired base was N,N-diisopropylethylamine. The above process was carried out at temperatures between 0° C. and 80° C. Preferably, the reaction was carried out between 40° C. and 80° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula IV, of Scheme 3, were prepared as shown below in Scheme 4:

Scheme 4

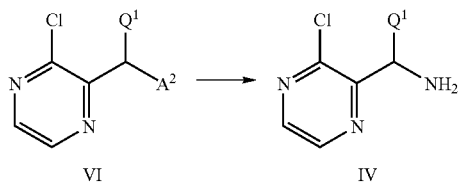

VI → IV where $Q^1$ is as defined previously for compound of Formula I and $A^2$=phthalimido, $N_3$, $N(Boc)_2$ and the like.

In a typical preparation, of a compound of Formula IV, a compound of Formula VI is reacted under suitable reaction conditions in a suitable solvent. When $A^2$=phthalimido, suitable conditions include treatment of compound of Formula VI with hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvent was ethanol. The above process was carried out at temperatures between about 0° C. and about 80° C. Preferably, the reaction was carried out between 22° C. and 40° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula VI, of Scheme 4, were prepared as shown below in Scheme 5:

Scheme 5

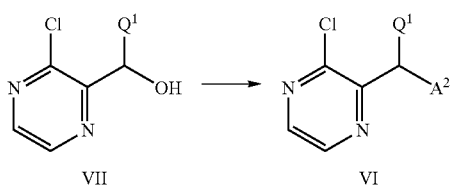

VII → VI where $Q^1$ is as defined previously for compound of Formula I and $A^2$=phthalimido, $N_3$, $N(Boc)_2$ and the like.

In a typical preparation of a compound of Formula VI (when $A^2$=phthalimido), a compound of Formula VII was reacted with a phthalimide under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile (CH$_3$CN); chlorinated solvents such as methylene chloride (CH$_2$Cl$_2$) or chloroform (CHCl$_3$). If desired, mixtures of these solvents were used, however, the preferred solvent was THF. Suitable reactants for use in the above process included, but were not limited to, triphenylphosphine, tributylphosphine and the like and an azodicarboxylate (DIAD, DEAD, DBAD). Preferably the desired reactants were triphenylphosphine and DIAD. The above process may be carried out at temperatures between about −78° C. and about 100° C. Preferably, the reaction was carried out at 22° C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent of triphenylphospine, DIAD and phthalimide was used per equivalent of compound of Formula VII. The compounds of Formula VII were prepared according to known procedures (Ple, N.; et. al. *Tetrahedron*, 1998, 54, 9701-9710) from aldehydes $Q^1$-CHO. Additionally, compound of Formula VII can be reacted with Ts$_2$O, Ms$_2$O, Tf$_2$O, TsCl, MsCl, or SOCl$_2$ in which the hydroxy group is converted to a leaving group such as its respective tosylate, mesylate, triflate or halogen such as chloro and subsequently reacted with an amine equivalent such as NH(Boc)$_2$, phthalimide or azide. Conversion of the amine equivalents to the free amino group can be achieved by known methods such as by treating under acidic conditions (NH(Boc)$_2$), with hydrazine (phthalimide) as shown in Scheme 5, or with dwither triphenylphosphine/water or hydrogen in the presence of a metal catalyst such as Pd/C (azide) will afford the desired amine as shown in Scheme 4.

Compound of Formula I-AA is equal to compound of Formula I wherein $R^1$=CONR$^4$R$^5$; $X_1$ and $X_2$=CH, $X_3$ and $X_5$=N, and $X_4$, $X_6$, and $X_7$=C:

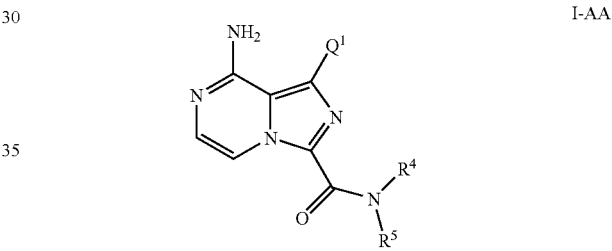

I-AA

Method B was used when preparing compounds of Formula I-AA as shown below in Scheme 6:

Method B:

Scheme 6

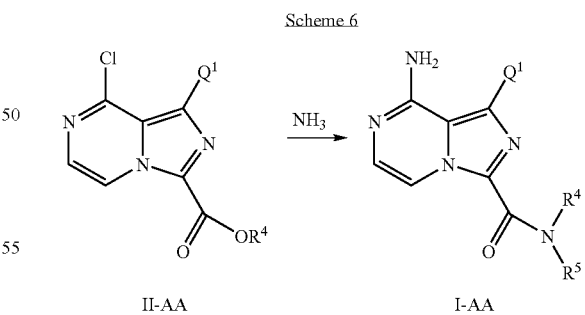

II-AA → I-AA where $Q^1$ is as defined previously for compound of Formula I and NR$^4$R$^5$ equals NH$_2$.

In a typical preparation of compounds of Formula I-AA, compound of Formula II-AA was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used. Compounds of Formula I-AA where $NR^4R^5$ is not equal to $NH_2$, can be prepared as follows: I) when $R^4$ of compound of formula II-AA is equal to a bulky group such as tert-butyl, compounds of formula II-AA can first be subjected to ammonolysis conditions, followed by tert-butyl ester deprotection to afford $R^4$=H, followed by typical amide coupling conditions; 2) when $R^4$ of compound of formula II-AA is equal to a methyl or ethyl group, compounds of formula II-AA can first be subjected to typical Weinreb amidation conditions ($Al(Me)_3$ and $HNR^3R^4$) followed by ammonolysis conditions; 3) when $R^4$ of compound of formula II-AA is equal to an alkyl group, compounds of formula II-AA can first be subjected to suitable saponification conditions to afford the carboxylic acid ($R^4$=H), followed by typical amide coupling conditions, and ammonolysis conditions.

The compounds of Formula II-AA of Scheme 6 were prepared as shown below in Scheme 7.

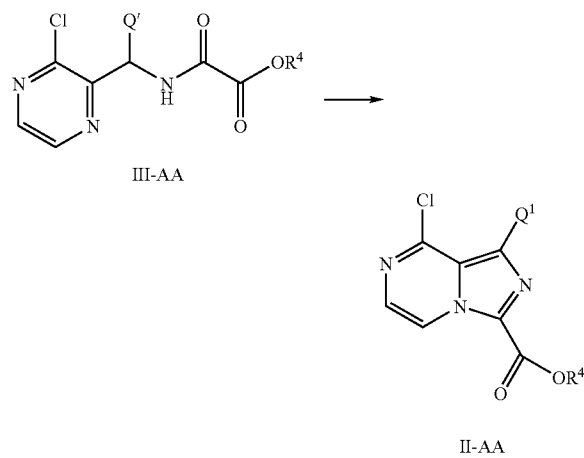

where $Q^1$ and $R^4$ are as defined previously for compound of Formula I.

In a typical preparation of a compound of Formula II-AA, an intermediate of Formula III-AA was treated with suitable cyclization conditions, including but not limited to $POCl_3$ in a suitable solvent at a suitable reaction temperature. Suitable solvents for use in the above process included, but were not limited to, ethers such as tetrahydrofuran (THF), glyme, and the like; acetonitrile; and chlorinated solvents such as methylene chloride ($CH_2Cl_2$) or chloroform ($CHCl_3$). If desired, mixtures of these solvents were used or no solvent was used. The preferred solvents included methylene chloride and acetonitrile. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula III-AA of Scheme 7 were prepared as shown below in Scheme 8:

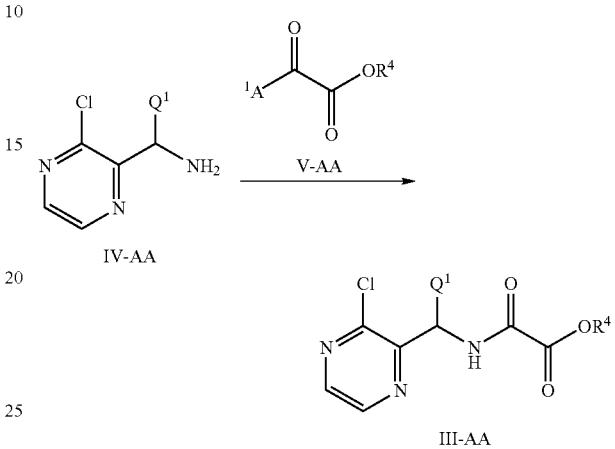

where $Q^1$ and $R^4$ are as defined previously for compound of Formula I and $A^1$=OH, alkoxy, or a leaving group such as chloro or imidazole.

In a typical preparation, of a compound of Formula III-AA, a compound of Formula IV-AA and compound of Formula V-AA were reacted under suitable amide coupling conditions. Suitable conditions include but are not limited to treating compounds of Formula IV-AA and V-AA (when $A^1$=OH) with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvents were methylene chloride and DMF. The above process was carried out at temperatures between about 0° C. and about 80° C. Preferably, the reaction was carried out at about rt. The above process to produce compounds of the present invention was preferably carried out at about atmospheric pressure although higher or lower pressures were used if desired. Substantially, equimolar amounts of reactants were preferably used although higher or lower amounts were used if desired. Alternatively, compounds of Formula IV-AA and V-AA (where $A^1$=Cl) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially, equimolar amounts of compounds of Formula IV-AA and V-AA (where $A^1$=Cl) and base and substochiometric amounts of DMAP were preferably used although higher or lower amounts were used if desired. Additionally, other suitable reaction conditions for the conversion of a compound of Formula IV-AA to a compound of Formula III-AA can be found in Larock, R. C. *Comprehensive Organic Transformations*, $2^{nd}$ ed.; Wiley and Sons: New York, 1999, pp 1941-1949.

Compound of Formula I-BB is equal to compound of Formula I wherein $R^1$=$SR^4$; $X_1$ and $X_2$=CH, $X_3$ and $X_5$=N, and $X_4$, $X_6$, and $X_7$=C:

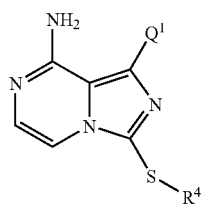

I-BB

Method C was used when preparing compounds of Formula I-BB as shown below in Scheme 9:

Method C:

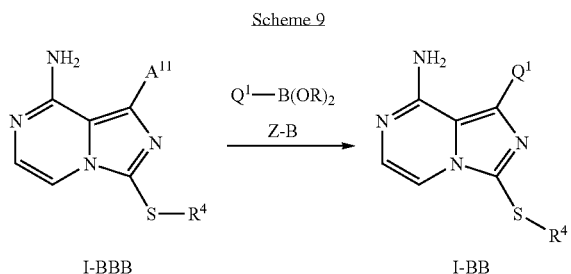

where $Q^1$ and $R^4$ are as defined previously for compound of Formula I, $A^{11}$=halogen such as Cl, Br, or I and $B(OR)_2$=suitable boronic acid/ester.

In a typical preparation of compounds of Formula I-BB, compound of Formula I-BBB was reacted with a suitable boronic acid/ester ($Q^1$-$B(OR)_2$) in a suitable solvent via typical Suzuki coupling procedures. Suitable solvents for use in the above process included, but were not limited to, ethers such as tetrahydrofuran (THF), glyme, dioxane, dimethoxyethane, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was dimethoxyethane/water. The above process was carried out at temperatures between about –78° C. and about 120° C. Preferably, the reaction was carried out between 60° C. and about 100° C. The above process to produce compounds of the present invention was preferably carried out at about atmospheric pressure although higher or lower pressures were used if desired. Substantially equimolar amounts of reactants were preferably used although higher or lower amounts were used if desired.

One skilled in the art will appreciate that alternative methods may be applicable for preparing compounds of Formula I-BB from I-BBB. For example, compound of Formula I-BBB could be reacted with a suitable organotin reagent $Q^1$-$SnBu_3$ or the like in a suitable solvent via typical Stille coupling procedures.

The compounds of Formula I-BBB of Scheme 9 were prepared as shown below in Scheme 10.

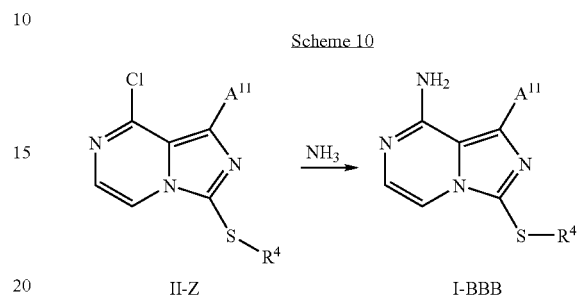

where $R^4$ is as defined previously for compound of Formula I and $A^{11}$=halogen such as Cl, Br, or I.

In a typical preparation of compounds of Formula I-BBB, compound of Formula II-Z was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvents were isopropanol and a mixture of THF and isopropanol. The above process was carried out at temperatures between about –78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II-Z of Scheme 10 were prepared as shown below in Scheme 11.

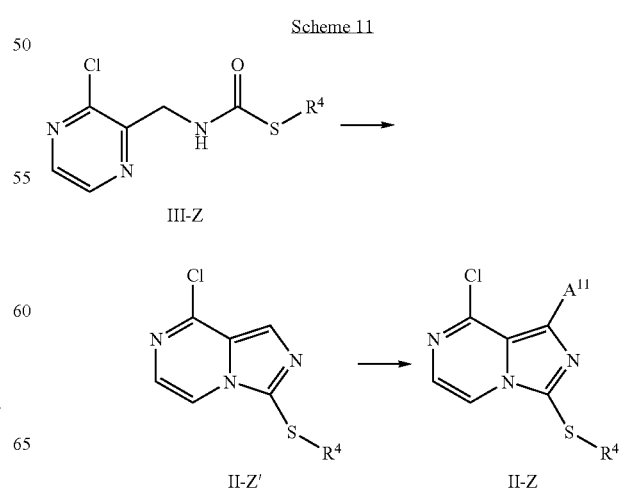

where $R^4$ is as defined previously for compound of Formula I and $A^{11}$=halogen such as Cl, Br, or I.

In a typical preparation of a compound of Formula II-Z, intermediate III-Z was converted to compound of Formula II-Z'. Intermediate of Formula III-Z was treated with POCl$_3$ in a suitable solvent at a suitable reaction temperature. Suitable solvents for use in the above process included, but were not limited to, ethers such as tetrahydrofuran (THF), glyme, and the like; acetonitrile; and chlorinated solvents such as methylene chloride (CH$_2$Cl$_2$) or chloroform (CHCl$_3$). If desired, mixtures of these solvents were used. The preferred solvents included methylene chloride and acetonitrile. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially equimolar amounts of reactants were preferably used although higher or lower amounts were used if desired. In the conversion of compound of Formula II-Z' to II-Z, suitable halogenating agents were used, but were not limited to, Br$_2$, I$_2$, Cl$_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-Z of Scheme 11 were prepared as shown below in Scheme 12:

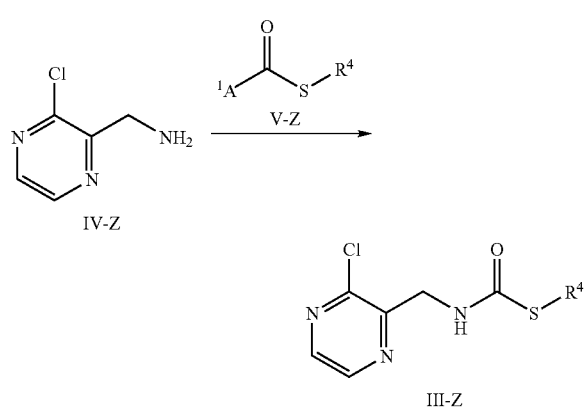

where $R^4$ is as defined previously for compound of Formula I and $A^1$=a leaving group such as chloro.

In a typical preparation, of a compound of Formula III-Z, a compound of Formula IV-Z and compound of Formula V-Z were reacted under suitable amide coupling conditions. Compounds of Formula IV-Z and V-Z (where $A^1$=Cl) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula IV-Z and V-Z (where $A^1$ Cl) and base and substochiometric amounts of DMAP were preferably used although higher or lower amounts were used if desired. The synthesis of compounds of Formula IV-Z and Z-B have been previously disclosed in WO 2005/097800A1.

In addition to Method C, the compounds of Formula I-BB can be prepared according to Method D. Method D was used when preparing compounds of Formula I-BB as shown below in Scheme 13:

Method D:

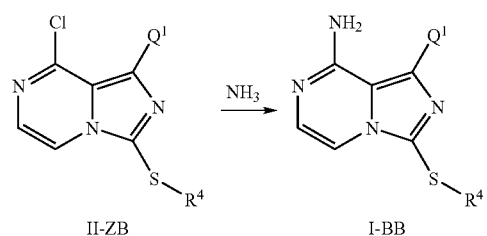

where $Q^1$ and $R^4$ are as defined previously for compound of Formula I.

In a typical preparation of compounds of Formula I-BB, compound of Formula II-ZB was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcoholics such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent was isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II-ZB of Scheme 13 were prepared as shown below in Scheme 14.

Scheme 14

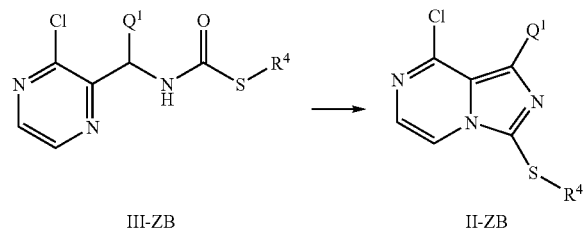

III-ZB                II-ZB where $Q^1$ and $R^4$ are as defined previously for compound of Formula I.

In a typical preparation of a compound of Formula II-ZB, intermediate III-ZB was treated with $POCl_3$ in a suitable solvent at a suitable reaction temperature. Suitable solvents for use in the above process included, but were not limited to, ethers such as tetrahydrofuran (THF), glyme, and the like; acetonitrile; and chlorinated solvents such as methylene chloride ($CH_2Cl_2$) or chloroform ($CHCl_3$). If desired, mixtures of these solvents were used. The preferred solvents included methylene chloride and acetonitrile. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-ZB of Scheme 14 were prepared as shown below in Scheme 15:

Scheme 15

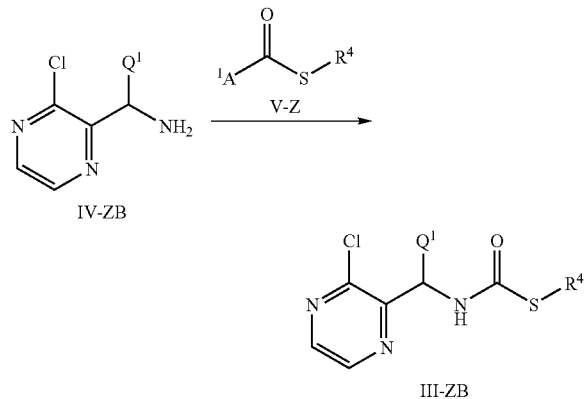

IV-ZB

III-ZB where $Q^1$ and $R^4$ are as defined previously for compound of Formula I and $A^1$=a leaving group such as chloro.

In a typical preparation, of a compound of Formula III-ZB, a compound of Formula IV-ZB and compound of Formula V-Z were reacted under suitable amide coupling conditions. Compounds of Formula IV-ZB and V-Z (where $A^1$=Cl) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula IV-ZB and V-Z (where $A^1$=Cl) and base and substochiometric amounts of DMAP were preferably used although higher or lower amounts were used if desired. The synthesis of compounds of Formula IV-ZB has been previously disclosed in WO2005/037836 and WO 2005/097800A1.

The compounds of Formula I-ZB.11 and I-BBB were prepared as shown below in Scheme 16:

Scheme 16

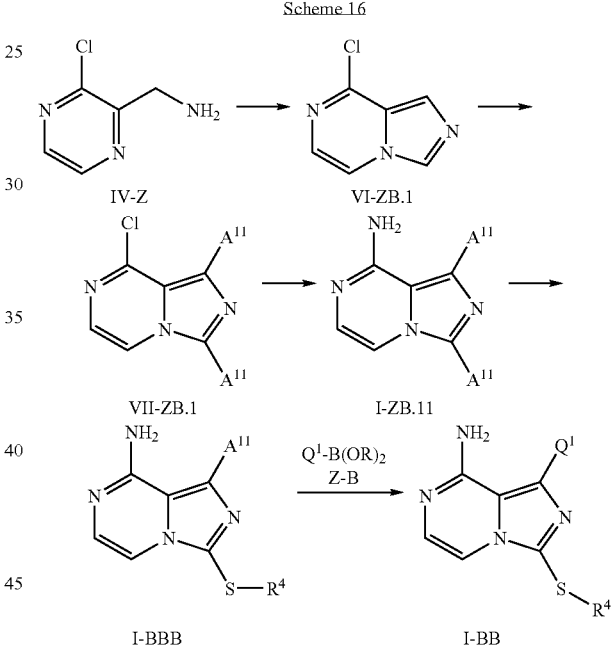

IV-Z                VI-ZB.1

VII-ZB.1            I-ZB.11

I-BBB               I-BB where $R^4$ is as defined previously for compound of Formula I, $A^{11}$=halogen such as Cl, Br, or I and $B(OR)_2$=suitable boronic acid/ester.

In a typical preparation of compound VI-ZB.1, compound IV-Z was treated with an acid or acid chloride under suitable amide coupling conditions to afford the respective amide, which when treated with $POCl_3$, underwent cyclization. Suitable amide coupling conditions have been previously described herein in Scheme 8. Suitable cyclization conditions to afford the desired imidazopyrazine have been previously described in Scheme 7. In a typical preparation of compound VII-ZB.1, compound of formula VI-ZB. I was treated with a suitable halogenating agent, such as but not limited to NBS, in a suitable solvent, such as but not limited to DMF. The above process was carried out at temperatures between about −78° C. and about 120° C. The above process to produce compounds of the present invention was preferably carried out at about atmospheric pressure although higher or lower pressures were used if desired. Substantially, equimolar amounts of reactants were preferably used although higher or lower amounts were used if desired. In a typical preparation of compound I-ZB.11, compound of formula VII-ZB.1 was treated under typical ammonolysis conditions as described previously in Scheme 1. In a typical preparation of compound I-BBB, compound of formula I-ZB.11 was treated with $HSR^4$ in a suitable solvent and suitable reaction conditions. Suitable solvents for use in the above process included, but were not limited to DMF, DMA, NMP, acetone, alcohols such as ethanol (EtOH), ethers such as tetrahydrofuran (THF), alkanes such as hexane, and also benzene, halogenated solvents such as methylene chloride ($CH_2Cl_2$), DCE, and chloroform ($CHCl_3$). If desired, mixtures of these solvents were used. The preferred solvent was DMF. Suitable bases included but were not limited to $K_2CO_3$, $Cs_2CO_3$, $Ag_2CO_3$, and NaH. The preferred base was NaH. The above process was carried out at temperatures between about $-78°$ C. and about $120°$ C. Preferably, the reaction was carried out between rt and about $70°$ C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula I-BB.2 and I-BB were prepared as shown below in Scheme 17 (wherein compound I-BB.1 and I-BB.2 are compounds of Formula I-BB where $R^4$=Me and H, respectively):

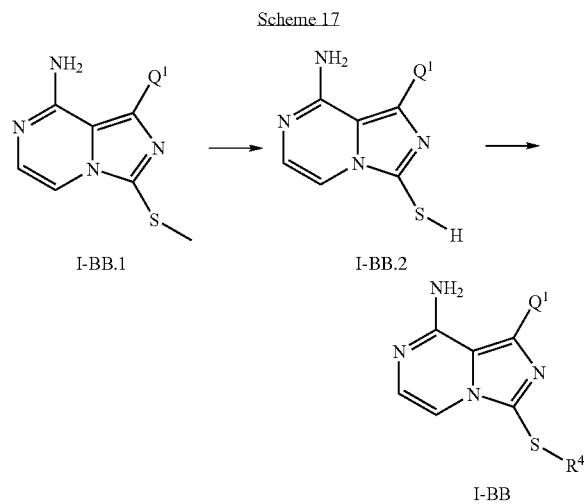

Scheme 17 where $Q^1$ and $R^4$ are as defined previously for compound of Formula I.

In a typical preparation of a compound of Formula I-BB, an intermediate of Formula I-BB.1 was treated with an acid such as but not limited to HBr, HCl, trifluoroacetic acid, acetic acid, phosphoric acid and the like, or more preferably, a combination of acids such as HBr and acetic acid to afford compound I-BB.2. Compound I-BB.2 was then treated with an alkylhalide ($R^4$-$A^{11}$) in the presence of a suitable base in a suitable solvent at a suitable reaction temperature. Suitable solvents for use in the above process included, but were not limited to DMF, DMA, NMP, acetone, alcohols such as ethanol (EtOH), ethers such as tetrahydrofuran (THF), alkanes such as hexane, and also benzene, halogenated solvents such as methylene chloride ($CH_2Cl_2$), DCE, and chloroform ($CHCl_3$). If desired, mixtures of these solvents were used.

Suitable bases included but were not limited to DIEA, $K_2CO_3$, $Cs_2CO_3$, $Ag_2CO_3$, and NaH. The above process was carried out at temperatures between about $-78°$ C. and about $120°$ C. The above process to produce compounds of the present invention was preferably carried out at about atmospheric pressure although higher or lower pressures were used if desired. Substantially, equimolar amounts of reactants were preferably used although higher or lower amounts were used if desired.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Green and P. G. M. Wutz, John Wiley and Sons, 1989.

The following examples are intended to illustrate and not to limit the scope of the present invention.

General Experimental Information:

All melting points were determined with a Mel-Temp II apparatus and are uncorrected. Commercially available anhydrous solvents and HPLC-grade solvents were used without further purification. $^1$H NMR and $^{13}$C NMR spectra were recorded with Varian or Bruker instruments (400 MHz for $^1$H, 100.6 MHz for $^{13}$C) at ambient temperature with TMS or the residual solvent peak as internal standards. The line positions or multiplets are given in ppm ($\delta$) and the coupling constants (J) are given as absolute values in Hertz, while the multiplicities in $^1$H NMR spectra are abbreviated as follows: s (singlet), d (doublet), t (triplet), q (quartet), quint (quintet), m (multiplet), $m_c$ (centered multiplet), br (broadened), AA'BB'. The signal multiplicities in $^{13}$C NMR spectra were determined using the DEPT135 pulse sequence and are abbreviated as follows: +(CH or $CH_3$), -($CH_2$), $C_{quart}$(C). LC/MS analysis was performed using a Gilson 215 autosampler and Gilson 819 autoinjector attached to a Hewlett Packard HP1100 and a MicromassZQ mass spectrometer (also referred to as "OpenLynx"), or a Hewlett Packard HP1050 and a Micromass Platform II mass spectrometer. Both setups used XTERRA MS C18 5μ 4.6×50 mm columns with detection at 254 nm and electrospray ionization in positive mode. For mass-directed purification (MDP), a Waters/Micromass system was used.

Analytical HPLC Conditions:

Unless otherwise stated, all HPLC analyses were run on a Micromass system with a XTERRA MS C18 5μ 4.6×50 mm column and detection at 254 nm. Table A below lists the mobile phase, flow rate, and pressure.

TABLE A

| Time (min) | % CH$_3$CN | 0.01% HCOOH in H$_2$O % | Flow (mL/min) | Pressure (psi) |
|---|---|---|---|---|
| 0.00 | 5 | 95 | 1.3 | 400 |
| 4.00 | 100 | 0 | 1.3 | 400 |
| 5.50 | 100 | 0 | 1.3 | 400 |
| 6.00 | 5 | 95 | 1.3 | 400 |
| 7.00 | 5 | 95 | 1.3 | 400 |

Semipreparative HPLC Conditions:

Where indicated as "purified by Gilson HPLC", the compounds of interest were purified by a preparative/semi-preparative Gilson HPLC workstation with a Phenomenex Luna 5μ C18 (2) 60×21 20 MM 5μ column and Gilson 215 liquid handler (806 manometric module, 811C dynamic mixer, detection at 254 nm). Table B lists the gradient, flow rate, time, and pressure.

TABLE B

| Time (min) | % CH$_3$CN | 0.01% HCOOH in H$_2$O % | Flow (mL/min) | Pressure (psi) |
|---|---|---|---|---|
| 0.00 | 5 | 95 | 15 | 1000 |
| 15.00 | 60 | 40 | 15 | 1000 |
| 15.10 | 100 | 0 | 15 | 1000 |
| 19.00 | 100 | 0 | 15 | 1000 |
| 20.00 | 5 | 95 | 15 | 1000 |

EXAMPLE 1

1-(3-Benzyloxy-phenyl)-3-ethoxy-imidazo[1,5-a]pyrazin-8-ylamine

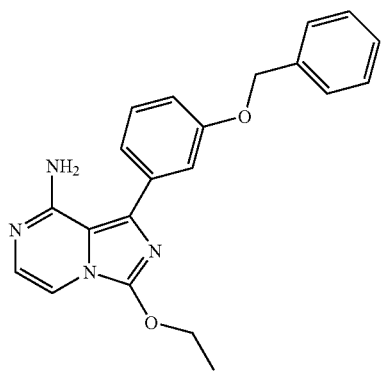

A solution of 1-(3-benzyloxy-phenyl)-8-chloro-3-ethoxy-imidazo[1,5-a]pyrazine (20.0 mg, 0.05 mmol) in i-PrOH (5 mL) was saturated with NH$_3$ at −20° C. and heated in a Parr pressure vessel to 110° C. for 72 h. The reaction was concentrated in vacuo, partitioned between DCM and H$_2$O and separated. The aqueous layer was washed with DCM (3×) and the combined organic layers were washed with brine (1×), dried over Na$_2$SO$_4$, filtered and concentrated in vacuo and purified by chromatography on silica gel [eluting with 2% EtOAc in DCM] to yield the desired product as an off-white solid; $^1$H NMR (CDCl$_3$, 400 MHz) δ 1.45 (t, J=7.2 Hz, 3H), 4.58 (q, J=7.2 Hz, 2H), 4.91 (brs, 2H), 5.10 (s, 2H), 6.86 (d, J=4.8 Hz, 1H), 6.95-6.99 (m, 1H), 7.04 (d, J=5.2 Hz, 1H), 7.17-7.21 (m, 2H), 7.26-7.43 (m, 7H); MS (ES+): m/z=361.19 (100) [MH+], HPLC: t$_R$=2.36 min (MicromassZQ, polar_5 min).

a) 1-(3-Benzyloxy-phenyl)-8-chloro-3-ethoxy-imidazo[1,5-a]pyrazine

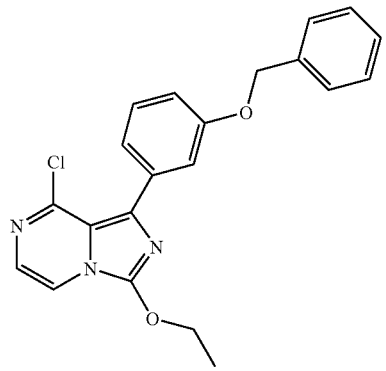

A solution of 1-(3-benzyloxy-phenyl)-8-chloro-2H-imidazo[1,5-a]pyrazin-3-one (50.0 mg, 0.14 mmol) and silver carbonate (85 mg, 0.31 mmol) in anhydrous EtOH (1 mL) was charged with iodoethane (0.012 mL, 0.15 mmol) and stirred at rt for 48 h. The reaction mixture was partitioned between DCM and H$_2$O and separated. The aqueous layer was washed with DCM (3×) and the combined organic layers were washed with brine (1×), dried over Na$_2$SO$_4$, filtered and concentrated in vacuo and the crude material was purified by chromatography on silica gel [eluting with 2% EtOAc in DCM], to yield the desired product as a yellow oil/gum; $^1$H NMR (CDCl$_3$, 400 MHz) δ 1.51 (t, J=7.2 Hz, 3H), 4.68 (q, J=7.2 Hz, 2H), 5.13 (s, 2H), 7.00-7.05 (m, 1H), 7.13 (d, J=5.2 Hz, 1H), 7.27-7.48 (m, 9H); MS (ES+) m/z=380.07 (100) [MH+], HPLC: t$_R$=4.04 min (MicromassZQ, polar_5 min).

b) 1-(3-Benzyloxy-phenyl)-8-chloro-2H-imidazo[1,5-a]pyrazin-3-one

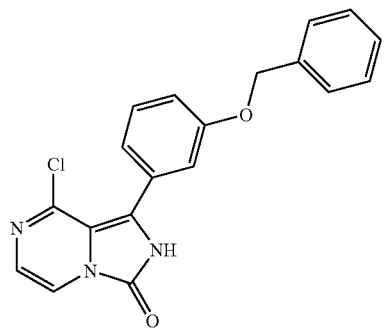

A solution C-(3-benzyloxy-phenyl)-C-(3-chloro-pyrazin-2-yl)-methylamine hydrochloride (5 g, 13.8 mmol) and CDI (2.46 g, 15.19 mmol) in anhydrous THF (70 mL) was charged with DIEA (2.40 mL, 13.8 mmol) and heated to 80° C. for 1 h and then concentrated in vacuo. The crude material was partitioned between EtOAc and H$_2$O and separated. The aqueous layer was washed with EtOAc (3×) and the combined organic layers were washed with brine (1×), dried over Na$_2$SO$_4$, filtered and concentrated in vacuo. The crude was purified by chromatography on silica gel [eluting with 5% MeOH in DCM], to yield the desired product as a yellow solid; $^1$H NMR (DMSO-d$_6$, 400 MHz) δ 5.17 (s, 2H), 6.86 (d, J=5.2 Hz, 1H), 7.10-7.16 (m, 2H), 7.22-7.23 (m, 1H), 7.34-7.48 (m, 6H), 7.50 (d, J=7.9 Hz, 1H); MS (ES+): m/z=352.15 (100) [MH⁺], HPLC: $t_R$=3.19 min (MicromassZQ, polar_5 min)

c) C-(3-Benzyloxy-phenyl)-C-(3-chloro-pyrazin-2-yl)-methylamine hydrochloride

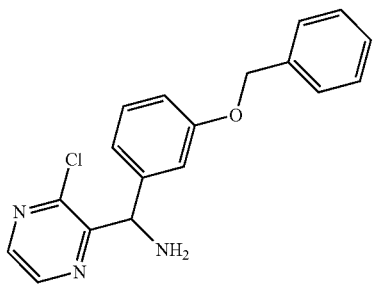

2-[(3-benzyloxy-phenyl)-(3-chloro-pyrazin-2-yl)-methyl]-isoindole-1,3-dione (2.76 g, 6.05 mmol) was dissolved in EtOH (12 mL) and CH₂Cl₂ (4 mL) charged with N₂H₄ (0.57 mL, 18.16 mmol) and allowed to react for 16 h at rt. The white precipitate was filtered and washed with EtOAc. The filtrate and organic washings were concentrated in vacuo, and purified via HPFC using a 100 g Jones silica gel column (50% EtOAc: Hex to 5% MeOH: CH₂Cl₂) to yield the desired product as a reddish oil; ¹H NMR (CDCl₃, 400 MHz) δ 5.04 (s, 2H), 5.52 (s, 1H), 6.85-6.98 (m, 2H), 7.21-7.26 (m, 2H), 7.30-7.41 (m, 5H), 8.26 (d, 1H, J=2.5 Hz), 8.52 (d, 1H, J=2.5 Hz); MS (ES) 326.25 (M+1), 328.23 (M+3), 329.24 (M+4).

d) 2-[(3-Benzyloxy-phenyl)-(3-chloro-pyrazin-2-yl)-methyl]-isoindole-1,3-dione

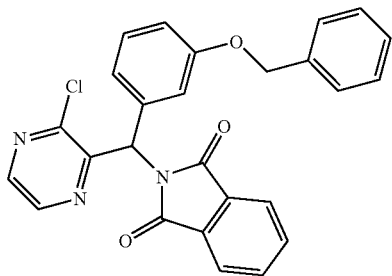

(3-Chloro-pyrazin-2-yl)-(3-benxyloxy-phenyl)-methanol (2.00 g, 6.12 mmol), triphenylphosphine (1.80 g, 6.70 mmol), and phthalimide (986 mg, 6.70 mmol) were dissolved in THF (20.0 mL) at rt. The reaction mixture was charged with DIAD (1.30 mL, 6.70 mmol) dropwise and allowed to react for 24 h at rt (TLC analysis (20% EtOAc:Hex)). The crude product was purified by applying HPFC with a 100 g Jones silica gel column (20% EtOAc:Hex) to yield the desired product as a pale yellow solid; ¹H NMR (CDCl₃, 400 MHz) δ 5.02 (s, 2H), 6.41 (brs, 1H), 6.87-6.97 (m, 3H), 7.26-7.40 (m, 3H), 7.72-7.76 (m, 2H), 7.83-7.86 (m, 2H), 8.34 (d, 1H, J=2.4 Hz), 8.55 (d, 1H, J=2.4 Hz).

e) (3-Chloro-pyrazin-2-yl)-(3-benzyloxy-phenyl)-methanol

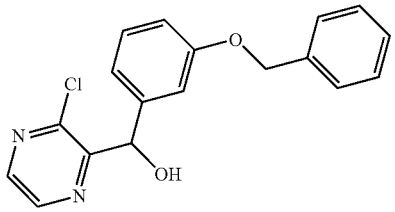

A THF (20 mL) solution of 2M n-BuLi in cyclohexanes was cooled to −78° C. and charged with 2,2,6,6-tetramethylpiperidine (1.8 mL, 10.48 mmol). The reaction vessel was removed from the cooling bath and allowed to warm to 0° C. for 15 min, then cooled back to −78° C. and charged with 2-chloropyrazine (1.0 g, 8.73 mmol) dropwise. The reaction was allowed to react for 15 min, and charged with a 10.0 mL THF solution of 3-benzyloxybenzaldehyde (2.0 g, 9.60 mmol) slowly at −78° C. The reaction was allowed to react for 2 h (TLC analysis (30% EtOAc:Hex)) and quenched with HCl$_{conc.}$ (2.0 mL), and H₂O (30.0 mL). The crude product was extracted from the aqueous/THF layer 4× with CH₂Cl₂. The organic layers were combined and washed 1× with H₂O, 1×brine, dried over Na₂SO₄ and concentrated in vacuo, to yield the crude product as a brown oil. High performance flash chromatography (HPFC) with a 70 g Jones silica gel column (30% EtOAc:Hex) was applied to yield the desired product as a pale yellow solid; ¹H NMR (CDCl₃, 400 MHz) δ 5.01 (s, 3H), 6.00 (s, 2H), 6.90-6.96 (m, 3H), 7.23-7.41 (m, 6H), 8.36 (d, 1H, J=2.4 Hz), 8.54 (d, 1H, J=2.5 Hz); MS (ES) 327.16 (M+1), 329.16 (M+3).

EXAMPLE 2

3-Ethoxy-1-(2-phenyl-quinolin-7-yl)-imidazo[1,5-a]pyrazin-8-ylamine

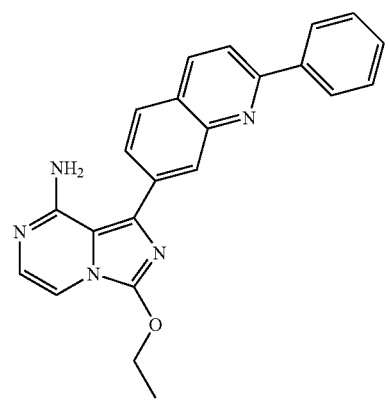

7-(8-Chloro-3-ethoxy-imidazo[1,5-a]pyrazin-1-yl)-2-phenyl-quinoline (20.0 mg, 0.050 mmol) was dissolved into a 80 mL sealed tube with isopropyl alcohol (1.0 mL, 3.0 mmol). The solution was cooled to −20° C. and charged with ammonia gas. The reaction was heated to 110 IC for 72 hours. The reaction was then cooled, concentrated in vacuo and dissolved with CH₂Cl₂. The crude product was purified via silica gel column chromatography, (Jones, 2.0 gram column; 100% EtOAc) to yield the title compound as a yellow solid; MS (ES+): m/z 382.08 (90) [MH$^+$], 383.09 (30) [MH$^{++}$]. HPLC: $t_R$=2.26 min (OpenLynx, polar_5 min); 1H NMR (400 MHz, CHLOROFORM-d) δ ppm 1.52 (t, J=7.07 Hz, 3H), 4.66 (q, J=7.07 Hz, 2H), 6.96 (d, J=5.05 Hz, 1H), 7.13 (d, J=5.05 Hz, 1H), 7.34-7.63 (m, 3H), 7.75-8.01 (m, 3H), 8.10-8.32 (m, 3H), 8.40 (s, 1H).

a) 7-(8-Chloro-3-ethoxy-imidazo[1,5-a]pyrazin-1-yl)-2-phenyl-quinoline

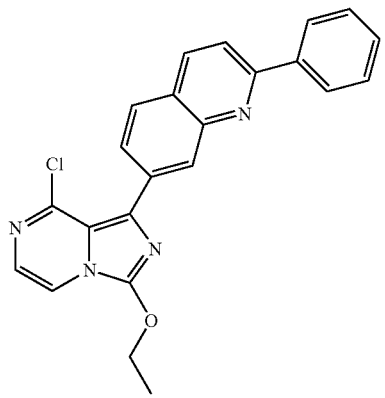

A 80 mL sealed tube is charged with 8-chloro-1-(2-phenyl-quinolin-7-yl)-2H-imidazo[1,5-a]pyrazin-3-one (50.00 mg, 0.1341 mmol), silver carbonate (74 mg, 0.27 mmol), anhydrous ethanol (2.00 mL, 0.034 mol), 1,3-dimethyl-3,4,5,6-tetrahydro-2(1H)-pyrimidinone (0.002 mL, 0.01 mmol), and iodoethane (0.012 mL, 0.15 mmol). The reaction was sealed under an atmosphere of nitrogen and heated at 40° C. for 24 hours. The reaction was cooled and filtered. Water and EtOAc were added and the organic layer was isolated, dried over sodium sulfate, filtered and concentrated in vacuo to yield a yellow gum. The crude product was purified via silica gel column chromatography, (Jones, 5 gram column eluting with 50% EtOAc: Hex) to yield the title compound as a yellow gum; MS (ES+): m/z 401.03 (100) [MH$^+$], 402.98 (30) [MH$^{+++}$]; HPLC: $t_R$=4.13 min (OpenLynx, polar_5 min); $^1$HNMR (400 MHz, CHLOROFORM-d) δ ppm 1.41-1.72 (m, 3H), 4.55-4.86 (m, 2H), 7.18 (d, J=4.80 Hz, 1H), 7.38-7.65 (m, 4H), 7.75-8.00 (m, 3H), 8.09-8.33 (m, 3H), 8.52 (br. s., 1H).

b) 8-Chloro-1-(2-phenyl-quinolin-7-yl)-2H-imidazo[1,5-a]pyrazin-3-one

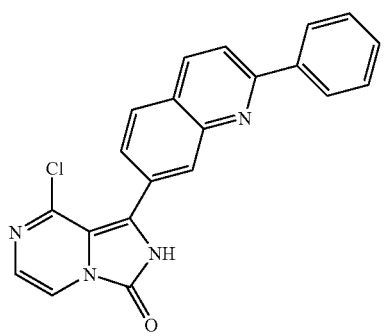

C-(3-Chloro-pyrazin-2-yl)-C-(2-phenyl-quinolin-7-yl)-methylamine (2.0 g, 5.8 mmol) was dissolved in anhydrous THF (35.0 mL), followed by the addition of DIPEA (1.21 mL, 6.92 mmol) at rt. The dark brown solution was then charged with para-nitrophenyl chloroformate (1.28 g, 6.34 mmol) at rt, and warmed to 45° C. for 17 h. The crude reaction was concentrated in vacuo and dissolved with EtOAc and water. Yellow precipitate crashed out of solution and was filtered. The solid was washed with hexanes and dried under vacuum to yield the title compound as a yellow solid; MS (ES+): m/z 373.04 (100) [MH$^+$], 375.00 (30) [MH$^{+++}$]; HPLC: $t_R$=3.15 min (OpenLynx, polar_5 min); $^1$HNMR (400 MHz, DMSO-d$_6$) δ ppm 6.80-7.05 (m, 2H), 7.43-7.66 (m, 4H), 7.79 (dd, J=8.34, 1.77 Hz, 1H), 8.02-8.17 (m, 2H), 8.19-8.35 (m, 4H), 8.53 (d, J=8.59 Hz, 1H).

c) C-(3-Chloro-pyrazin-2-yl)-C-(2-phenyl-quinolin-7-yl)-methylamine (compound of Formula IV where Q$^1$=2-phenylquinolin-7-yl)

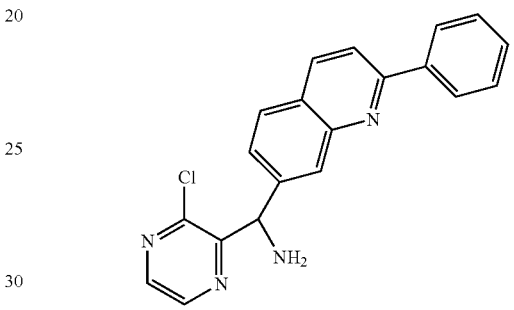

A solution of 2-[(3-chloropyrazin-2-yl)-(2-phenylquinolin-7-yl)-methyl]-isoindole-1,3-dione (1.536 g, 3.22 mmol) and anhydrous hydrazine (335 μL, 342 mg, 10.7 mmol) in EtOH (2 mL)/CH$_2$Cl$_2$ (12 mL) is stirred at rt overnight. The white precipitate formed is filtered off and washed with CH$_2$Cl$_2$. The combined filtrate and washings are concentrated in vacuo, the residue is suspended in CDCl$_3$ and filtered (0.45 μM pore size), and the filtrate is concentrated in vacuo to obtain the title compound as yellow foam, which is used for the next step without further purification; $^1$H NMR (CDCl$_3$, 400 MHz): δ2.4 (brs, 2H), 5.79 (s, 1H), 7.43-7.55 (m, 3H), 7.61 (dd, J=1.8, 8.6 Hz, 1H), 7.81 (d, J=8.4 Hz, 1H), 7.86 (d, J=8.4 Hz, 1H), 8.06 (d, J=1.2 Hz, 1H), 8.10-8.15 (m, 2H), 8.19 (d, J=8.8 Hz, 1H), 8.31 (d, J=2.4 Hz, 1H), 8.60 (d, J=2.4 Hz, 1H); MS (ES+):m/z347.0/349.0(30/10) [MH$^+$], 330.0/332.0 (18/6) [MH$^+$-NH$_3$]; HPLC: $t_R$=2.1 min (MicromassZQ, polar_5 min).

d) 2-[(3-Chloro-pyrazin-2-yl)-(2-phenyl-quinolin-7-yl)-methyl]-isoindole-1,3-dione

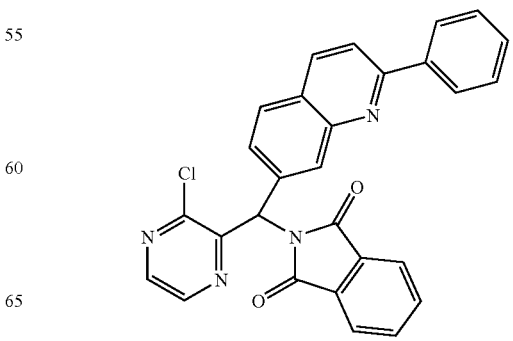

To a suspension of (3-chloropyrazin-2-yl)-(2-phenylquinolin-7-yl)-methanol (1.215 g, 3.49 mmol), phthalimide (566 mg, 3.85 mmol), and PS-PPh₃ (loading 2.12 mmol/g; 3.29 g, 6.97 mmol) in dry THF (40 mL), cooled by ice/water, is added DIAD (830 μL, 852 mg, 4.22 mmol). The cooling bath is removed and the flask is vortexed at rt for 1 d. More phthalimide (50 mg, 0.34 mmol), PS-PPh₃ (300 mg, 0.636 mmol), and DIAD (80 μL, 82 mg, 0.41 mmol) are added, and vortexing is continued for 2 d. The resin is filtered off on a glass frit (porosity M) and washed with $CH_2Cl_2$. The combined filtrates and washings are concentrated in vacuo and chromatographed on silica gel [Jones Flashmaster, 50 g/150 mL cartridge, eluting with $CH_2Cl_2$ (1-22)→2% EtOAc in $CH_2Cl_2$ (23-38)→5% (39-61)], mixed fractions are combined and chromatographed again [50 g/150 mL cartridge, eluting with $CH_2Cl_2$ (1-22)→2% EtOAc in $CH_2Cl_2$ (23-33)→3% (34-55)→5% (56-68)] to obtain the title compound as white foam; ¹H NMR (CDCl₃, 400 MHz): δ 7.14 (s, 1H), 7.43-7.55 (m, 3H), 7.72-7.79 (m, 3H), 7.82-7.90 (m, 4H), 8.09 (s, 1H), 8.09-8.14 (m, 2H), 8.22 (d, J=8.8 Hz, 1H), 8.40 (d, J=2.4 Hz, 1H), 8.51 (d, J=2.4 Hz, 1H); MS (ES+): m/z 476.9/478.9 (100/38) [MH⁺]; HPLC: $t_R$=3.5 min (MicromassZQ, nonpolar_5 min).

e) (3-Chloropyrazin-2-yl)-(2-phenylquinolin-7-yl)-methanol

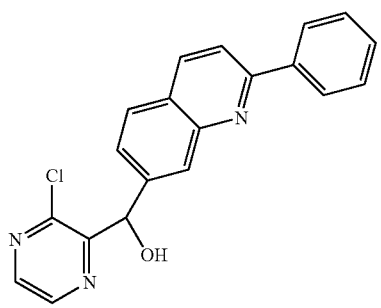

To a solution of 2,2,6,6-tetramethylpiperidine (0.820 mL, 0.686 g, 4.86 mmol) in dry THF (15 mL), cooled by $CO_2$(s)/acetone, is added nBuLi (2.5M in hexanes; 1.95 mL, 4.88 mmol). The cooling bath is replaced with an ice/water bath for 15 min, and then the solution is re-cooled to −78° C. After 5 min, a solution of 2-chloropyrazine (0.370 mL, 0.475 g, 4.14 mmol) in THF (0.5 mL) is added. After 25 min, a solution of 2-phenylquinoline-7-carbaldehyde (890 mg, 3.82 mmol) in dry THF (7 mL) is added slowly over 5 min from a syringe which is then rinsed with THF (1 mL), and the mixture is stirred at −78° C. for 2 h and then warmed up to 0° C. for 0.5 h. The reaction is quenched by adding citric acid (0.25M aqueous solution). The mixture is extracted with EtOAc (4×30 mL), and the combined EtOAc extracts are washed with water, sodium bicarb solution, and brine and dried over MgSO₄. The crude material is chromatographed on silica gel [Jones Flashmaster, 50 g/150 mL cartridge, eluting with $CH_2Cl_2$ (4×50 mL, then 1-16)→2% EtOAc in $CH_2Cl_2$ (17-30)→5% (31-59)→7% (60-85)→10% (86-110)] to obtain the title compound as an off-white foam; ¹H NMR (CDCl₃, 400 MHz) δ 4.80 (d, J=7.6 Hz, 1H), 6.25 (d, J=7.6 Hz, 1H), 7.43-7.56 (m, 3H), 7.58 (dd, J=1.8, 8.2 Hz, 1H), 7.83 (d, J=8.4 Hz, 1H), 7.87 (d, J=8.4 Hz, 1H), 8.06 (brs, 1H), 8.10-8.15 (m, 2H), 8.20 (d, J=8.4 Hz, 1H), 8.41 (d, J=2.4 Hz, 1H), 8.62 (d, J=2.4 Hz, 1H); MS (ES+): m/z 348.0/350.0 (100/37) [MH⁺]; HPLC: $t_R$=3.3 min (MicromassZQ, polar_5 min).

f) 2-Phenylquinoline-7-carbaldehyde

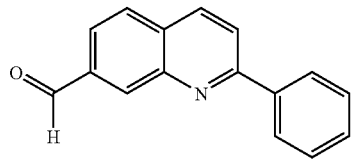

A mixture of 7-methyl-2-phenylquinoline (2.49 g, 11.4 mmol) and selenium dioxide (1.92 g, 17.3 mmol, 1.5 eq.) is heated to 160° C. (bath temp.) for 22 h. The cooled melt is suspended in $CH_2Cl_2$ with the aid of sonication and filtered through Celite and then through a plug of silica gel. This effectively removes the red color and the major lower spots. The material thus obtained is crystallized from hexanes/CHCl₃, yielding a pale beige solid, mp. 108° C. The mother liquor is concentrated and chromatographed on silica gel [Jones Flashmaster, 50 g/150 mL cartridge, eluting with hexanes:$CH_2Cl_2$ 1:1 (1-25)→1:3 (26-53)→$CH_2Cl_2$ (54-73)→3% EtOAc in $CH_2Cl_2$ (74-85)] to obtain the title compound as a pale yellow solid, mp. 109° C.; ¹H NMR (CDCl₃, 400 MHz) δ 7.48-7.60 (m, 3H), 7.94 (d, J=8.8 Hz, 1H), 8.01-8.05 (m, 2H), 8.18-8.23 (m, 2H), 8.29 (d, J=8.8 Hz, 1H), 8.64 (s, 1H), 10.26 (s, 1H) MS (ES+): m/z 234.2 (100) [MH⁺]; HPLC: $t_R$=3.0 min (MicromassZQ, nonpolar_5 min).

g) 7-Methyl-2-phenylquinoline

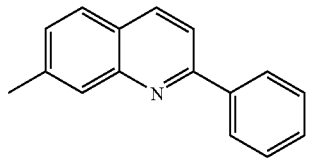

To a solution of 7-methylquinoline (1.63 g, 11.4 mmol) in dry THF (10 mL), cooled by ice/water, is added phenyllithium (1.9M in cyclohexane/ether 70/30, 6.0 mL, 11.4 mmol) dropwise over 5 min. After 15 min, the cooling bath is removed, and the solution is stirred at rt for 5h. The reaction is quenched by adding MeOH, and stirring is continued overnight. Water is added, the mixture is extracted with EtOAc (3×35 mL), and the combined extracts are dried over MgSO₄. The drying agent is filtered off, and air is bubbled into the solution for 7 d. The solvent is evaporated; the residue is dissolved in warm (≈50° C.) EtOAc/hexanes and filtered warm. The filtrate is concentrated and dried in vacuo to obtain the crude title compound that is used directly for the next step. Further purification is possible by chromatography on silica gel (Jones Flashmaster, eluting with hexanes:EtOAc 3:1→2: 1→1:1); ¹H NMR (CDCl₃, 400 MHz) δ 2.58 (s, 3H), 7.31 (d, J=3.7 Hz, 1H), 7.36-7.49 (m, 1H), 7.52 (t, J=8.0 Hz, 2H), 7.72 (d, J=8.2 Hz, 1H), 7.82 (d, J=8.2 Hz, 1H), 7.96 (s, 1H), 8.16

(t, J=8.0 Hz, 2H); MS (ES+): m/z 220.3 (100) [MH+]; HPLC: $t_R$=2.7 min (Platform II, nonpolar__5 min).

EXAMPLE 3

8-Amino-1-(3-benzyloxy-phenyl)-imidazo[1,5-a]pyrazine-3-carboxylic acid amide

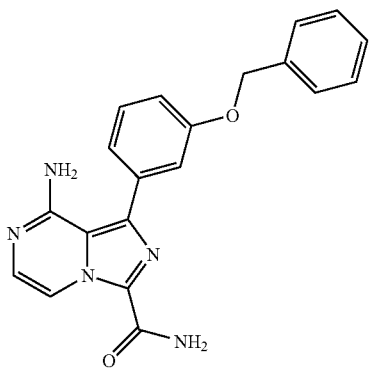

A solution of 1-(3-benzyloxy-phenyl)-8-chloro-imidazo[1,5-a]pyrazine-3-carboxylic acid ethyl ester (100 mg, 0.245 mmol) in anhydrous iPrOH (14 mL) was saturated with NH$_3$ at −30° C. and heated to 110° C. in a Parr pressure vessel for 20 hr. The reaction mixture was concentrated in vacuo and partitioned between DCM and water and separated. The aqueous layer was washed with DCM (3×) and the combined organic layers were washed with brine (1×), dried over Na$_2$SO$_4$, filtered, and concentrated in vacuo. The crude material was dry loaded using hydromatrix and the material was purified by chromatography on silica gel [eluting with 3% MeOH in DCM], resulting in the title compound as an off-white solid; $^1$H NMR (DMSO-d$_6$, 400 MHz) δ 5.08 (s, 2H), 6.13 (brs, 2H), 7.05-7.10 (m, 1H), 7.15 (m, 1H), 7.18 (d, J=4.8 Hz, 1H), 7.24-7.31 (m, 2H), 7.32-7.44 (m, 5H), 7.62 (brs, 1H), 7.91 (brs, 1H), 8.54 (d, J=4.8 Hz, 1H); MS (ES+): m/z=360.3 (100) [MH+], HPLC: $t_R$=2.33 min (MicromassZQ, polar__5 min).

a) 1-(3-Benzyloxy-phenyl)-8-chloro-imidazo[1,5-a]pyrazine-3-carboxylic acid ethyl ester

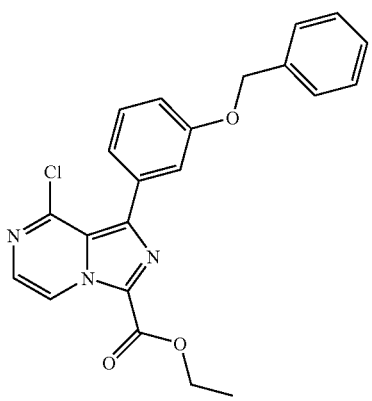

A solution of N-[(3-benzyloxy-phenyl)-(3-chloro-pyrazin-2-yl)-methyl]-oxalamic acid ethyl ester (50 mg, 0.12 mmol) in POCl$_3$ (2 mL) was heated to 55° C. for 17.5 h. Very little reaction occurred therefore DMF (3 drops) was added to reaction mixture and heated to 75° C. overnight. The brown reaction mixture was allowed to cool to rt, concentrated in vacuo and then quenched with 2M NH$_3$ in i-PrOH at 0° C. until the pH was basic. The reaction mixture was concentrated in vacuo and the crude material was purified by chromatography on silica gel [eluting with 2% EtOAc in DCM], resulting in the title compound as an off-white solid; $^1$H NMR (CDCl$_3$, 400 MHz) δ 1.48 (t, J=7.2 Hz, 3H), 4.56 (q, J=7.2 Hz, 2H), 5.13 (s, 2H), 7.05-7.09 (m, 1H), 7.22-7.29 (m, 2H), 7.29-7.47 (m, 6H), 7.67 (d, J=5.2 Hz, 1H), 9.15 (d, J=5.2 Hz, 1H); MS (ES+): m/z=408.07 (100) [MH+], HPLC: $t_R$=3.88 min (MicromassZQ, polar__5 min).

b) N-[(3-Benzyloxy-phenyl)-(3-chloro-pyrazin-2-yl)-methyl]-oxalamic acid ethyl ester

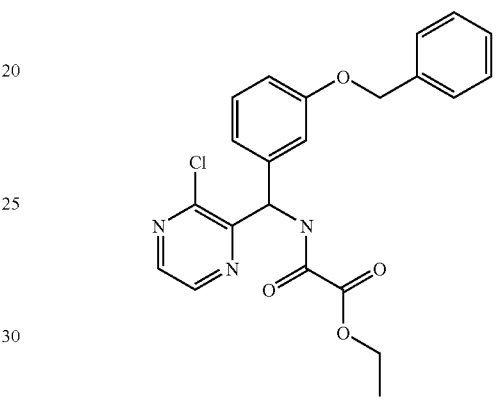

A solution of C-(3-benzyloxy-phenyl)-C-(3-chloro-pyrazin-2-yl)-methylamine-hydrochloride (500 mg, 1.42 mmol) in THF (5 mL) was charged with ethyl oxalyl chloride (0.173 mL, 1.56 mmol) and cooled to 0° C. This solution was charged with DIEA (0.618 mL, 3.55 mmol) and stirred at rt for 0.5 h. The crude product was concentrated in vacuo and was partioned in DCM and water and separated. The aqueous layer was washed with DCM (3×) and the combined organic layers were washed with brine (1×), dried over Na$_2$SO$_4$, filtered, and concentrated in vacuot. The crude material was purified by chromatography on silica gel [eluting with 5% EtOAc in DCM], resulting in the title compound as an off white solid; $^1$H NMR (CDCl$_3$, 400 MHz) δ 1.38 (t, J=7.6 Hz, 3H), 4.35 (q, J=7.2 Hz, 2H), 5.03 (s, 2H), 6.50 (d, J=8.4 Hz, 1H), 6.88-6.93 (m, 1H), 6.95-7.00 (m, 2H), 7.23 (t, J=8.0 Hz, 1H), 7.29-7.43 (m, 5H), 8.38 (d, J=5.2 Hz, 1H), 8.58 (d, J=5.2 Hz, 1H), 8.75 (brd, J=Hz, 1H); MS (ES+): m/z=426.06 (100) [MH+], HPLC: $t_R$=3.62 min (MicromassZQ, polar__5 min).

EXAMPLE 4

1-(1H-Indol-2-yl)-3-methylsulfanyl-imidazo[1,5-a]pyrazin-8-ylamine

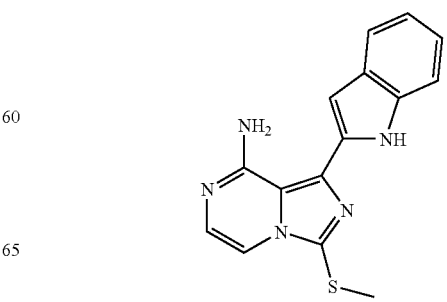

To a suspension of 1-iodo-3-methylsulfanyl-imidazo[1,5-a]pyrazin-8-ylamine (612 mg, 0.00200 mol) in 1,4-dioxane (20 mL) and water (5 mL) were added 1-Boc-indole-2-boronic acid (570 mg, 0.0022 mol), potassium carbonate (830 mg, 0.0060 mol) and [1,1'-bis(diphenylphosphino)ferrocene] dichloropalladium(II), complex with dichloromethane (1:1) (80 mg, 0.0001 mol). The flask was evacuated and refilled with nitrogen (3×). The mixture was heated at 100° C. overnight. LC-MS showed the reaction to be incomplete. Another 80 mg of PdCl$_2$(dppf) was added and the mixture was heated at 100° C. overnight. LC-MS showed the reaction was complete. The mixture was diluted with ethyl acetate (100 mL) and methanol (5 mL); the insoluble solid was filtered off through a pad of celite. The filtrate was washed with brine (20 mL), and dried over anhydrous sodium sulfate. The crude material was purified by silica gel chromatography (Hex: EtOAc=30:70→EtOAc:MeOH=98:2) to give the title compound as a yellow solid. LC-MS (ES, Pos.): 296 [MH$^+$]; $^1$H-NMR (DMSO-d$_6$): δ 2.64 (s, 3H), 6.58 (br s, 2H), 6.70 (d, J=1.5 Hz, 1H), 7.04 (t, J=7.4 Hz, 1H), 7.13 (m, 1H), 7.18 (d, J=4.8 Hz, 1H), 7.45 (d, J=8.1 Hz, 1H), 7.53 (d, J=4.8 Hz, 1H), 7.60 (d, J=7.8 Hz, 1H), 11.60 (s, 1H).

EXAMPLE 5

1-(8-Fluoro-2-phenyl-quinolin-7-yl)-3-methylsulfanyl-imidazo[1,5-a]pyrazin-8-ylamine

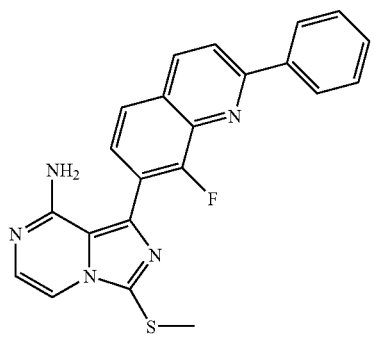

Prepared according to Example 4 above except 8-fluoro-2-phenyl-7-(4,4,5,5-tetramethyl-[1,3,2]dioxaborolan-2-yl)-quinoline (described in WO 2005/097800) was used instead of 1-Boc indole-2-boronic acid; LC-MS (ES, Pos.): 402 [MH$^+$]; $^1$H NMR (400 MHz, CDCl$_3$) δ 2.78 (s, 3H), 6.45 (br s, 2H), 7.06 (d, J=5.3 Hz, 1H), 7.39 (d, J=5.3 Hz, 1H), 7.49-7.60 (m, 3H), 7.71 (dd, J=8.6 Hz, 3.2 Hz, 1H), 7.79 (m, 1H), 8.06 (d, J=8.8 Hz, 1H), 8.23-8.28 (m, 2H), 8.32 (dd, J=8.7 Hz, 1.4 Hz, 1H).

EXAMPLE 6

1-Iodo-3-methylsulfanyl-imidazo[1,5-a]pyrazin-8-ylamine

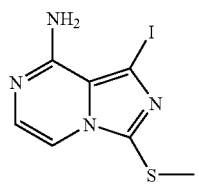

To a suspension of 8-chloro-1-iodo-3-methylsulfanyl-imidazo[1,5-a]pyrazine (2.68 g, 0.00823 mol) in i-PrOH (50 mL) was bubbled NH$_3$ gas for 5 min at −78° C. The mixture was heated at 110° C. overnight. The mixture was cooled to rt and water (10 mL) was added. The off-white solid was collected by filtration. The filtrate was diluted with EtOAc (200 mL), washed with brine (30 mL), and dried over anhydrous sodium sulfate. The crude material was suspended in EtOAc (20 mL), and the title compound was collected by filtration as an off-white solid; LC-MS (ES, Pos.): 307 [MH$^+$]; $^1$H-NMR (DMSO-d$_6$) δ 2.55 (s, 3H), 6.64 (br s, 2H), 7.08 (d, J=4.8 Hz, 1H), 7.53 (d, J=4.8 Hz, 1H).

a) 8-Chloro-1-iodo-3-methylsulfanyl-imidazo[1,5-a]pyrazine

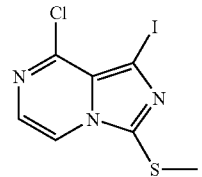

To a solution of 8-chloro-3-methylsulfanyl-imidazo[1,5-a]pyrazine (1.75 g, 0.00876 mol) in DMF (15 mL) was added N-iodosuccinimide (3.94 g, 0.0175 mol), the resulting mixture was stirred at 55° C. for 6 h. The mixture was diluted with EtOAc (200 mL), washed with sat. aq. NaHCO$_3$ (40 mL), water (2×40 mL), brine (40 mL), and dried over anhydrous sodium sulfate. The crude material was purified by silica gel chromatography to give the title compound as a yellow solid; $^1$H NMR (CDCl$_3$, 400 MHz) δ 2.72 (s, 3H), 7.36 (d, J=4.8 Hz, 1H), 7.76 (d, J=4.8 Hz, 1H).

b) 8-Chloro-3-methylsulfanyl-imidazo[1,5-a]pyrazine

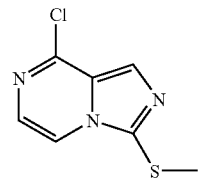

To a solution of (3-chloro-pyrazin-2-ylmethyl)-thiocarbamic acid S-methyl ester (3.05 g, 0.0140 mol) in MeCN (70 mL) were added DMF (4.3 mL, 0.056 mol) and POCl$_3$ (5.2 mL, 0.056 mol) at 0° C. under nitrogen. The reaction mixture was slowly warmed to rt and stirred overnight. The solvent was evaporated under reduced pressure and the residue was cooled at 0° C. and diluted with EtOAc (250 mL), then quenched with sat. aq. NaHCO$_3$ (100 mL). The mixture was washed with brine (50 mL), and dried over anhydrous sodium sulfate. The crude material was purified by silica gel chromatography (Hex:EtOAc=80:20→70:30) to give the title compound as a light-yellow solid; LC-MS (ES, Pos.): 200/202 (3/1) [MH$^+$]; $^1$H NMR (CDCl$_3$, 400 MHz) δ 2.71 (s, 3H), 7.40 (d, J=5.1 Hz, 1H), 7.74 (dd, J=5.1, 1.0 Hz, 1H), 7.90 (s, 1H).

c) (3-Chloro-pyrazin-2-ylmethyl)-thiocarbamic acid S-methyl ester

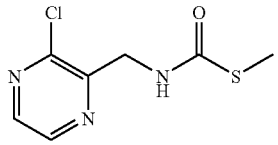

To a suspension of C-(3-chloro-pyrazin-2-yl)-methylamine hydrochloride salt (5.13 g, 0.0285 mol) in dichloromethane (60 mL) were added N,N-diisopropylethylamine (15 mL, 0.085 mol) and carbonochloridothioic acid S-methyl ester (3.15 g, 0.0285 mol) at 0° C. After 5 min, the mixture was warmed to rt and kept at rt overnight. The mixture was diluted with dichloromethane (50 mL), washed with water (30 mL), sat. aq. NaHCO$_3$ (2×30 mL), brine (30 mL), and dried over anhydrous sodium sulfate. The crude product was purified by silica gel chromatography (Hex:EtOAc=70: 30→50:50) to give the title compound as a light-yellow solid; $^1$H NMR (CDCl$_3$, 400 MHz) δ 2.41 (s, 3H), 4.76 (d, J=4.6 Hz, 2H), 6.67 (br s, 1H), 8.34 (d, J=2.5 Hz, 1H), 8.48 (d, J=2.5 Hz, 1H).

EXAMPLE 7

1-(3-Benzyloxy-phenyl)-3-methylsulfanyl-imidazo[1,5-a]pyrazin-8-ylamine

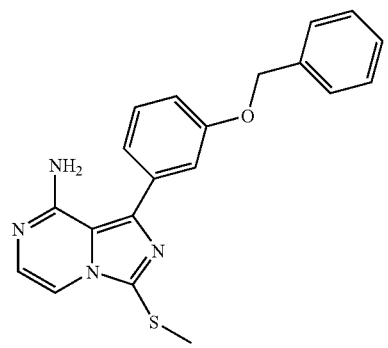

2 N NH$_3$ in i-PrOH (5 mL) and THF (0.325 mL, 0.004 mol) were added to 1-(3-benzyloxy-phenyl)-8-chloro-3-methylsulfanyl-imidazo[1,5-a]pyrazine in Parr bomb and cooled to −78° C. Ammonia was bubbled into the solution for 4 min. The bomb was sealed, stirred and heated at 110° C. overnight. The crude product was loaded onto a TLC prep plate in 5% MeOH in DCM until a decent separation of the product (a blue hue) formed. The product was collected and concentrated in vacuo; LC-MS (ES, Pos.): 363 [MH$^+$]; $^1$H NMR (400 MHz, CD$_3$OD) δ 2.63 (s, 3H), 5.21 (s, 2H), 7.12-7.19 (m, 2H), 7.24 (d, J=7.6 Hz, 1H), 7.28-7.31 (m, 1H), 7.31-7.37 (m, 1H), 7.37-7.43 (m, 2H), 7.45-7.51 (m, 3H), 7.62 (d, J=5.1 Hz, 1H).

a) 1-(3-Benzyloxy-phenyl)-8-chloro-3-methylsulfanyl-imidazo[1,5-a]pyrazine

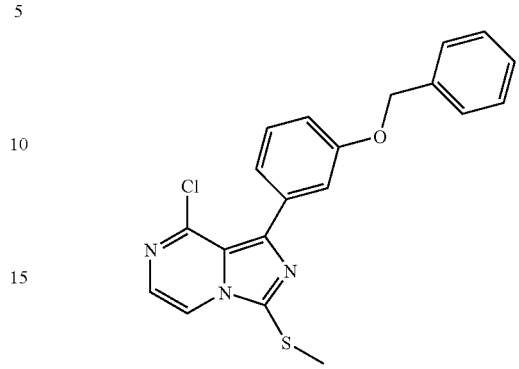

To a solution of [(3-benzyloxy-phenyl)-(3-chloro-pyrazin-2-yl)-methyl]-thiocarbamic acid S-methyl ester (200 mg, 0.0005 mol) in MeCN (10 mL) and DMF (0.12 mL, 0.0015 mol) was added POCl$_3$ (0.14 mL, 0.0015 mol); the resulting mixture was stirred at 55° C. overnight. The mixture was quenched with 2N NH$_3$/iPrOH, then diluted with EtOAc, washed with brine and dried over anhydrous sodium sulfate. The residue was purified by silica gel chromatography (Hex.: EtOAc=80:20→70:30) to give a yellow solid. $^1$H-NMR (CDCl$_3$) confirmed a mixture of the desired product and starting material in ca. 1:1 ratio, which was taken on to next step.

b) [(3-Benzyloxy-phenyl)-(3-chloro-pyrazin-2-yl)-methyl]-thiocarbamic acid S-methyl ester

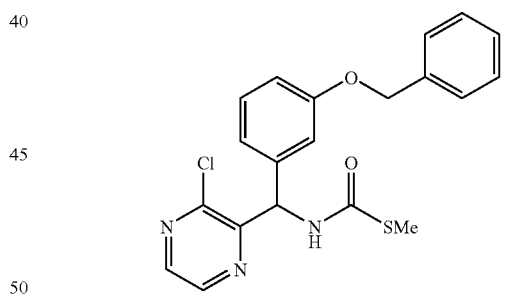

To a suspension of C-(3-benzyloxy-phenyl)-C-(3-chloropyrazin-2-yl)-methylamine hydrochloride salt (3.10 g, 0.00856 mol) in dichloromethane (30 mL) were added N,N-diisopropylethylamine (2.98 mL, 0.0171 mol) and carbonochloridothioic acid S-methyl ester (946 mg, 0.00856 mol) at 0° C. After 5 min, the mixture was warmed to rt and stirred overnight. The mixture was diluted with EtOAc (100 mL), washed with water (20 mL), sat. aq. NaHCO$_3$ (2×30 mL), brine (30 mL), and dried over anhydrous sodium sulfate. The crude product was purified by silical gel chromatogrphy (Hex: EtOAc=70:30→60:40) to give the title compound as a white solid; $^1$H NMR (CDCl$_3$, 400 MHz) δ 2.34 (s, 3H), 5.03 (s, 2H), 6.53 (d, J=6.8 Hz, 1H), 6.87-6.97 (m, 3H), 7.08 (d, J=7.7 Hz, 1H), 7.22 (d, J=7.7 Hz, 1H), 7.30-7.41 (m, 5H), 8.33 (d, J=2.4 Hz, 1H), 8.51 (d, J=2.4 Hz, 1H).

EXAMPLE 8

8-Amino-1-(3-benzyloxy-phenyl)-2H-imidazo[1,5-a]pyrazin-3-one

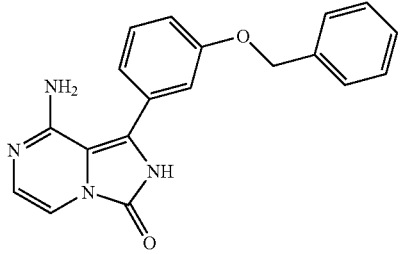

A solution of 1-(3-benzyloxy-phenyl)-8-chloro-2H-imidazo[1,5-a]pyrazin-3-one (100 mg, 0.28 mmol) in i-PrOH (4 mL) was saturated with NH$_3$ at −20° C. and heated 110° C. in a sealed tube for 48 hours. The light brown reaction mixture was partitioned in water and DCM and separated. The aqueous layer was washed with DCM (3×) and the combined organic layers were washed with brine (1×), dried over Na$_2$SO$_4$, filtered, and concentrated in vacuo. The crude material was purified by chromatography on silica gel [eluting with 8% MeOH in DCM], resulting in the title compound as a pale brown solid; $^1$H NMR (DMSO-d$_6$, 400 MHz) δ=5.16 (s, 2H), 5.86 (brs, 2H), 6.70 (d, J=5.2 Hz, 1H), 7.01 (d, J=4.8 Hz, 1H), 7.07-7.14 (m, 2H), 7.24 (brt, J=2 Hz, 1H), 7.32-7.49 (m, 7H); MS (ES+): m/z=333.21 (100) [MH$^+$], HPLC: t$_R$=2.05 min (MicromassZQ, polar_5 min).

EXAMPLE 9

8-Amino-1-(1H-indol-2-yl)imidazo[1,5-a]pyrazine-3(2H)-thione

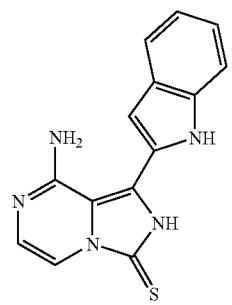

A solution of 1-(1H-indol-2-yl)-3-(methylthio)imidazo[1, 5-a]pyrazin-8-amine (250 mg, 0.85 mmol) in AcOH (10 mL) was treated with 48% hydrogen bromide (0.6 mL) and the mixture heated 120° C. for 24 h. The reaction mixture was then cooled and the suspended solid isolated by filtration and washed with hexane to afford 240 mg of 8-amino-1-(1H-indol-2-yl)imidazo[1,5-a]pyrazine-3(2H)-thione hydrobromide. $^1$H NMR (400 MHz, MeOD) δ ppm 6.89 (d, J=6.06 Hz, 1H), 7.03 (s, 1H), 7.17 (tt, J=7.07, 0.76 Hz, 1H), 7.31 (tt, J=7.33, 1.01 Hz, 1H), 7.52 (dd, J=0.76 Hz, 1H), 7.63-7.76 (m, 2H); MS (ES+): m/z 282.07 [MH+].

EXAMPLE 10

3-(Benzylthio)-1-(1H-indol-2-yl)imidazo[1,5-a]pyrazin-8-amine

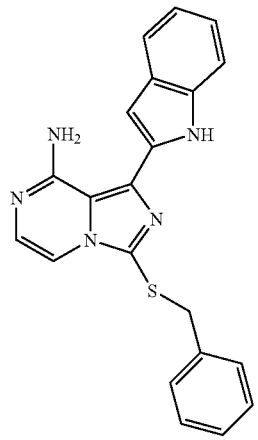

A solution of 8-amino-1-(1H-indol-2-yl)imidazo[1,5-a]pyrazine-3(2H)-thione hydrobromide (10 mg, 0.04 mmol) and benzyl bromide (5.1 uL, 0.043 mmol) in DMF (1.0 mL) was charged with N,N-diisopropylethylamine (18 uL, 0.11 mmol) and stirred at rt for 2 h. The solvent was then removed in vacuo and the crude product was dissolved in purified by preparative TLC eluting with 3% NH$_3$/MeOH in DCM to afford 2.5 mg 3-(benzylthio)-1-(1H-indol-2-yl)imidazo[1,5-a]pyrazin-8-amine. $^1$H NMR (400 MHz, MeOD) δ ppm 4.25 (s, 2H), 6.76 (s, 1H), 6.92 (d, J=5.05 Hz, 1H), 7.06-7.14 (m, 3H), 7.14-7.23 (m, 4H), 7.28 (d, J=5.05 Hz, 1H), 7.48(d, J=8.08 Hz, 1H), 7.63 (d, J=8.08 Hz, 1H); MS (ES+): m/z 373.35 [MH+].

EXAMPLE 11

{[8-Amino-1-(1H-indol-2-yl)imidazo[1,5-a]pyrazin-3-yl]thio}acetonitrile

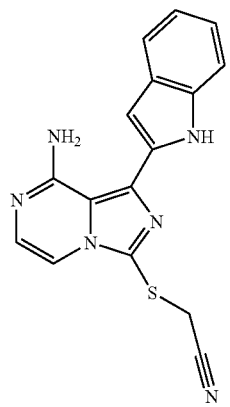

Prepared according to the procedure described above for Example 10 using bromoacetonitrile in place of benzyl bromide. $^1$H NMR (400 MHz, DMSO-d6) δ ppm 4.23 (s, 2H), 6.70 (br. s., 2H), 6.75 (d, J=1.26 Hz, 1H), 7.05 (t, J=7.07 Hz, 1H), 7.15 (t, J=7.07 Hz, 1H), 7.28 (d, J=4.80 Hz, 1H), 7.46(d, J=8.08 Hz, 1H), 7.61 (d, J=7.58 Hz, 1H), 7.74 (d, J=4.80 Hz, 1H) and 11.67 (s, 1H); MS (ES+): m/z 320.52 [MH+].

EXAMPLE 12

1-(1H-Indol-2-yl)-3-{[4-(methylsulfonyl)benzyl]thio}imidazo[1,5-a]pyrazin-8-amine

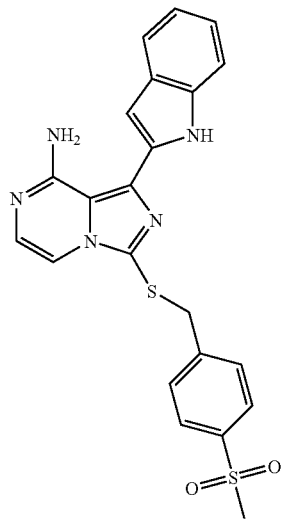

Prepared according to the procedure described above for Example 10 using 4-methylsulphonylbenzyl bromide in place of benzyl bromide. $^1$H NMR (400 MHz, DMSO-d6) δ ppm 3.13 (s, 3H), 4.43 (s, 2H), 6.64 (br. s., 2H), 6.73 (s, 1H), 7.02-7.10 (m, 2H), 7.15 (t, J=8.08, 6.82 Hz, 1H), 7.37 (d, J=4.80 Hz, 1H), 7.48 (d, J=8.34 Hz, 3H), 7.61 (d, J=7.83 Hz, 1H), 7.77 (d, J=8.34 Hz, 2 H) and 11.63 (br. s., 1H); MS (ES+): m/z 449.84 [MH+].

EXAMPLE 13

1-(8-Fluoro-2-phenyl-quinolin-7-yl)-3-([1,3,4]thiadiazol-2-ylsulfanyl)-imidazo[1,5-a]pyrazin-8-ylamine

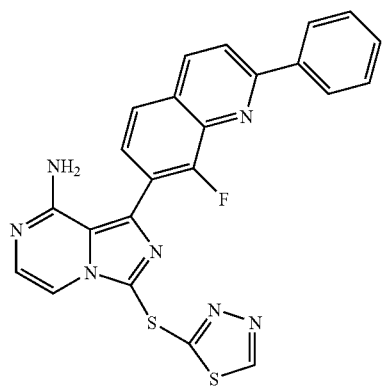

A 10 mL microwave vessel was charged with a solution of 8-amino-1-(8-fluoro-2-phenyl-quinolin-7-yl)-2H-imidazo [1,5-a]pyrazine-3-thione (20 mg, 0.00005 mol), 2-bromo-1, 3,4-thiadiazole (0.017 g, 0.00010 mol) and potassium carbonate (0.021 g, 0.00015 mol) in DMF (1.4 mL, 0.018 mol). The reaction mixture was heated in the microwave at 100° C. for 10 min. The reaction mixture was concentrated in vacuo and purification by Gilson HPLC eluting with 10→65% acetonitrile: H$_2$O afforded the title compound as a light yellow solid. $^1$H NMR (400 MHz, CDCl$_3$): δ=7.31 (d, J=5.05 Hz, 1H), 7.47-7.58 (m, 3H), 7.69-7.80 (m, 3H), 8.05 (d, J=8.84 Hz, 1H), 8.24 (dd, J=8.34, 1.52 Hz, 2H), 8.32 (dd, J=8.72, 1.39 Hz, 1H), 9.07 (s, 1H). MS(ES+): m/z 472.13 (100)[MH$^+$]. HPLC: t$_R$=2.9 min (Open Lynx polar__5 min).

EXAMPLE 14

1-(8-Fluoro-2-phenyl-quinolin-7-yl)-3-(5-methanesulfonylmethylthiazol-2-ylsulfanyl)-imidazo[1,5-a]pyrazin-8-ylamine

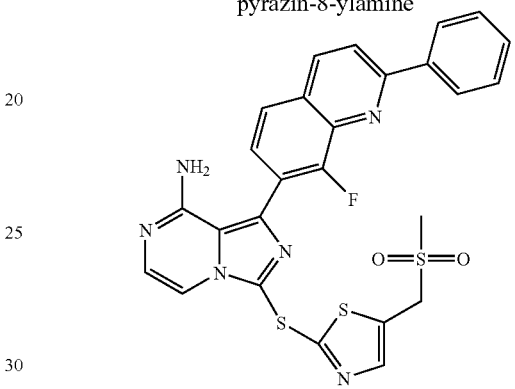

A 10 mL microwave vessel was charged with a solution of 8-amino-1-(8-fluoro-2-phenyl-quinolin-7-yl)-2H-imidazo [1,5-a]pyrazine-3-thione (24 mg, 0.000062 mol), 2-chloro-5-[(methylsulfonyl)methyl]-1,3-thiazole (0.026 g, 0.00012 mol), potassium carbonate in DMF (1.7 mL, 0.022 mol). The reaction mixture was heated in the microwave at 100° C. for 10 min. The reaction mixture was heated again at 120° C. for 10 min in the microwave to get full consumption of SM. Reaction mixture was purified by Gilson HPLC eluting with 10→65% acetonitrile: H$_2$O to afford the title compound as an off white solid. $^1$H NMR (400 MHz, CDCl$_3$): δ=2.85 (s, 3H), 4.36 (s, 2H), 7.34 (d, J=4.80 Hz, 1H), 7.48-7.59 (m, 4H), 7.67 (s, 1H), 7.74-7.78 (m, 2H), 8.04 (d, J=8.84 Hz, 1H), 8.24 (dd, J=8.21, 1.39 Hz, 2H), 8.31 (dd, J=8.72, 1.39 Hz, 1H). MS (ES+): m/z 563.18 (100) [MH$^+$]. HPLC: t$_R$=2.89 min (Open Lynx polar__5 min).

EXAMPLE 15

1-(8-Fluoro-2-phenyl-quinolin-7-yl)-3-(pyrimidin-2-ylsulfanyl)-imidazo[1,5-a]pyrazin-8-ylamine

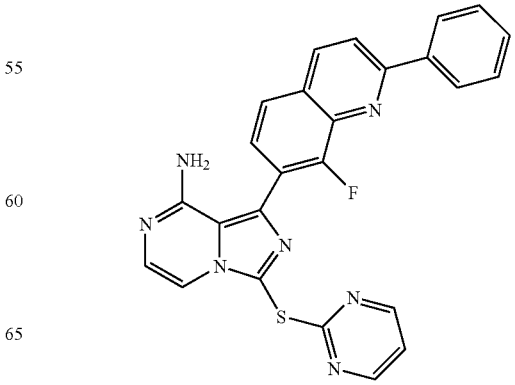

A 10 mL microwave vessel was charged with a solution of 8-amino-1-(8-fluoro-2-phenyl-quinolin-7-yl)-2H-imidazo[1,5-a]pyrazine-3-thione (10 mg, 0.00002 mol), 2-chloropyrimidine (0.0059 g, 0.000052 mol) and potassium carbonate (0.011 g, 0.000077 mol) in DMF. The reaction mixture was heated in the microwave at 100° C. for 10 min followed by 120° C. for 10 min to get full consumption of SM. The reaction mixture was concentrated in vacuo. Purification by Gilson HPLC eluting with 10→60% acetonitrile: H$_2$O afforded the title compound as a light yellow solid. $^1$H NMR (400 MHz, CDCl$_3$): δ=7.07 (t, J=4.93 Hz, 1H), 7.21 (d, J=5.05 Hz, 1H), 7.48-7.59 (m, 4H), 7.74-7.85 (m, 2H), 8.04 (d, J=8.59 Hz, 1H), 8.25 (dd, J=8.21, 1.39 Hz, 2H), 8.31 (dd, J=8.72, 1.39 Hz, 1H), 8.50 (d, J=4.80 Hz, 2H). MS(ES+): m/z 465.98 (100)[MH$^+$]. HPLC: t$_R$=2.75 min (Open Lynx polar_5 min).

EXAMPLE 16

3-(4-Bromo-phenylsulfanyl)-1-(8-fluoro-2-phenyl-quinolin-7-yl)-imidazo[1,5-a]pyrazin-8-ylamine

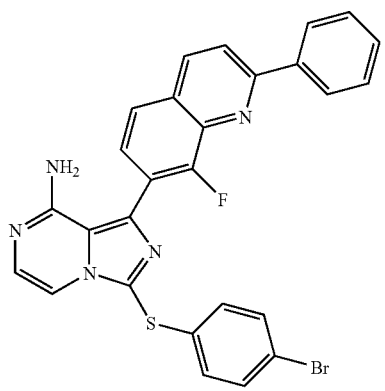

Into a round bottom flask was added 8-amino-1-(8-fluoro-2-phenyl-quinolin-7-yl)-2H-imidazo[1,5-a]pyrazine-3-thione (21 mg, 0.000053 mol), 4-bromobenzenediazonium tetrafluoroborate (0.018 g, 0.000064 mol) and dimethyl sulfoxide (0.1 mL, 0.002 mol) and the reaction mixture was stirred in ice for 30 min. The reaction mixture was cooled, dissolved in DCM and washed with water. Purification by Gilson HPLC eluting with 10→90% acetonitrile: H$_2$O afforded the title compound as a yellow solid. $^1$H NMR (400 MHz, CDCl$_3$): δ=7.13-7.17 (m, 2H), 7.23 (d, J=5.05 Hz, 1H), 7.42 (d, J=8.59 Hz, 2H), 7.49-7.59 (m, 3H), 7.61 (d, J=5.05 Hz, 1H), 7.75-7.78 (m, 2H), 8.05 (d, J=8.59 Hz, 1H), 8.22-8.27 (m, 2H), 8.32 (dd, J=8.72, 1.39 Hz, 1H). MS (ES+): m/z 544.15 (100)[MH$^+$]. HPLC: t$_R$=2.69 min (Open Lynx polar_5 min).

EXAMPLE 17

8-Amino-1-(8-fluoro-2-phenyl-quinolin-7-yl)-imidazo[1,5-a]pyrazine-3-thiol

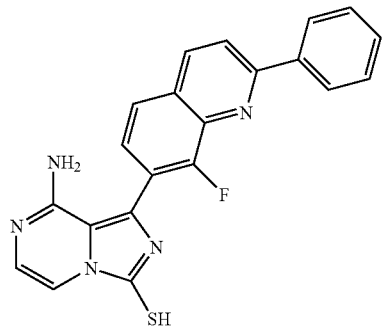

A solution of 1-(8-fluoro-2-phenyl-quinolin-7-yl)-3-methylsulfanyl-imidazo[1,5-a]pyrazin-8-ylamine (24 mg, 0.000060 mol) in AcOH (1 mL, 0.02 mol) was charged with hydrogen bromide (300 uL, 0.006 mol) and refluxed at 118° C. over weekend. An additional 5 eq of HBr were added and the reaction mixture was heated at 118° C. for 4-5 h. The reaction was stopped and cooled in ice. Orange precipitate formed on cooling in ice. The reaction mixture was concentrated in vacuo and washed with hexanes to obtain the title compound as an orange gummy solid. $^1$H NMR (400 MHz, CD$_3$OD d$_4$): δ=7.56 (dd, J=7.33, 3.28 Hz, 1H), 7.63-7.68 (m, 4H), 7.84-7.90 (m, 1H), 8.15 (d, J=8.84 Hz, 1H), 8.19-8.25 (m, 2H), 8.37 (d, J=8.59 Hz, 1H), 8.87 (d, J=8.84 Hz, 1H). MS (ES+): m/z 388.21 (100). HPLC: t$_R$=2.42 min (Open Lynx polar_5 min). Note: Precipitate formed on cooling in ice. At rt the compound is oily.

EXAMPLE 18

1-(8-Fluoro-2-phenyl-quinolin-7-yl)-3-isopropylsulfanyl-imidazo[1,5-a]pyrazin-8-ylamine

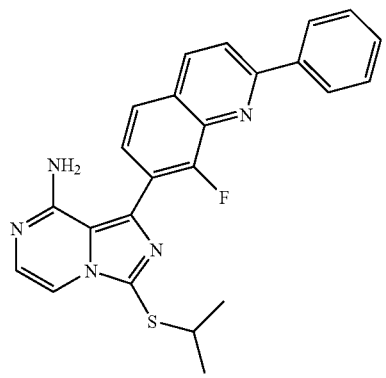

Into a 10 mL microwave vessel was added 8-fluoro-2-phenyl-7-(4,4,5,5-tetramethyl-[1,3,2]dioxaborolan-2-yl)-quinoline (0.0073 g, 0.000021 mol), potassium fluoride (0.002 g, 0.00003 mol), DME (0.4 mL, 0.004 mol), H$_2$O (0.07 mL, 0.004 mol) and DMF (0.078 mL, 0.0010 mol) and the reaction mixture was degassed 3×. Pd(PPh$_3$)$_4$ (0.005 g, 0.000004 mol) was then added to the reaction mixture. The reaction mixture was microwaved on 300 watts, 100° C. for 30 min. Purification by Gilson HPLC eluting with 10→65% acetonitrile:H$_2$O afforded the title compound as a yellow solid. $^1$H NMR (400 MHz, CDCl$_3$): δ=1.40 (d, J=6.82 Hz, 6H), 3.66-3.74 (m, 1H), 7.13 (d, J=5.05 Hz, 1H), 7.49-7.58 (m, 3H), 7.63 (d, J=5.05 Hz, 1H), 7.70-7.79 (m, 2H), 8.04 (d, J=8.59 Hz, 1H), 8.25 (dd, J=8.08, 1.26 Hz, 2H), 8.31 (dd, 1H). MS (ES+): m/z 430.16 (100)[MH+]. HPLC: t$_R$=2.96 min (Open Lynx polar_5 min).

EXAMPLE 19

1-Bromo-3-isopropylsulfanyl-imidazo[1,5-a]pyrazin-8-ylamine

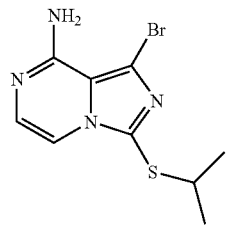

A bohdan block vessel was charged with propanethiol (0.010 g, 0.00014 mol) in DMF (1 mL, 0.01 mol) and the reaction mixture was degassed 3×. Sodium hydride was then added and the reaction mixture was stirred at rt for 10 min. 1,3-Dibromo-imidazo[1,5-a]pyrazin-8-ylamine (20 mg, 0.00007 mol) was added and the reaction mixture was heated at 70° C. for 4 h. The reaction mixture was concentrated in vacuo to give the title compound as a brown solid. $^1$H NMR (400 MHz, CD$_3$OD-d$_4$): δ=1.09 (d, J=6.82 Hz, 9H), 1.28 (d, 9H), 3.45-3.57 (m, 1H), 7.10 (d, J=5.05 Hz, 1H), 7.69 (d, J=5.05 Hz, 1H). MS(ES+): m/z 288.95 (100)[MH$^+$]. HPLC: t$_R$=2.13 min (Open Lynx polar_5 min).

EXAMPLE 20

1,3-Dibromo-imidazo[1,5-a]pyrazin-8-ylamine

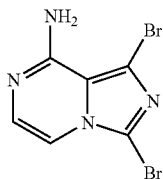

20 M of NH$_3$ in H$_2$O(10 mL) was added to a suspension of 1,3-Dibromo-8-chloro-imidazo[1,5-a]pyrazine (1.726 g, 0.007425 mol) in 2-Butanol (7.49 mL, 0.0817 mol). The mixture was heated in an oil bath set at 90° C. overnight. The reaction mixture was concentrated in vacuo and purified by flash column chromatography using 1→6% MeOH in DCM to obtain the title compound as a yellow solid. MS (ES+): m/z 294.83 (85) [MH$^+$]. HPLC: t$_R$=1.58 min (Open Lynx polar_5 min). $^1$H NMR (400 MHz, CD$_3$OD):δ=7.10 (d, J=5.05 Hz, 1H), 7.43 (d, J=5.05 Hz, 1H)

1,3-Dibromo-8-chloro-imidazo[1,5-a]pyrazine

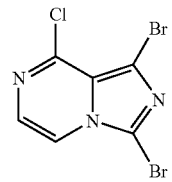

Into a round bottom flask were added 8-Chloro-imidazo[1,5-a]pyrazine (50 mg, 0.0003 mol) and DMF (0.290 mL, 0.00374 mol). The reaction mixture was cooled in an ice-brine bath (−5° C.). NBS (60.8 mg, 0.000342 mol) dissolved in DMF (0.19 mL, 0.0024 mol) was added via syringe to the reaction mixture. Water was added to the reaction mixture and yellow solid started precipitating out. The solid was filtered and washed with water and dried on vacuum to afford the title compound as a yellow solid.

8-Chloroimidazo[1,5-a]pyrazine

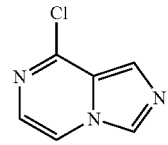

In an oven dried flask filled with nitrogen was added N-(3-Chloro-pyrazin-2-ylmethyl)-formamide (3.8 g, 0.022 mol) followed by MeCN (60 mL, 1 mol) and the reaction mixture was degassed 3×. POCl$_3$ (10 mL, 0.1 mol) was added to the reaction mixture dropwise and the reaction mixture was stirred at rt for 5 min before DMF (couple of drops) was added in one portion. The reaction mixture was heated at 75° C. overnight under a consistent N$_2$ flow. The excess of POCl$_3$ was removed under reduced pressure and the residue was quenched with 2 N NH$_3$ in i-PrOH at 0° C. with vigorous stirring to adjust the pH to 9. The crude reaction mixture was then charged with water and the aqueous layer was washed with DCM. The combined organic layer was dried over Na₂SO₄, filtered and concentrated under reduced pressure to obtain the title compound as a brown solid.

3-Chloropyrazin-2-yl)methylformamide

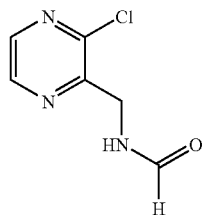

To a solution of C-(3-chloro-pyrazin-2-yl)-methylamine hydrochloride salt (6.0 g, 0.033 mol)) (synthesis described in WO2005/097800) in DCM (81 mL, 1.3 mol) was added N-(3-dimethylaminopropyl)-N'-ethylcarbodiimide hydrochloride (9.6 g, 0.050 mol), DIPEA (8.7 mL, 0.050 mol), 1-hydroxybenzotriazole hydrate (5.1 g, 0.033 mol) and formic acid (1.6 mL, 0.043 mol). DMF (9 mL, 0.1 mol) was added to improve the solubility. The reaction was stirred at rt for 16 h under N₂. Reaction mixture was concentrated in vacuo. Purification by flash column chromatography on silica gel using MeOH in DCM (1→7%) yielded the title compound as a light yellow solid. ¹H NMR (400 MHz, CD₃OD): δ=4.72 (s, 2H), 8.26 (s, 1H), 8.39 (d, J=1.77 Hz, 1H), 8.57 (d, J=2.53 Hz, 1H). MS (ES+): m/z 172.17 (20) [MH⁺]. HPLC: t$_R$=1.63 min (Open Lynx polar__5 min).

EXAMPLE 21

3-tert-Butylsulfanyl-1-(8-fluoro-2-phenyl-quinolin-7-yl)-imidazo[1,5-a]pyrazin-8-ylamine

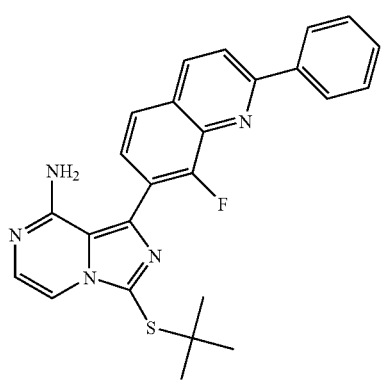

Into a 10 mL microwave vessel was added 1-bromo-3-tert-butylsulfanyl-imidazo[1,5-a]pyrazin-8-ylamine (23 mg, 0.000076 mol), 8-fluoro-2-phenyl-7-(4,4,5,5-tetramethyl-[1, 3,2]dioxaborolan-2-yl)-quinoline (0.032 g, 0.000092 mol), potassium fluoride (0.0089 g, 0.00015 mol), DME (2 mL, 0.02 mol), H₂O (0.3 mL, 0.02 mol), DMF (0.34 mL, 0.0044 mol) and the reaction mixture was degassed 3×. Pd(PPh₃)₄ (0.02 g, 0.00002 mol) was then added to the reaction mixture and the vessel was sealed. The reaction mixture was microwaved on 300 watts, 100° C. for 30 min. Reaction mixture was concentrated in vacuo. Purification by Gilson HPLC eluting with 10→75% acetonitrile: H₂O afforded the compound with pinacole impurity. The compound was then passed through a 2 g silica gel cartridge eluting with 6% EtOAc in hexanes followed by 4% MeOH in DCM to afford the pure compound as a yellow solid. ¹H NMR (400 MHz, CD₃OD-d₄): δ=1.43 (s, 9H), 7.22 (d, J=5.05 Hz, 1H), 7.50-7.59 (m, 3H), 7.68-7.74 (m, 1H), 7.90-7.96 (m, 2H), 8.20 (d, J=8.59 Hz, 1H), 8.26 (d, J=7.83 Hz, 2H), 8.51 (dd, J=8.84, 1.26 Hz, 1H). MS(ES+):m/z 444.17 (100)[MH+]. HPLC: t$_R$=3.24 min (Open Lynx polar__5 min).

EXAMPLE 22

1-Bromo-3-tert-butylsulfanyl-imidazo[1,5-a]pyrazin-8-ylamine

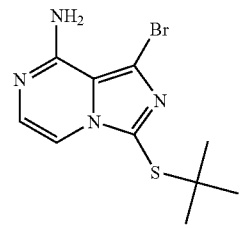

A bohdan block vessel was charged with 2-methyl-2-propanethiol (20 uL, 0.0002 mol) in DMF (2 mL) and the reaction mixture was degassed 3×. Sodium hydride (0.01 g, 0.0004 mol) was then added and the reaction mixture was stirred at rt for 10 min. 1,3-Dibromo-imidazo[1,5-a]pyrazin-8-ylamine (30 mg, 0.0001 mol) was added to the reaction mixture and the reaction mixture was heated at 70° C. overnight. The reaction mixture turned red in color as the reaction progressed. The reaction mixture was concentrated and purified by prep TLC using a mixture of 7 N5% NH₃ in MeOH/DCM to afford the title compound as a white solid. ¹H NMR (400 MHz, CD₃OD-d₄): δ=1.37 (s, 9H), 7.13 (d, J=5.05 Hz, 1H), 7.84 (d, J=5.05 Hz, 1H). MS(ES+): m/z 303.02 (100) [MH⁺]. HPLC: t$_R$=2.30 min (Open Lynx polar__5 min).

EXAMPLE 23

1-(8-Fluoro-2-phenyl-quinolin-7-yl)-3-methanesulfinyl-imidazo[1,5-a]pyrazin-8-ylamine

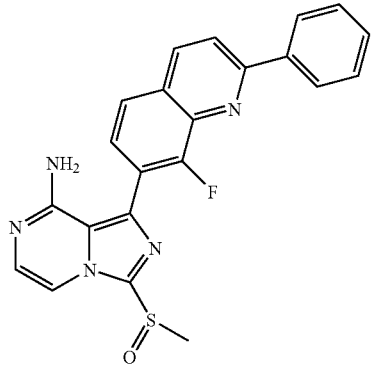

A solution of m-chloroperbenzoic acid (0.013 g, 0.000075 mol) in DCM (0.4 g, 0.005 mol) was added slowly to asolution of 1-(8-fluoro-2-phenyl-quinolin-7-yl)-3-methylsulfanyl-imidazo[1,5-a]pyrazin-8-ylamine (30 mg, 0.000075 mol) in DCM (2 mL, 0.04 mol) at −78° C. The reaction mixture was allowed to stir at that temp for 30 min. The reaction mixture was transferred to an ice-bath and stirred for 1 h. 50% consumption of SM was observed. The reaction mixture was stirred in ice-bath for 1 h. An additional 0.5 eq of m-chloroperbenzoic acid was added to the reaction mixture and the reaction mixture was warmed to rt and stirred for 2 h. The reaction mixture was concentrated in vacuo. Purification by prep TLC (7% MeOH in DCM) afforded the title compound as a light yellow solid. $^1$H NMR (400 MHz, CDCl$_3$): δ=5.13 (br. s., 2H), 7.32 (d, J=5.05 Hz, 1H), 7.48-7.60 (m, 3H), 7.69 (dd, J=8.46, 6.44 Hz, 1H), 7.76-7.81 (m, 1H), 8.06 (d, J=8.84 Hz, 1H), 8.15 (d, J=5.05 Hz, 1H), 8.25 (dd, J=8.21, 1.39 Hz, 2H), 8.32 (dd, J=8.72, 1.39 Hz, 1H). MS (ES+): m/z 417.95 (100)[MH+]. HPLC: t$_R$=2.63 min (Open Lynx polar_5 min).

EXAMPLE 24

[8-Amino-1-(1H-indol-2-yl)-imidazo[1,5-a]pyrazin-3-ylsulfanyl]-acetic acid

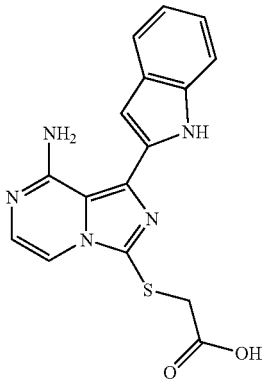

A solution of [8-amino-1-(1H-indol-2-yl)-imidazo[1,5-a]pyrazin-3-ylsulfanyl]-acetic acid ethyl ester (6.7 mg, 0.000018 mol) and conc. HCl (3.0 mL) was stirred at rt for 5 h. The conc. HCl was removed in vacuo to afford 6 mg, 90% yield, of the title compound as a yellow solid. $^1$H NMR (400 MHz, DMSO-d$_6$) δ ppm =4.12 (s, 2H), 6.82 (s, 1H), 7.07 (t, J=7.83, 7.07 Hz, 11H), 7.14-7.22 (m, 2H), 7.48 (d, J=8.08 Hz, 11H), 7.63 (d, J=7.83 Hz, 11H), 7.71 (d, J=5.56 Hz, 1H) and 11.75 (s, 1H); MS (ES+): m/z 339.92 [M+]. HPLC: t$_R$=1.94 min (OpenLynx: polar_5 min).

The following Examples in Table Z.111 below were prepared according to the schemes and procedures described previously.

TABLE Z.111

| Example | Structure | Name | MH+ |
|---|---|---|---|
| 25 | 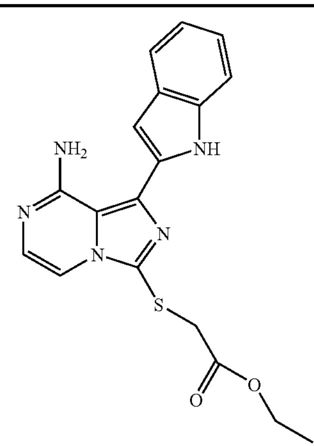 | [8-Amino-1-(1H-indol-2-yl)-imidazo[1,5-a]pyrazin-3-ylsulfanyl]-acetic acid ethyl ester | 367.68 |

TABLE Z.111-continued
| Example | Structure | Name | MH+ |
| --- | --- | --- | --- |
| 26 | 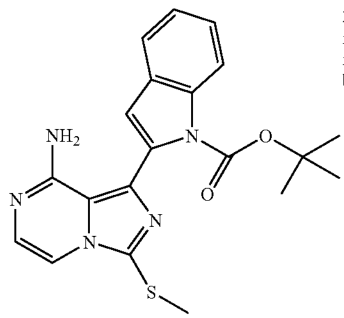 | 2-(8-Amino-3-methylsulfanyl-imidazo[1,5-a]pyrazin-1-yl)-indole-1-carboxylic acid tert-butyl ester | 395.92 |
| 27 | 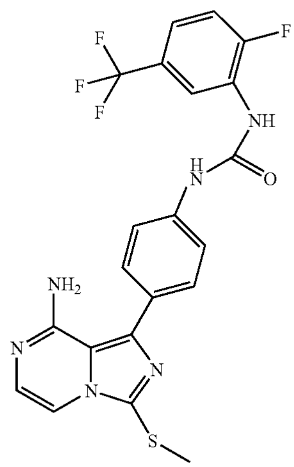 | 1-[4-(8-Amino-3-methylsulfanyl-imidazo[1,5-a]pyrazin-1-yl)-phenyl]-3-(2-fluoro-5-trifluoromethyl-phenyl)-urea | 476.91 |
The invention claimed is:
1. A compound selected from:
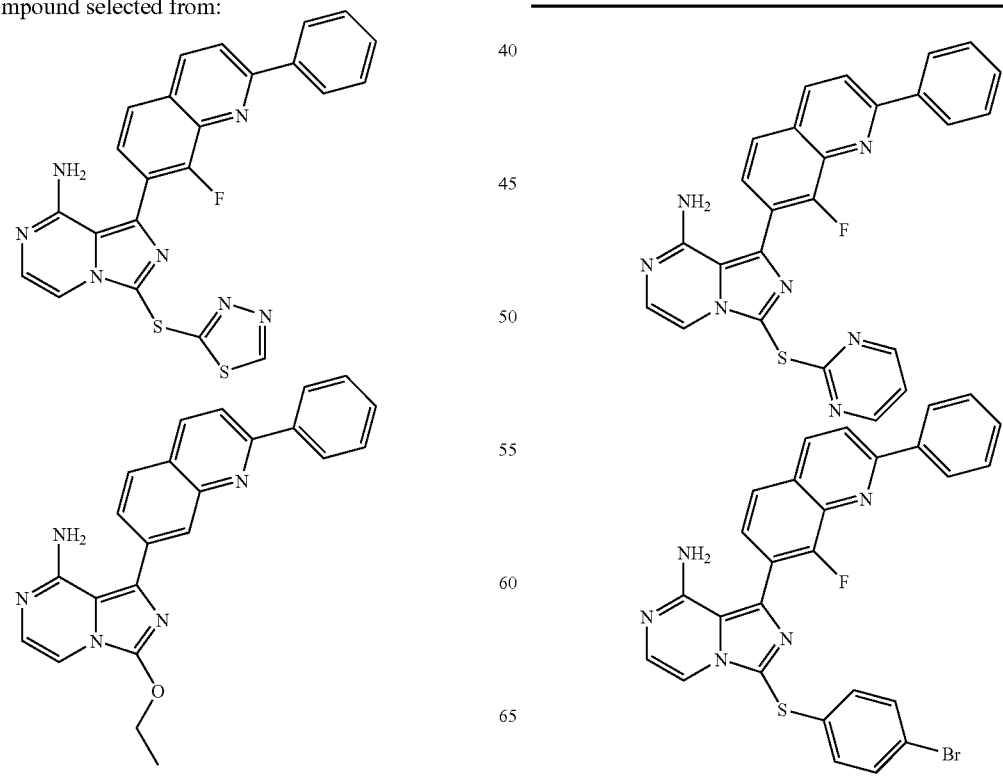

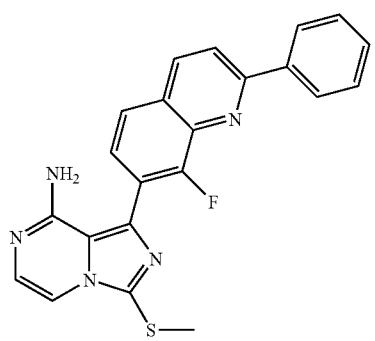
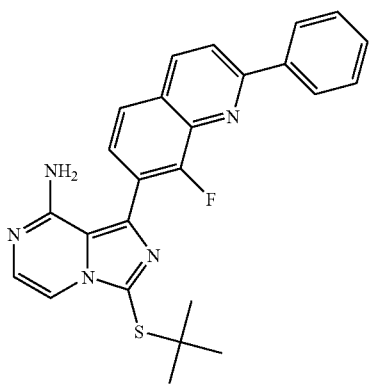
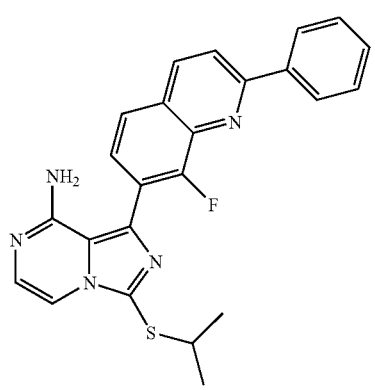
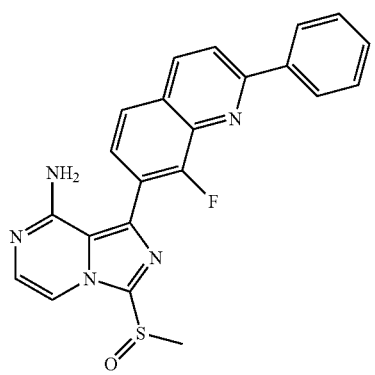
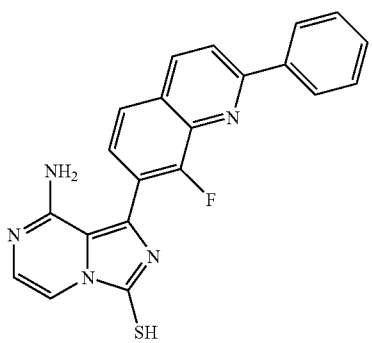
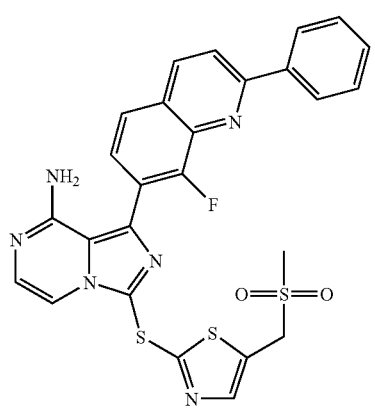
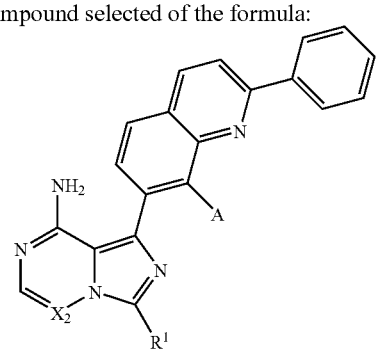
or a pharmaceutically acceptable salt thereof.
2. A pharmaceutical composition comprising the compound or salt of claim 1 and a pharmaceutically acceptable carrier.
3. A compound selected of the formula:
wherein $X_2$ is CH, A is either H or F, $R^1$ is —$XR^a$, X is either S or O, and $XR^a$ is any one of:

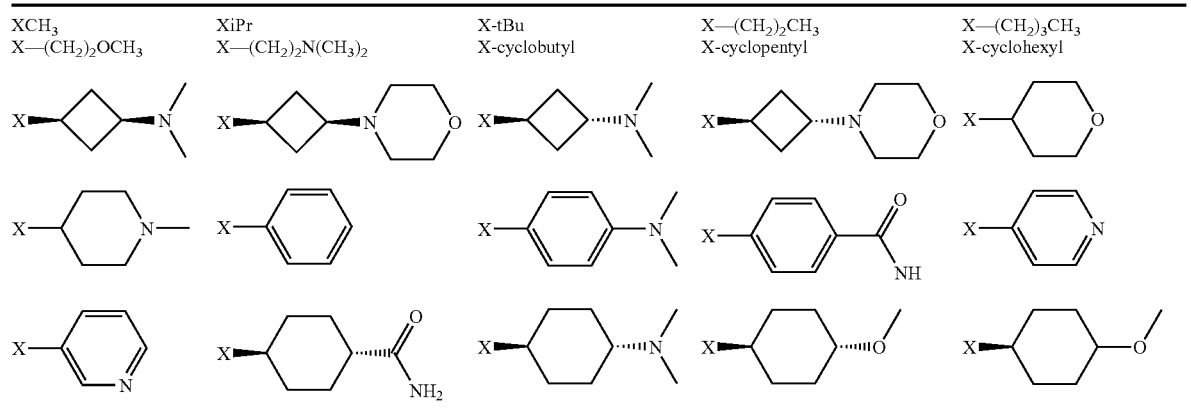
or a pharmaceutically acceptable salt thereof.
4. A pharmaceutical composition comprising the compound or salt of claim 3 and a pharmaceutically acceptable carrier.
5. A compound selected of the formula:
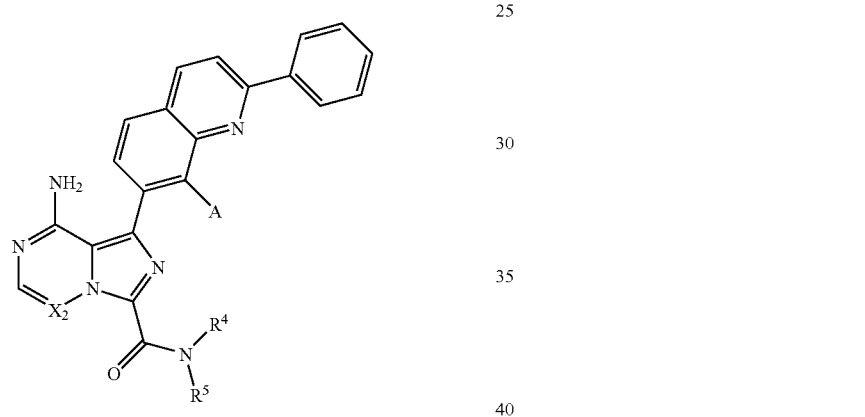
wherein $X_2$ is CH, A is either H or F, and $NR^4R^5$ is any one of:
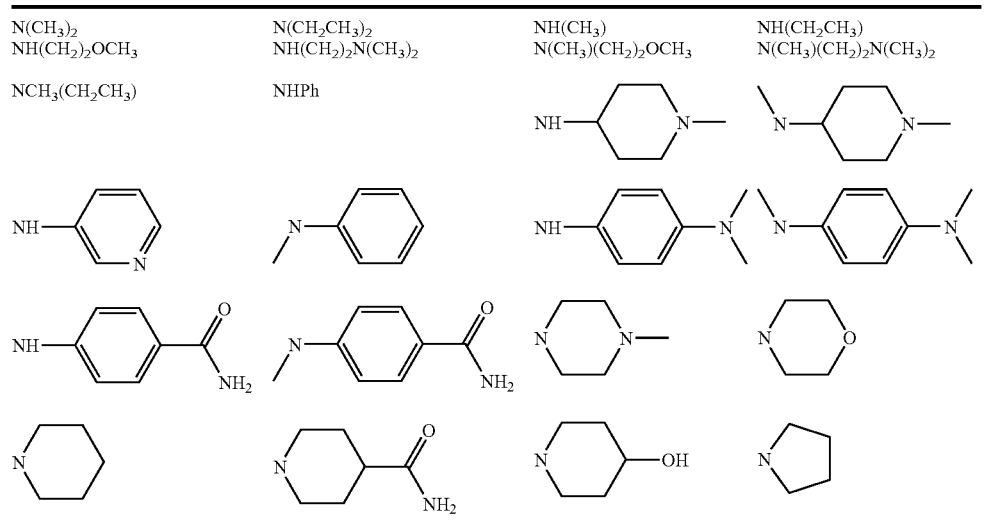
or a pharmaceutically acceptable salt thereof.

6. A pharmaceutical composition comprising the compound or salt of claim 5 and a pharmaceutically acceptable carrier.
7. A compound selected from the one of:
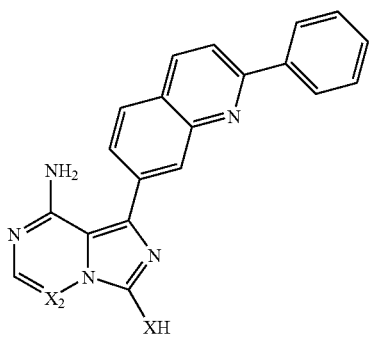
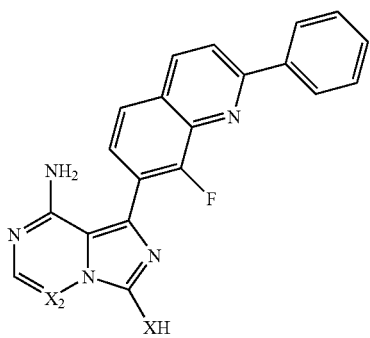
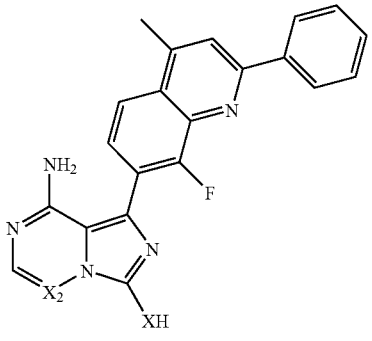
or
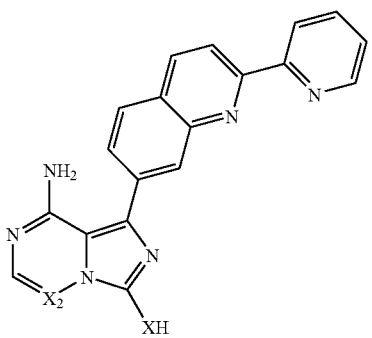
wherein $X_2$ is CH, and X is either O or S; or a pharmaceutically acceptable salt thereof.
8. A pharmaceutical composition comprising the compound or salt of claim 7 and a pharmaceutically acceptable carrier.
* * * * *